US012751783B2

(12) United States Patent
Brubaker et al.

(10) Patent No.: US 12,751,783 B2
(45) Date of Patent: Oct. 6, 2026

(54) ROBOTIC SURGERY SYSTEM WITH DYNAMIC AI ARBITRATION AND RISK-DRIVEN AUTONOMY

(71) Applicants: William Brubaker, Palo Alto, CA (US); Paul Davis, Los Altos, CA (US)

(72) Inventors: William Brubaker, Palo Alto, CA (US); Paul Davis, Los Altos, CA (US)

( * ) Notice: Subject to any disclaimer, the term of this patent is extended or adjusted under 35 U.S.C. 154(b) by 0 days.

(21) Appl. No.: 19/335,181

(22) Filed: Sep. 22, 2025

(65) Prior Publication Data

US 2026/0076760 A1 Mar. 19, 2026

Related U.S. Application Data

(63) Continuation-in-part of application No. 18/611,155, filed on Mar. 20, 2024, now abandoned.

(51) Int. Cl.

| | |
|---|---|
| ***A61B 34/35*** | (2016.01) |
| ***A61B 34/10*** | (2016.01) |
| ***G16H 40/63*** | (2018.01) |

(52) U.S. Cl.

CPC .............. *A61B 34/35* (2016.02); *A61B 34/10* (2016.02); *G16H 40/63* (2018.01)

(58) Field of Classification Search

None

See application file for complete search history.

(56) References Cited

U.S. PATENT DOCUMENTS

| | | | |
|---|---|---|---|
| 3,661,143 | A | 5/1972 | Henkin |
| 4,029,099 | A | 6/1977 | Fifield |
| 4,319,573 | A | 3/1982 | Whitlock |
| 4,421,509 | A | 12/1983 | Schneider et al. |
| 4,483,688 | A | 11/1984 | Akiyama |
| 4,583,967 | A | 4/1986 | Harris |

(Continued)

FOREIGN PATENT DOCUMENTS

| | | | |
|---|---|---|---|
| EP | 0108736 | A1 | 5/1984 |
| EP | 2956204 | B1 | 12/2015 |

(Continued)

*Primary Examiner* — Arslan Azhar

(57) ABSTRACT

A robotic surgical system integrates artificial intelligence (AI) to enable dynamic inference arbitration and risk-driven autonomy. The system includes a surgeon console, robotic arms, and a control system with memory and processors configured to execute real-time surgical workflows. AI modules analyze intraoperative data, such as imaging, sensor input, and instrument telemetry, and compute context alignment scores to guide module selection, forecasting, and fallback execution. Confidence metrics are monitored, with thresholds triggering surgeon alerts, handoff, or autonomous continuation. The system supports intraoperative adaptation, surgeon fatigue detection, and real-time annotation of AI outputs for traceability. It enables improved tissue recognition, predictive planning, and context-aware adjustments through training on historical surgical data. AI-assisted decision support, deviation handling, and performance monitoring enhance safety and personalization across diverse procedures. The architecture supports modular deployment, continuous learning, and integration of multimodal data sources for precision-guided robotic surgery.

20 Claims, 37 Drawing Sheets

(56) References Cited

U.S. PATENT DOCUMENTS

| | | | |
|---|---|---|---|
| 4,704,177 | A | 11/1987 | Vaillancourt |
| 4,801,296 | A | 1/1989 | Vaillancourt |
| 4,826,486 | A | 5/1989 | Palsrok et al. |
| 4,830,914 | A | 5/1989 | Vaillancourt |
| 4,834,706 | A | 5/1989 | Beck et al. |
| 5,248,306 | A | 9/1993 | Clark et al. |
| 5,531,695 | A | 7/1996 | Swisher |
| 5,728,061 | A | 3/1998 | Ahmed |
| 5,803,509 | A | 9/1998 | Adams |
| 5,957,894 | A | 9/1999 | Kerwin et al. |
| 10,322,247 | B1 | 6/2019 | Radcliffe, Jr. |
| 11,241,566 | B1 | 2/2022 | Lindsay |
| 11,389,248 | B1 | 7/2022 | Roh et al. |
| 12,089,905 | B1 | 9/2024 | Roh et al. |
| 2003/0032944 | A1 | 2/2003 | Cawood |
| 2006/0271019 | A1 | 11/2006 | Stoller et al. |
| 2007/0225688 | A1 | 9/2007 | Goodwin |
| 2007/0244468 | A1 | 10/2007 | Kostandaras |
| 2010/0228231 | A1 | 9/2010 | Weigel et al. |
| 2010/0286667 | A1 | 11/2010 | Paz |
| 2011/0087181 | A1 | 4/2011 | Bidwell et al. |
| 2012/0089129 | A1 | 4/2012 | Engelhardt |
| 2012/0184944 | A1 | 7/2012 | Tomes et al. |
| 2012/0214337 | A1 | 8/2012 | Schnell et al. |
| 2012/0232547 | A1 | 9/2012 | Cohen |
| 2013/0172840 | A1 | 7/2013 | Lampotang et al. |
| 2014/0100547 | A1 | 4/2014 | Lyons et al. |
| 2014/0163730 | A1* | 6/2014 | Mian ...................... B25J 9/1689 700/248 |
| 2015/0051588 | A1 | 2/2015 | Miller et al. |
| 2015/0126975 | A1 | 5/2015 | Wuthier |
| 2015/0290449 | A1 | 10/2015 | Yanik |
| 2016/0051395 | A1 | 2/2016 | Ugarte |
| 2016/0193073 | A1 | 7/2016 | Kinsey et al. |
| 2017/0368308 | A1 | 12/2017 | Hofius et al. |
| 2018/0169377 | A1 | 6/2018 | Hickmott et al. |
| 2018/0304045 | A1 | 10/2018 | Glithero et al. |
| 2019/0314188 | A1 | 10/2019 | Barrientos |
| 2019/0321587 | A1 | 10/2019 | McMenamin et al. |
| 2019/0321593 | A1 | 10/2019 | Crawford |
| 2020/0269011 | A1 | 8/2020 | Carlsson |
| 2022/0296871 | A1 | 9/2022 | Hickman |
| 2023/0054209 | A1* | 2/2023 | Roh ....................... A61B 34/76 |

FOREIGN PATENT DOCUMENTS

| | | | | |
|---|---|---|---|---|
| WO | WO-2014089316 | A1 * | 6/2014 | .............. B25J 9/161 |
| WO | WO-2019180700 | A1 * | 9/2019 | ............. G05D 1/223 |

* cited by examiner

ROBOTIC SURGERY SYSTEM WITH DYNAMIC AI ARBITRATION AND RISK-DRIVEN AUTONOMY

BACKGROUND

Field of the Invention

The present disclosure relates to robotic surgery, and more specifically, to surgery incorporating artificial intelligence ("AI").

Description of the Related Art

Robotic surgery, also known as robot-assisted surgery, enables physicians to perform a wide range of complex procedures with greater precision, flexibility, and control than is typically achievable with conventional surgical techniques. Robotic systems may be employed in both minimally invasive and traditional open surgeries.

A typical robotic surgical system comprises a camera arm and multiple mechanical arms equipped with surgical instruments. The surgeon operates these robotic arms from a computer console situated near the operating table. The console provides a high definition, magnified, three-dimensional (3D) view of the surgical site. During the procedure, the surgeon leads a team of assistants who support the operation.

Compared to traditional techniques, robotic systems significantly enhance surgical precision, flexibility, and control. These systems enable surgeons to visualize the surgical site with superior clarity, thereby facilitating delicate and complex procedures that might otherwise be difficult or unfeasible using conventional methods.

One commonly used robotic surgical system includes a high-resolution camera and robotic arms fitted with surgical tools. The surgeon controls these arms via a viewing console, typically located in the same room as the patient. However, the system may also support remote operation—telesurgery—where the console is situated at a geographically distant location. The surgeon views a magnified 3D image of the patient's anatomy. Each robotic arm's trajectory is dynamically refined by an AI engine utilizing probabilistic models that adjust for patient-specific anatomical variations.

Robotic surgical systems offer numerous advantages over traditional techniques. These benefits include enhanced dexterity of the robotic instruments, which allows surgeons to access anatomically restricted or hard-to-reach areas more effectively than with the human hand. The systems provide improved visualization of the operative field through high-definition magnification displayed on the surgeon's screen, enabling greater surgical precision. Additionally, robotic systems reduce surgeon fatigue and eliminate hand tremors, which is particularly advantageous during prolonged surgical procedures. For patients, robotic surgery typically results in shorter hospital stays, faster recovery times, and a lower risk of infection. Further benefits include decreased blood loss, reduced need for blood transfusions, less postoperative pain and scarring, and a quicker return to normal activities and overall function.

Robotic surgical systems provide many benefits, including but not limited to: improved dexterity of the robotic devices (compared to a surgeon's hand), which allows for access to hard-to-reach places; improved visualization of the surgical site due to the magnification of the camera which is displayed on the surgeon's viewing screen; less surgeon fatigue; elimination of a surgeon's hand tremors particularly during long surgical procedures; shorter hospital stays and faster recovery for the patient; reduced patient infection; lower blood loss and fewer blood transfusions; less pain and scarring; less time after surgery for the patient to return to normal activity; faster return to normal function; and the like.

SUMMARY

An object of the present invention is to provide a robotic surgical system with a control system with a memory storing instructions Another object of the present invention is to provide a robotic surgical system with a control system, and a monitor module to monitor confidence levels and execute a fallback response when the confidence metric falls below a surgeon-adjustable reliability threshold.

A further object of the present invention is to provide a robotic surgical system with a control system, a monitor module and an annotate system for AI-generated outputs with version identifiers, confidence scores, and inference metadata for traceability and retrospective audit.

These and other objects of the present invention are achieved in a robotic surgical system. A surgeon console is operatively connected to one or more robotic arms. A control system includes at least one processor and memory storing instructions that, when executed, cause the system to: receive real-time intraoperative data comprising at least one of instrument telemetry, anatomical imaging, sensor input, or surgeon interaction patterns. A query module is provided. At least one artificial intelligence (AI) inference module is associated with metadata including procedural domain, training provenance, performance benchmarks, and override statistics. A module is computed with a context alignment score using at least one of similarity metrics, reinforcement learning-based alignment, or heuristic-AI hybrid inference; An AI module is selected based on the alignment score to generate intraoperative guidance. A temporal forecasting module operates to anticipate module performance degradation or contextual divergence. A module arbitration event is initiated prior to predicted degradation, and includes at least one of dynamic module switching, ensemble inference, concurrent dual-module execution, or notification to the surgeon. A monitor module monitors confidence levels and executes a fallback response when the confidence metric falls below a surgeon-adjustable reliability threshold. An annotate module is provide for all AI-generated outputs with version identifiers, confidence scores, and inference metadata for traceability and retrospective audit.

DETAILED DESCRIPTION

Figure 1A:
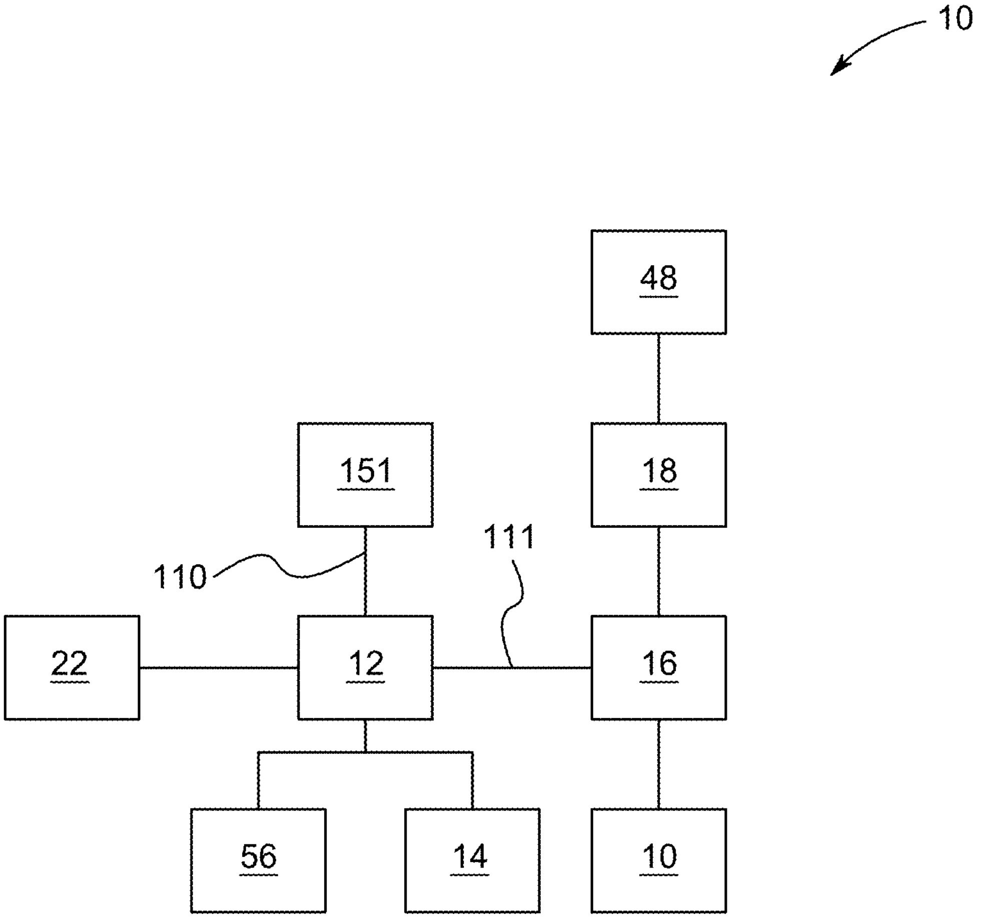
FIG. 1A illustrates one embodiment of a robotic surgical system of the present invention.

In one embodiment, illustrated in FIG. 1A, a robotic surgical system 10 includes: a surgeon console 12, optical system 14, patient console 16, surgical instruments 18, and the like. In one embodiment, robotic surgical system 10 includes a surgeon computer 151 (more fully disclosed hereafter), a surgical robot 20, and a robotic surgery control system 22. In one embodiment, a robotic surgical manipulator 152, hereafter the "patient console 16" has one or more robotic surgical arms 54. As a non-limiting example, robotic surgical manipulator 152 (16) has a base from which the surgical instruments 18 is supported. In one embodiment, surgical instruments 18 are each supported by the positioning linkage and the actuating portion 158 of the arms 54, as more fully discussed hereafter.

In one embodiment, only a surgeon console 12 is provided, with all or some of the elements found in the optical system 14 and patient console 16. In one embodiment, robotic surgical system 10, surgeon console 12, and patient console 16 are provided. The other elements can be at either one. An assistant can work with the surgeon.

As a non-limiting example, robotic surgery surgical system 10 is not limited to robots performing your surgery, as a non-limiting example, surgeon console 12 connects a surgeon to robotic system 20 and to the patient. In one embodiment, surgeon console 12 includes a set of finely tuned hand controls and a high-definition screen. As a non-limiting example, the surgeon controls robotic arms 54 and surgical instruments 18 using the surgeon's hands. Each arm's trajectory is dynamically refined by the AI engine using probabilistic models that account for patient-specific anatomical deviations.

As non-limiting examples, robotic surgical system 10 can be used in one or more of the following areas: ophthalmology, cardiothoracic surgery, otolaryngology, gastrointestinal surgery, orthopedic surgery, neurosurgery, organ transplantation, urology, pediatric surgery, and the like.

As a non-limiting example, robotic surgical system 10 includes surgeon console 12. Patient console 16, with arms 54 configured to be coupled to surgical instruments 18. A robotic surgery control system 22 is coupled to the surgical robot 20 A surgical computing device 151 is coupled to the robotic surgery control system 22. The surgical computing device 151 includes a memory 63 with programmed instructions 67 of surgical computing device 151 from a database 6161 one or more processors 62 are coupled to the memory 63 and configured to execute stored. Database 6161 uses one or more algorithms relative to search engine 65 for selection, full creation, partial creation, and the like, of programmed instructions 67. The one or more algorithms 65 selected from at least one of: supervised learning; classification and regression; decision tree; random forest; support vector machines; Naïve Bayes; linear regression; logistic regression; enhanced imaging; image recognition; treatment planning; risk assessment; robot-assisted navigation; path planning; collision avoidance; autonomous robotics; steady hand assistance; intraoperative decision support; real-time feedback; alert and warning; postoperative monitoring and analysis; prediction; patient outcomes: continuous learning and improvement; ad data analysis. The programmed instructions 67 of surgical computing device 151 being used by a surgeon and the robotically assisted surgical system to perform one or more of: train at least one machine learning model; improve at least one machine learning models and apply the machine learning model to generate one or more parameters used for a surgical procedure, a pre-operative plan or procedure, or a postoperative surgery plan or procedure that can be used by the surgeon.

In one embodiment, the programmed instructions 67 of surgical computing device 151 are directed to improved patient image and video analysis. As non-limiting examples, the programmed instructions 67 of surgical computing device 151 are directed to and execute enhanced imaging AI algorithms to improve the quality and interpretation of medical imaging. In one embodiment, the AI algorithms are used for one or more of: real-time identification of anatomical structures, tumors, and critical tissues; surgical planning; treatment planning to create personalized surgical plans; risk assessment to predict potential complications; surgical robot navigation; plan optimal paths for at least one of the arms 54 and the surgical instruments 18; provide collision avoidance to detect and prevent collisions between the surgical instruments 18 and anatomical structures in real-time; autonomous robotics; steady hand assistance for improved stability and precision to surgical instruments 18; intraoperative decision support; real-time feedback that analyzes real-time data from a surgery; postoperative monitoring and analysis; analyze postoperative data to predict current patient outcomes and identify factors that contribute to successful surgeries or reduced complications; continuous learning and improvement; data analysis for datasets of surgical procedures to identify one or more of: patterns, trends, and best practices; development of robotic surgical systems 22 that continuously learn and adapt based on the experiences and feedback from various surgical procedures.

In various embodiments, the programmed instructions 67 of surgical computing device 151 use historical procedure data selected from one or more of: historical patient data; historical data; and historical healthcare professional data associated with a plurality of instances of the surgical procedure; execute stored programmed instructions 67 of surgical computing device 151 to update the machine learning model based on a patient data and patient outcome data generated following execution of the surgical procedure according to a surgical plan; use one or more of direct Monte Carlo sampling; stochastic tunneling; and parallel tempering to optimize a predictor equation; generate anatomy data pre-operatively from medical image data of the anatomy of a patient; generate an intra-operative with a plurality of recommended actions associated with a surgical plan; evaluate a result of an execution of a recommended actions; update one or more inputs based on the evaluation to alter another one of the recommended actions to be executed subsequent to the one of the recommended actions; and update one or more inputs based on one or more deviations to recommended actions.

In one embodiment, a non-transitory computer readable includes programmed instructions 67 of surgical computing device 151 for improved surgical planning using machine learning. This can include executable code that, when executed by one or more processors 62, causes the one or more processors 62 to: train a machine learning model based on an artificial neural network and historical case log data sets including historical outcome data correlated with one or more of historical patient data, or historical healthcare professional data associated with a plurality of instances of a surgical procedure; where the artificial neural network includes a plurality of input nodes and downstream nodes coupled by connections having associated weighting values; applies a machine learning model to current patient data for a current patient to generate a predictor equation for a surgical result or outcome; instructs robotic surgical system 10 to implement one or more portions of a surgical procedure according to a surgical plan; and updates the machine learning model based on current patient data and current outcome data generated for the current patient following execution of the surgical procedure. This data is aligned across modalities—video, force sensors, imaging, and biometric signals—for model training and real-time contextual correlation.

In one embodiment, the non-transitory computer readable medium uses weighting values and includes a predictor equation coefficient, wherein the executable code, when executed by the one or more processors 62, further causes the one or more processors 62 to use one or more of: Monte Carlo sampling; stochastic tunneling; and parallel tempering to optimize a predictor equation.

In one embodiment, the executable code, when executed by the one or more processors 62, further causes the one or more processors 62 to: provide input data comprising signals that correspond with the input nodes to the artificial neural network as seeding data, wherein the input data is extracted from the historical case log data sets; and alters the weighting values until the artificial neural network is configured to provide a result that corresponds with the historical outcome data. This data is aligned across modalities—video, force sensors, imaging, and biometric signals—for model training and real-time contextual correlation.

In one embodiment, the executable code, when executed by the one or more processors 62, further causes the one or more processors 62 to provide one or more of: obtain a sensitivity threshold value; and apply a sensitivity threshold value to disregard one or more of the input nodes. In one embodiment, the executable code, when executed by the one or more processors 62, further causes the one or more processors 62 to generate anatomy data pre-operatively from medical image data of an anatomy of the current patient.

In one embodiment, the executable code, when executed by the one or more processors 62, further causes the one or more processors 62 to provide one or more of: generation of an intra-operative algorithm with a plurality of recommended actions associated with the surgical plan; evaluate a result of an execution of one of the recommended actions; and update one or more inputs to the intra-operative algorithm based on the evaluation to alter another one of the recommended actions to be executed subsequent to the one of the recommended actions, wherein the one or more inputs are updated based on one or more deviations to the one of the recommended actions In one embodiment, a method for improved surgical planning is provided that trains at least one machine learning model based on one or more of: historical case log data sets including historical outcome data correlated with one or more of historical patient data; historical surgical data; historical healthcare professional data associated with a plurality of instances of a surgical procedure; applies machine learning to current patient data; and updates the machine learning model based on the current patient data and current outcome data generated for the current patient following execution of the surgical procedure according to the surgical plan. In one embodiment, the machine learning model includes an artificial neural network, wherein the artificial neural network has a plurality of input nodes and downstream nodes coupled by connections having associated weighting values. This data is aligned across modalities—video, force sensors, imaging, and biometric signals—for model training and real-time contextual correlation.

In one embodiment, each weighting value may include a predictor equation coefficient. A sensitivity threshold value is then obtained and applied to disregard one or more of the input nodes. As a non-limiting example, input data includes signals that correspond with the input nodes to the artificial neural network as seeding data, wherein the input data is extracted from the historical case log data sets. As a non-limiting example, weighting values are altered until the artificial neural network is configured to provide a result that corresponds with the historical outcome data. This data is aligned across modalities—video, force sensors, imaging, and biometric signals—for model training and real-time contextual correlation.

In one embodiment, a method, executed by robotic surgical system 10, intraoperatively monitors a surgical procedure being performed on a patient by surgical robot. One or more processors 62 executes intraoperative data that describes the surgical procedure based on the monitoring. The one or more processors 62 extract one or more features from the intraoperative data. The intraoperative data is at least one physiological condition of the patient during the surgical procedure. One or more surgical tools are positioned and used during the surgical procedure. A planned surgical step is planned to use a machine learning model of robotic surgical system 10. The planned surgical step is based on the features and a machine learning model trained based database 6161 of historical data describing previous surgical procedures and is responsive to the confidence score being less than a threshold. The one or more processors 62 generate a prompt for a surgeon to intervene, when required, in the surgical procedure. The surgical robot 20 control is given to the surgeon for manually controlled operation of the surgical robot 20 for completion of the planned surgical step. In response to completion of the planned surgical step, one or more subsequent surgical steps are autonomously performed on the patient using the surgical robot. In responsive to the confidence score being greater than the threshold, the surgical robot 20 performs the surgical step. The one or more processors 62 determines if the surgical procedure is complete. In one embodiment live surgical procedures are monitored by robotic surgical system 10. The machine learning mode can be trained, by the one or more processors 62, while the live surgical procedures are being performed.

In one embodiment, training the machine learning model includes: generating, by the one or more processors 62, a prediction for a next surgical step performed by a previous surgeon in a previous surgical procedure based on the historical data describing previous surgical procedures; and comparing, by the one or more processors 62, the prediction to an actual next surgical step performed by the previous surgeon in the previous surgical procedure. As a non-limiting example, the comparing for training is by a regression model of robotic surgical system 10. In one embodiment, virtual robotic surgical procedures are based on the historical data describing previous surgical procedures for training the machine learning model to direct the surgical robot.

In one embodiment, the one or more processors 62 receive an indication from the surgeon for the surgical robot 20 to continue with the surgical step. The one or more processors 62 determine whether the surgical procedure is complete. Live surgical procedures can be monitored. The one or more processors 62 train by the machine learning model based on the live surgical procedures while the live surgical procedures are being performed. In one embodiment, the machine learning model is trained by generating, by the one or more processors 62, a prediction for a next surgical step performed by a previous surgeon in a previous surgical procedure based on the historical data describing previous surgical procedures.

The prediction is compared, by the one or more processors 62, to an actual next surgical step performed by the previous surgeon in the previous surgical procedure. The comparison uses a regression model of robotic surgical system 10. In one embodiment, in responsive to receiving the indication that overrides by the confidence score, the surgical step is performed.

In one embodiment, the surgical procedure being performed can be halted on the patient in responsive to the confidence score being less than the threshold. In one embodiment, The surgical robot 20 monitors activity of the surgeon during the surgical procedure. A notification can be provided indicating tremors of the surgeon associated with the activity or mental or physical fatigue. The notification can include a request for the surgeon to hand off control of the surgical procedure to another surgeon or the surgical robot. Detection utilizes embedded haptic sensors and motion analytics to isolate tremors and trigger stabilization modes or handoff prompts. Wearable sensors and monitoring devices can collect data during surgery to provide objective, continuous assessment of the surgeon's physical and mental state including heart rate variability (HRV), eye-tracking for attention and focus, and electromyography (EMG) for muscle fatigue. Surgical robots and simulators can track performance indicators such as task completion time, error rates, smoothness of hand or tool movement, and economy of motion. Declines in these metrics can indicate increased fatigue, both cognitive and physical.

In one embodiment, robotic surgery system 10 includes a non-transitory computer-readable storage medium storing computer programmed instructions 67 of surgical computing device 151. The medium storing computer programmed instructions 67 of surgical computing device 151 cause the robotic surgical system 10 to: monitor, by robotic surgical system 10, a robotic-assisted surgical procedure being performed on a patient by surgical robot 20 generates intraoperative data that describes the surgical procedure. One or more features are extracted from the intraoperative data. A confidence score is determined, and a planned surgical step uses a machine learning model of the robotic surgical system 10. The planned surgical step to be performed by the surgical robot 20 is based on the features. The machine learning model can be based on historical data describing previous surgical procedures. In responsive to the confidence score being less than a threshold, a prompt can be generated for a surgeon to intervene in the surgical procedure. The one or more computer processors 62 determine whether the robotic-assisted surgical procedure is completed, based on at least a portion of the intraoperative data of the patient indicating a condition of the patient. In responsive to determining the robotic-assisted surgical procedure has been completed, the robotic-assisted surgical procedure is determined.

When the confidence score is greater than the threshold, the surgical step can be performed. The computer programmed instructions 67 of surgical computing device 151 can cause robotic surgical system 10 to: monitor live surgical procedures; and train the machine learning model based on the live surgical procedures while the live surgical procedures are being performed. In one embodiment, the computer programmed instructions 67 of surgical computing device 151 trains the machine learning model cause to: generate a prediction for a next surgical step performed by a previous surgeon in a previous surgical procedure based on the historical data describing previous surgical procedures; and compare the prediction to an actual next surgical step performed by the previous surgeon in the previous surgical procedure, resulting in training a regression model of robotic surgical system 10. In one embodiment, the computer programmed instructions 67 of surgical computing device 151 causes robotic surgical system 10 to perform virtual robotic surgical procedures based on historical data describing previous surgical procedures for training the machine learning model to direct the surgical robot.

As a non-limiting example, the computer programmed instructions 67 of surgical computing device 151 can cause robotic surgical system 10 to: receive an indication from the surgeon for the surgical robot 20 to continue with the surgical step; responsive to receiving the indication, override the confidence score, and perform, by surgical robot, the surgical step.

In one embodiment, the computer programmed instructions 67 of surgical computing device 151 further cause robotic surgical system 10 to: monitor, by the surgical robot, activity of the surgeon during the surgical procedure; generate, by the one or more processors 62, a notification indicating tremors of the surgeon associated with the activity, the notification including a request for the surgeon to hand off control of the surgical procedure to the surgical robot. Detection utilizes embedded haptic sensors and motion analytics to isolate tremors and trigger stabilization modes or handoff prompts.

In one embodiment, a computer-implemented method extracts features from intraoperative data describing a surgical procedure being performed on a patient by a surgical robot; determining a confidence score and a planned surgical step using a machine learning model based on the features, the planned surgical step to be performed by a surgical robot, the machine learning model trained based on historical data describing previous surgical procedures; and responsive to the confidence score being less than a threshold, generating a prompt for a surgeon to intervene in the surgical procedure; after generating the prompt for the surgeon, receiving input from the surgeon for the planned surgical step; determining whether to override the confidence score based on the input from the surgeon; and in responsive to determining to override the confidence score, autonomously performing, by the surgical robot 20 the planned surgical step; and responsive to determining not to override the confidence score, transferring surgical robot 20 control to the surgeon for manual operation of the surgical robot 20 to robotically perform the planned surgical step.

In one embodiment, the computer-implemented method, in responsive to the confidence score being greater than the threshold, performs, by the surgical robot, the surgical step. As a non-limiting example, the computer-implemented method: monitored live surgical procedures; and trains the machine learning model based on the live surgical procedures while the live surgical procedures are being performed. In one embodiment, the machine learning model is trained to: generates a prediction for a next surgical step performed by a previous surgeon in a previous surgical procedure based on the historical data describing previous surgical procedures; and compares the prediction to an actual next surgical step performed by the previous surgeon in the previous surgical procedure, the comparing for training a regression model. In one embodiment, the computer-implemented performs virtual robotic surgical procedures are performed based on the historical data describing previous surgical procedures for training the machine learning model to direct the surgical robot. As a non-limiting example, AI execution, output, results, information, mathematical equations, and the like are seen at display 628, In one embodiment, a control cable 110 couples the computer 151 of surgeon console 12 with patient console 16, to control the surgical system 12, including the remote controllable equipment arms 54 and surgical instruments. A control cable 111 is coupled computer 151 and patient console 16 and surgeon's console 12, providing control of arms 54 and surgical instruments 18 through patient console 16.

Figure 1B:
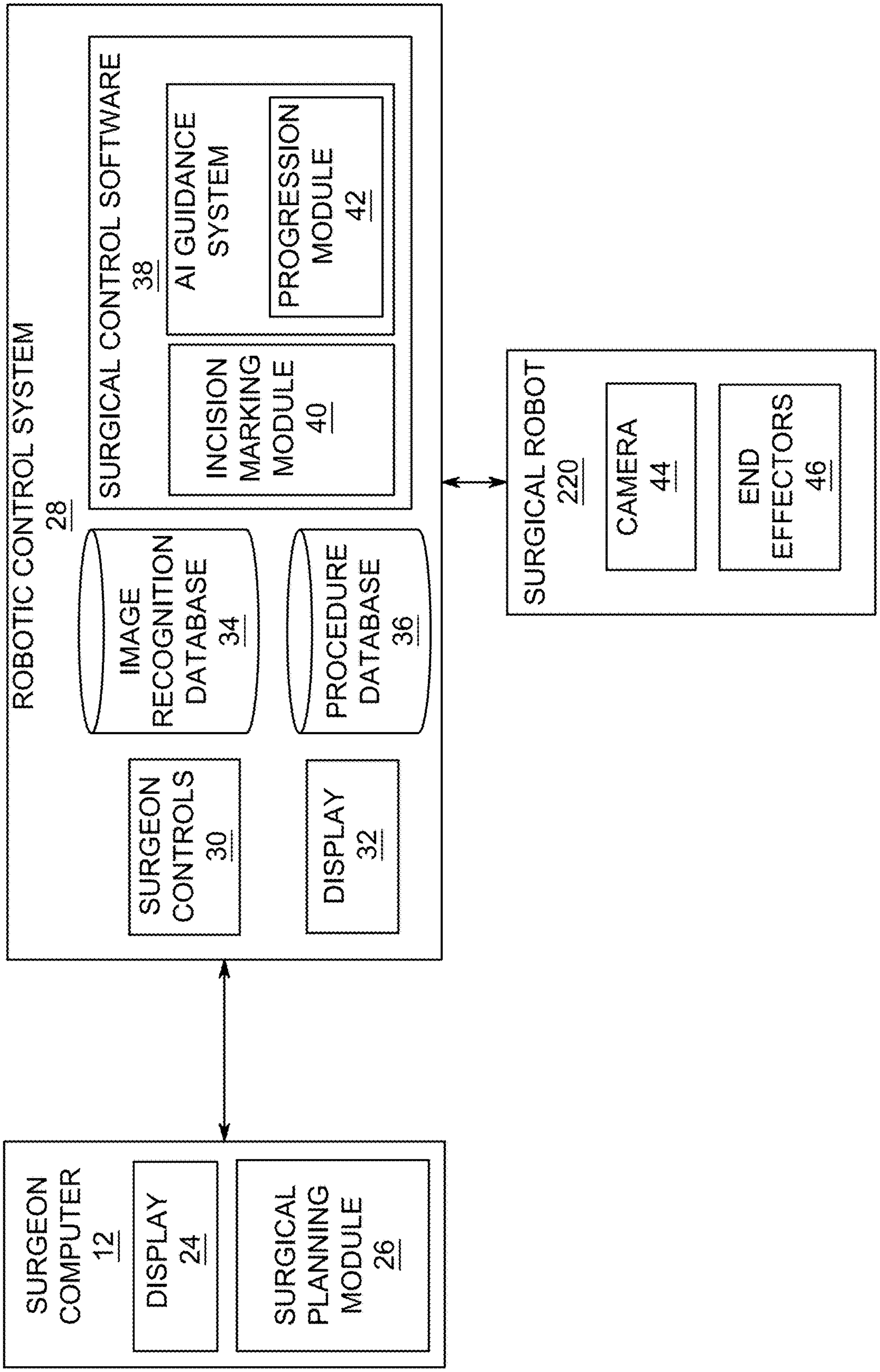
FIG. 1B illustrates one embodiment of a robotic surgery system with artificial intelligence of the present invention.
Figure 1C:
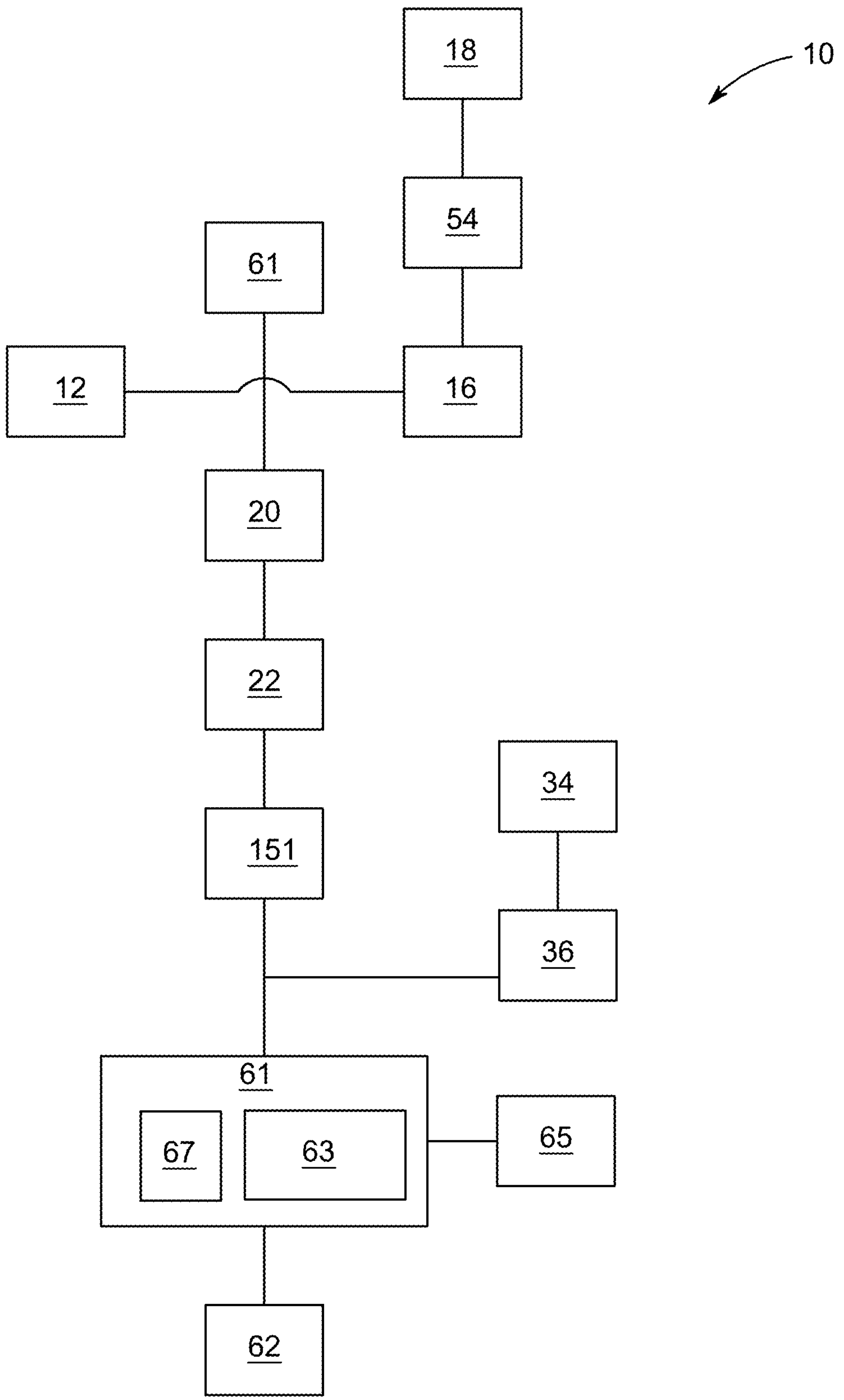
FIG. 1C illustrates another embodiment of a robotic surgical system of the present invention.

In various embodiments, robotic surgery control system 22 can use images obtained prior to and/or during surgery to guide surgical instruments 18, end effector 48, and the like. In one embodiment, an endoscope can be used. Endoscope 58 (hereafter "Visualization Device (VD)") can constantly interact with an anterior-posterior (AP) view, allowing a surgeon to be constantly looking at Visualization Device (VD) 58. This system can be expanded to cover the entirety of the surgical procedure. Using Visualization Device (VD) 58 allows for locating Visualization Device (VD) 58 inside of the patient as an additional reference point for the surgical navigation program. The configuration of Visualization Device (VD) 58 can be selected based on the instrument to move delivered over FIG. 1B illustrates one embodiment of a robotic surgical system 10. In one embodiment, surgeon console 12 includes a display 24, a planning module 26. Planning module 26 allows the surgeon to create a plan for a robotic surgery procedure. The plan can be created by a various of different methods. In one embodiment, surgeon console 12 is coupled to a robotic surgical system 10. Robotic surgery control system 22 can include one or more of: surgeon controls 30, a display 32 (24), an image recognition database 34, a procedure database 36, surgical control software 38, an incision module 40, an artificial intelligence ("AI") system 42 with a progression module 44. Surgical robot 20 can include a camera 46 and end effectors 48. As a non-limiting example, a variety of algorithms can be used with AI system 42 including but not limited to: supervised learning; classification and regression; decision tree; random forest; support vector machines; Naïve Bayes; linear regression; logistic regression; enhanced imaging; image recognition; treatment planning; risk assessment; robot-assisted navigation; path planning; collision avoidance; autonomous robotics; steady hand assistance; intraoperative decision support; real-time feedback; alert and warning; postoperative monitoring and analysis; prediction; patient outcomes: continuous learning and improvement; data analysis; and the like, as more fully set forth below.

As non-limiting example, system 10 can include a plurality of modules including but not limited to: forecasting, alert, regulatory compliance, pre-selection, personalization, explainability, simulation, data acquisition, control, feedback, calibration, data management, imaging, deviation, logging, behavior, dashboard, interference, conventual, conflict resolution, complier, learning, adaption updated, similarity, procedure, predictive, computer vision, orchestration, post production, visualization training, hyperspectral imaging, data acquisition, resection guidance, motion compensation, AI system, adaption control, analytics, and the like, (hereafter collectively element no, “111”.

It will be appreciated that one or more databases, such as database 61, can be included, as set forth herein.

As a non-limiting example, procedure database 36 can include medical records data, images (e.g., pre- and post-surgical images), physician input, sensor data, and the like. The images can include MRI or CAT scans, fluoroscopic images, or other types of images. The sensor data can be collected during procedures, and the like. related to all procedures of this type. Databases 34 and 36 can be queried by surgical control 30 or all medical imaging from the current patient and by progression module 36 for data for all similar patients who had the same procedure.

Image recognition database 34 can include images taken by surgical robot cameras 46 that are defined by the surgeons and updated with each use of robotic surgical system 10 for greater accuracy. As a non-limiting example, surgeon controls 30 can be used manual manipulation of surgical robot 20, either to take over when the AI cannot proceed or to navigate the end effector 48.

As a non-limiting example, robotic surgical system 10 utilizes incision marking module 40 for determining patient position. Optionally, an incision site can be marked AI system 42 is then initiated.

As a non-limiting example, AI system 42 can use 244 to take an image of the point of interest and progression module 42 compares the image received from camera 46 to image to the image recognition database 34 to determine if the tissue present is the desired tissue type that will allow surgical robot 20 to proceed. In one embodiment, progress through a tissue type is displayed based on the number of layers of the current tissue removed as compared to the average number of layers removed in other patients who had the same procedure with a same amount of anatomical volume at the same surgical point of interest.

In one embodiment, an imaging system and progression module 36 are initially trained using a neural network/machine learning. Using machine learning systems which construct algorithms that can learn from and then make predictions on the image data. Image data-driven predictions can be made by building a mathematical model from image input data. The image data can be used for the final model which usually comes from multiple datasets, including but not limited to A trained dataset may be built; real-time images may be used with robotic surgical system 10. As tissues are identified, the tissue types can be annotated virtually over the real-time images, with a percent probability of identification.

In one embodiment, robotic surgical system 10 allows the surgeon to stop the process. Stopping the process may include a teaching step in which the surgeon defines the tissue type visible, to improve the functionality of the image recognition database 34 software.

Historical data of many surgeries can include information relative to the amount of time (video) and the virtual identified images on a tissue. In one embodiment, a sequence of image-recognized tissue (and the timing of getting to and through these recognized tissues) is compared to the historical database. When the real-time recognized tissues are correlated with the same sequence of tissues in the historical database, robotic surgical system 10 then can proceed. When a recognized tissue does not appear in the sequence history, or if the recognized tissue appears earlier than expected, an alert is provided As non-limiting examples, end effectors 48 can include retractor tubes and surgical hardware, in addition to the incision markers, removal of 18, skin/muscle fascia incision instruments 18. If a new end effector 48 is needed, the surgeon or support staff makes the hardware adjustment before robotic surgical system 10 proceeds to the next step in the pre-operative plan. Robotic surgical system 10 returns to AI system 42 until the next surgical step is completed. This process continues to loop until the procedure is complete.

Figure 2:
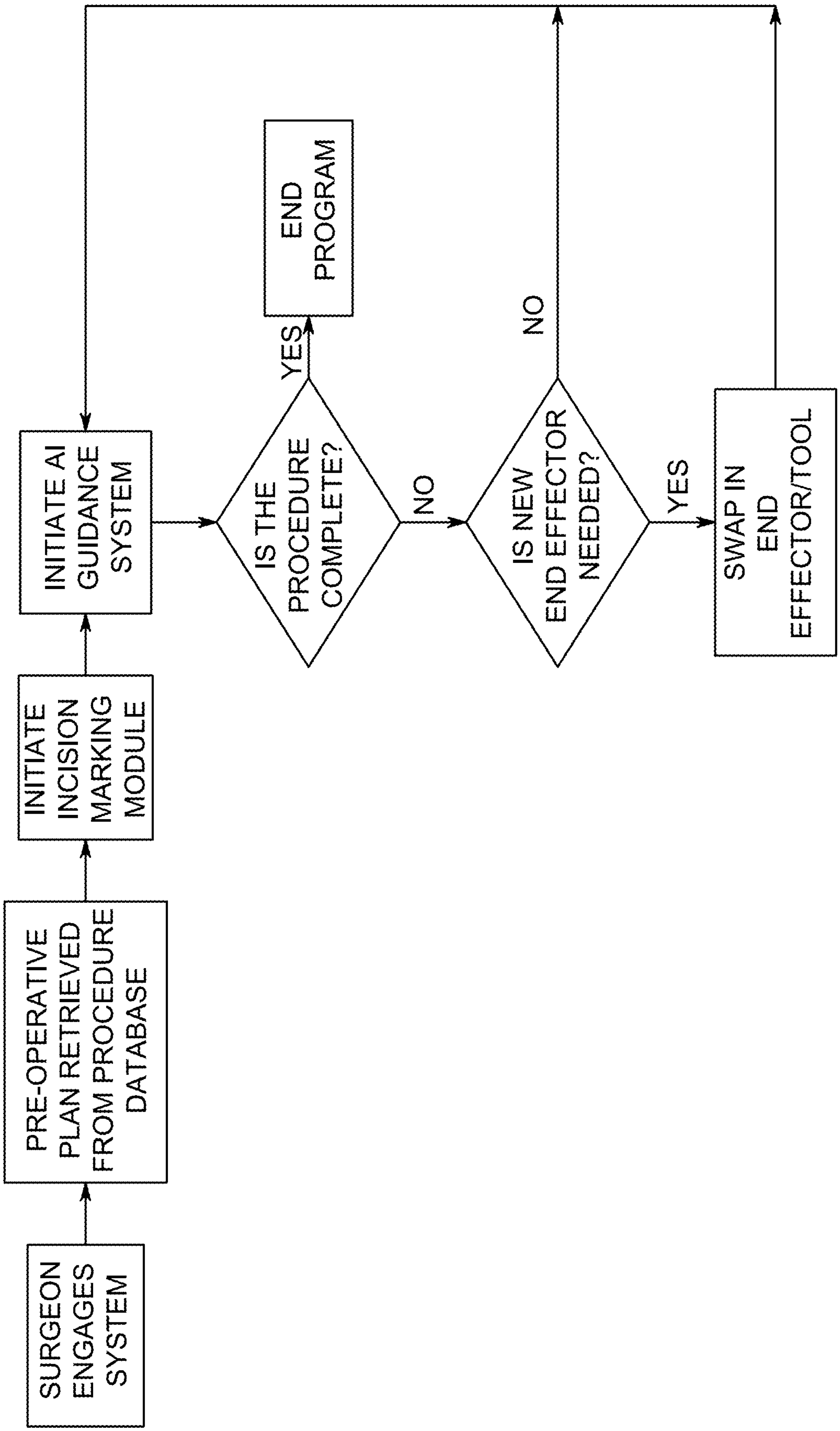
FIG. 2 illustrates one embodiment of a surgical control software module of the present invention.

FIG. 2 is a flow chart illustrating one embodiment of surgical control software 38. In one embodiment, the pre-operative plan, can be retrieved from the procedure database 36. In one embodiment, robotic surgical system 10 uses a series of prompts in preparation for surgery. As a non-limiting example, robotic surgical system 10 provide a guidance setup with visual and auditory feedback to the surgeon and assistants at a tele-operational assembly touch-pad interface, as well as feedback on a console touchscreen interface, described hereafter, providing access of guidance information from a variety of locations within the operating room.

Figure 3:
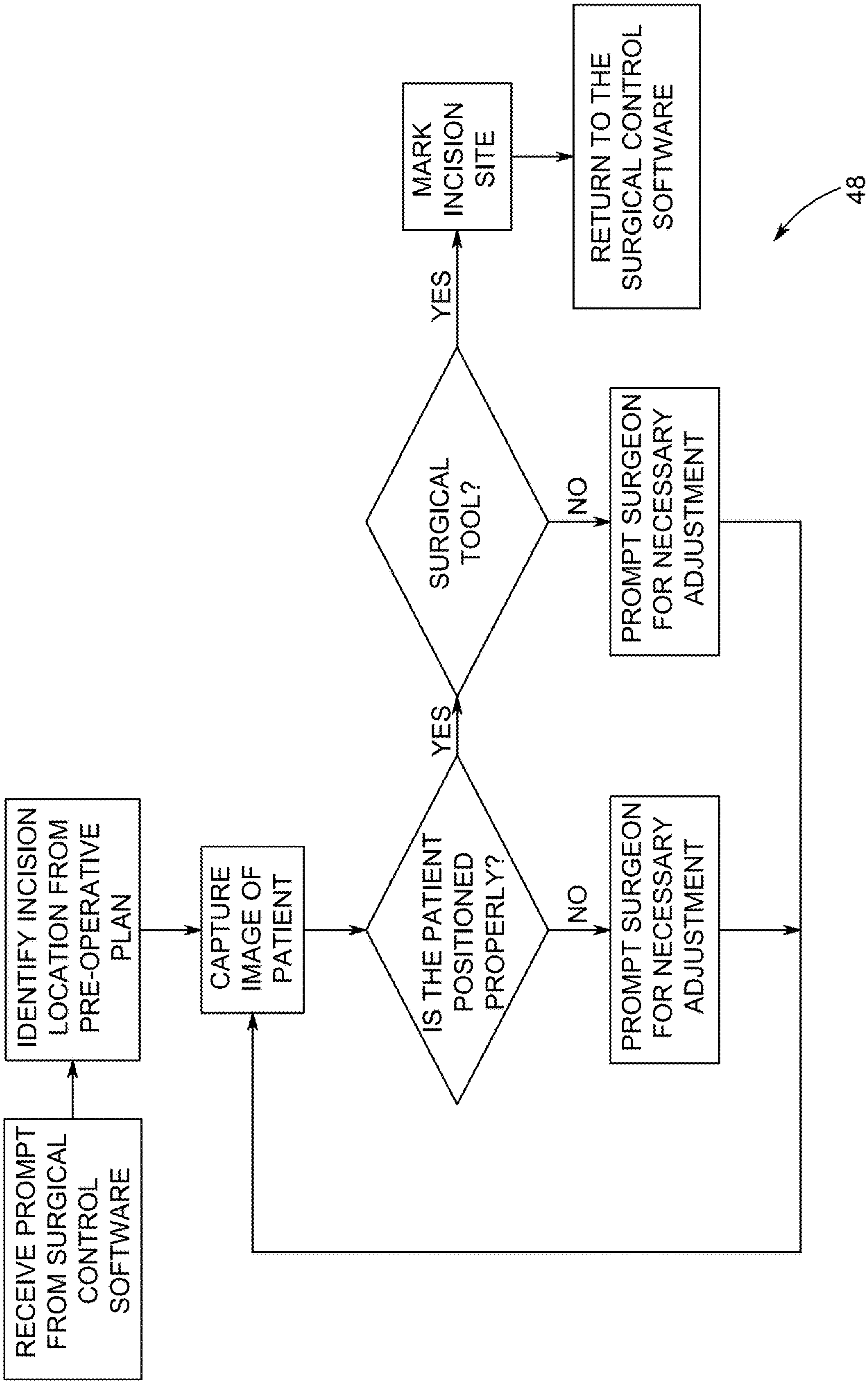
FIG. 3 illustrates one embodiment of an incision marking module of the present invention.

In one embodiment, shown in FIG. 3, an embodiment of an incision marking module 40 that is part of the surgical control software 38. Module begins 40 when it receives a prompt from surgical control software 38. As a non-limiting example, module 40 can capture an image of the patient to determine if they are properly positioned on the operating table. If not, the surgeon or support staff are prompted for the necessary adjustment and a new image is captured. This loop continues until robotic surgical system 10 is satisfied that the patient is properly positioned. Placement of a surgical instrument 18 is checked by imaging system. This process loops in the same way as the patient positioning is looped. The surgeon and/or assistants are prompted for the necessary adjustment to guide the surgical tube, and another image is taken until the robotic surgical system 10 is satisfied that the surgical instrument 18 is properly placed.

Figure 4:
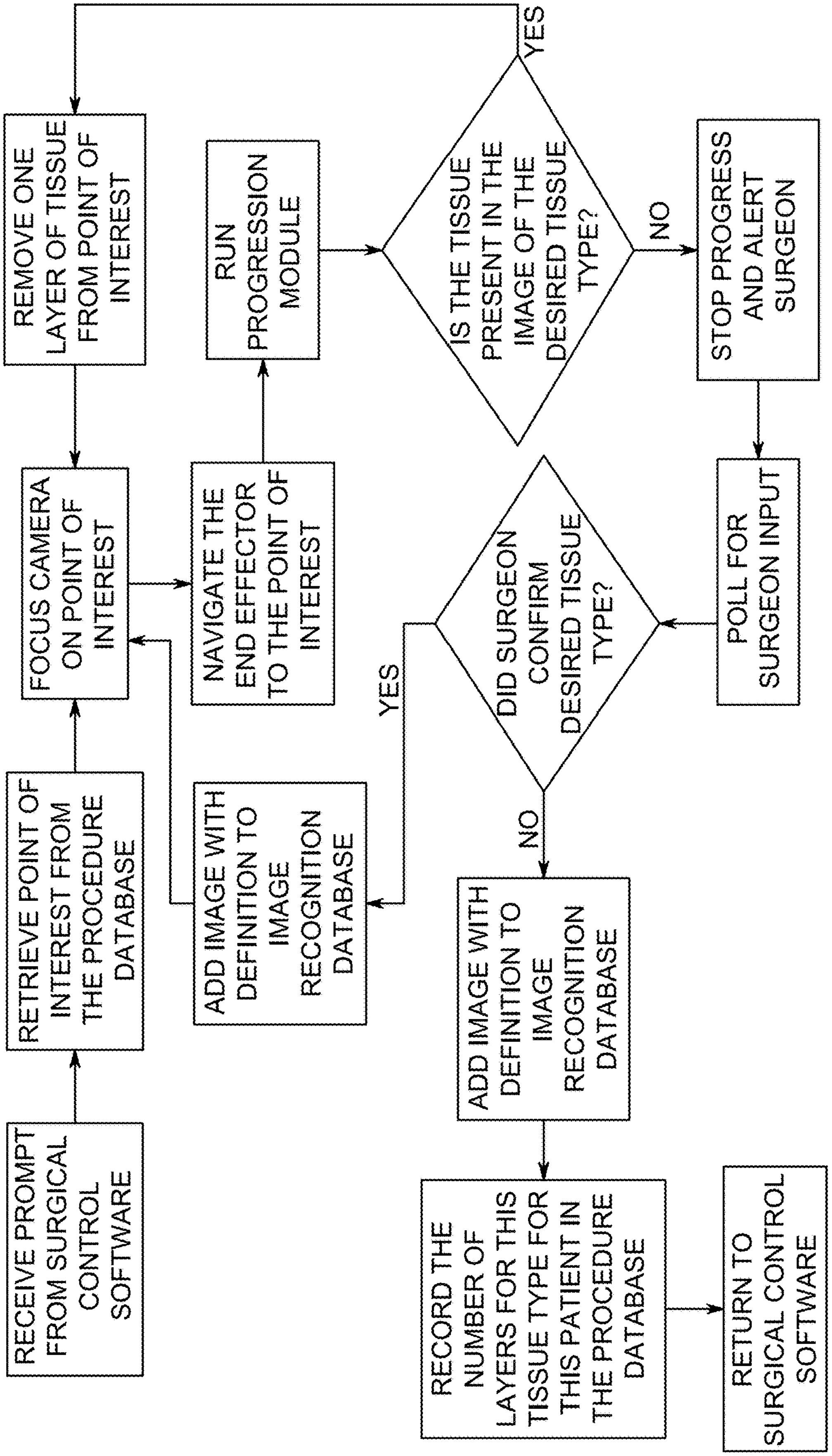
FIG. 4 illustrates one embodiment of an artificial guidance system of the present invention

As a non-limiting example AI system 42 is shown in FIG. 4.

As a non-limiting example, as shown in, AI system 42 is illustrated. In one embodiment, AI system 42 triggers progression module 36 when imaging robotic surgical system 10 and the end effectors 48 are at the point of interest on the current patient AI system 42 includes AI engine 65, as more fully set forth below.

In one embodiment, AI engine 65 takes in a description of a problem and how one would go about teaching concepts covering aspects of the problem to be solved, and AI engine 65 compiles the coded description into lower-level structured data objects that a machine can more readily understand, builds a network topology of the main problem concept and sub-concepts covering aspects of the problem to be solved, trains codified instantiations of the sub-concepts and main concept, and executes a trained AI model 706 containing one, two, or more neural networks.

In one embodiment, AI engine 65 can abstract away and automate the low-level mechanics of AI. AI engine 65 can manage and automate much of the lower-level complexities of working with AI. Each program developed in the pedagogical programming language can be fed into AI engine 65 to generate and train appropriate intelligence models.

AI engine 65 can abstract generation of a neural network topology for an optimal solution and faster training time with a curriculum and lessons to teach the neural network via recursive simulations and training sessions on each node making up the neural network.

In one embodiment, AI engine 65 can contain a vast array of machine learning algorithms, has logic for picking learning algorithms and guiding training, manages data streaming and data storage, and provides the efficient allocation of hardware resources. AI engine 65 is implemented with infrastructure that supports streaming data efficiently through the system. AI engine 65 can use a set of heuristics to make choices. The set of heuristics also make it possible for AI engine 65 to choose from any number of possible algorithms, topologies, and the like.

An image of the point of interest is taken and an Image recognition engine using database 34 identifies the tissue type present in the image taken of the point of interest on the current patient. As a non-limiting example, image recognition database 34 identifies the tissue type and to store the definitions of tissue types found in images as they are defined by surgeons using robotic surgical system 10.

Figure 6:
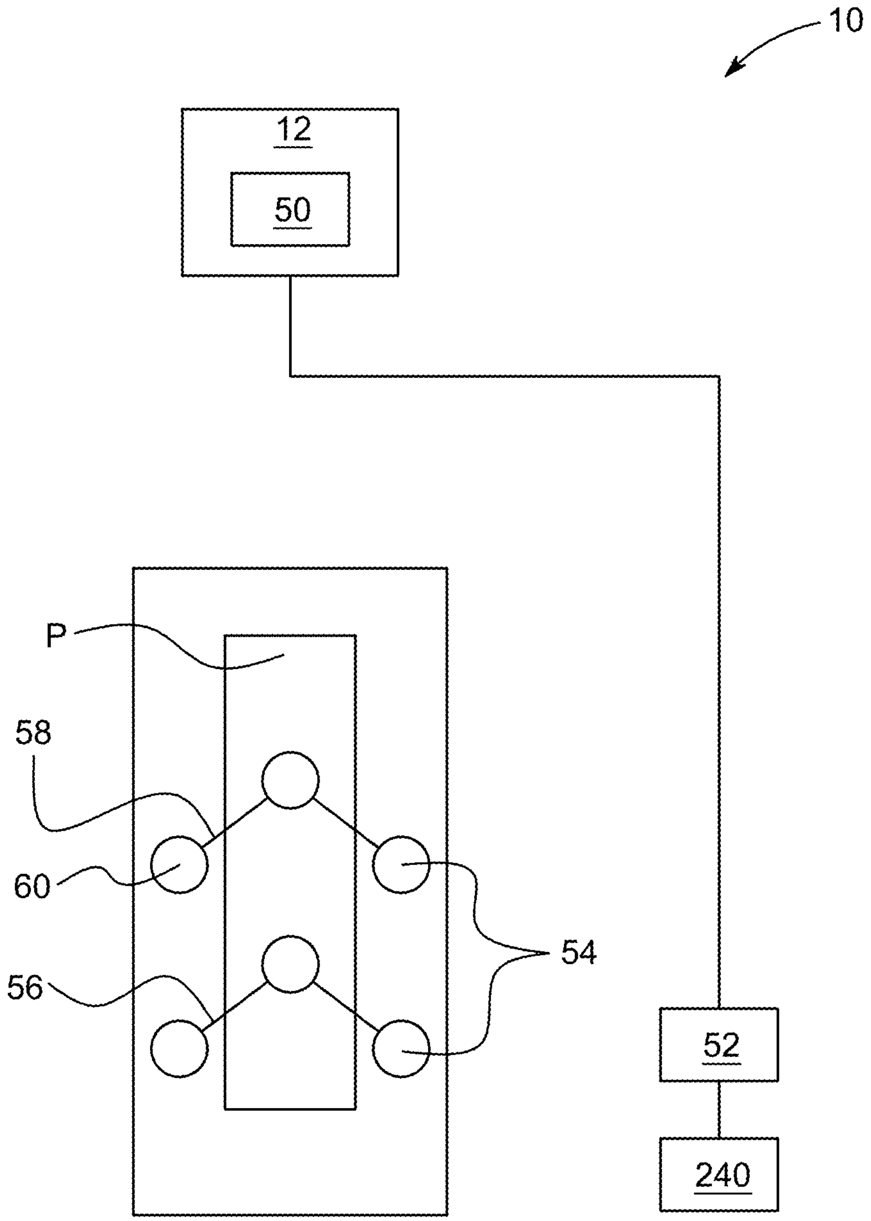
FIG. 6 illustrates one embodiment of a block diagram of a first robotic surgery system to perform robotic surgical procedures of the present invention.
Figure 7:
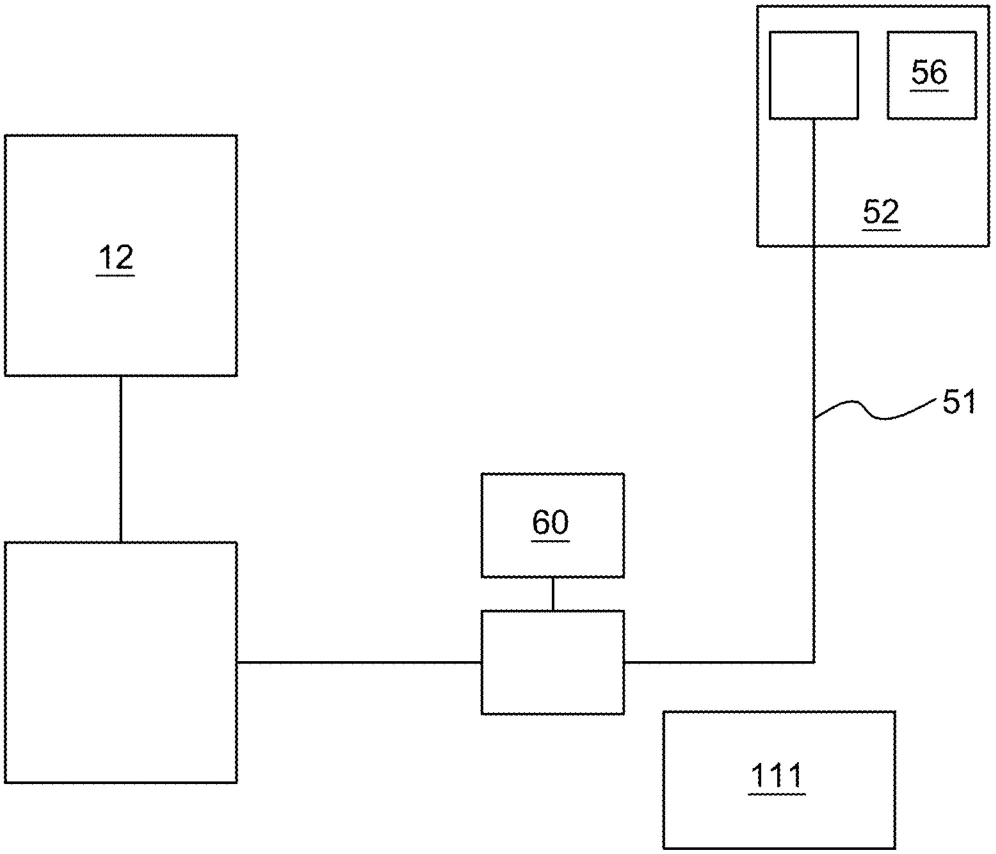
FIG. 7 illustrates one embodiment of a block diagram of a second robotic surgery system to perform robotic surgical procedures of the present invention.
Figure 8:
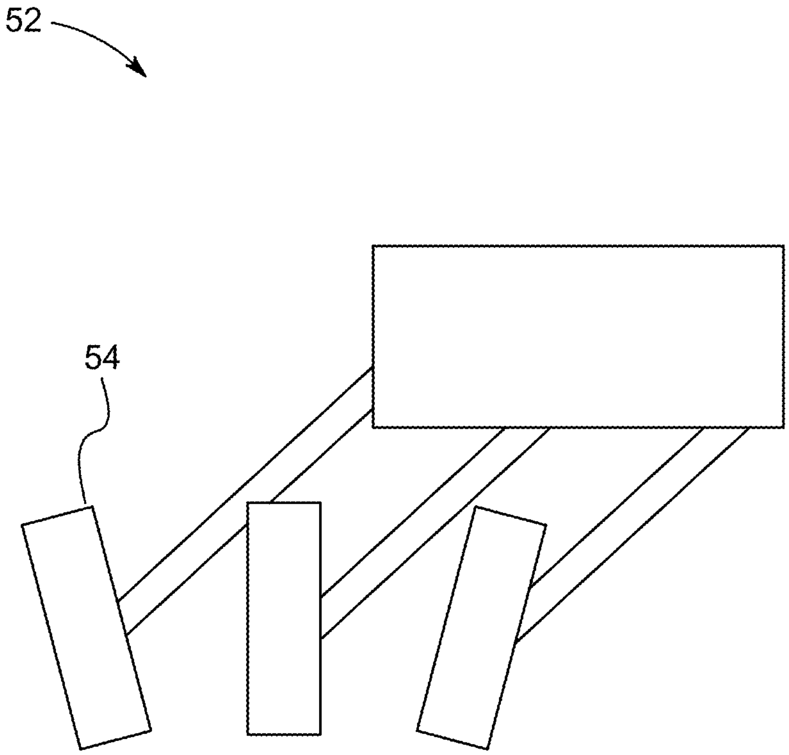
FIG. 8 illustrates one embodiment of a robotic surgical manipulator with a plurality of robotic surgical arms of the present invention.

As a non-limiting example, illustrated in FIGS. 6 through 8, a surgeon, designated as O performs surgical procedures on patient P by manipulating input devices at the surgeon console 12. In one embodiment, a computer 151, described hereafter, of console 12 directs movement of robotically controlled endoscopic surgical instruments 18, causing movement of instruments 18 using the robotic surgical manipulator, e.g., the patient console 16.

In one embodiment, computer 151 includes one or more processors 62 that interpret movements and actuation of master controllers, (and other inputs the surgeon and assistant, to generate control signals that can control surgical instruments 18 at the surgical site. As a non-limiting example, computer 151 and vision console 240 map the surgical site into the controller so it feels and appears to the surgeon operator that the master controllers are working over the surgical site.

As a non-limiting example, viewer vision console 240 has one or more displays 24 where images of a surgical site are viewed. In one embodiment, a viewer is provided that includes left and right display devices. In one embodiment, a three-dimensional perspective is provided, with the viewer including stereo images for each eye including a left image and a right image of the surgical site including any robotic surgical in a left viewfinder and a right viewfinder. The display devices 24 can be pairs of cathode ray tube (CRT) monitors, liquid crystal displays 24 (LCDs), or other type of image display devices 24 (e.g., plasma, digital light projection, etc.). In one embodiment, the images are provided in color by a pair of color devices 452 L, 452 R (24); such as color CRTs or color LCDs.

In one embodiment, patient console 16 has one or more robotic arms 54, including three or more that can be supported by linkages, with a central arm 54 supporting an endoscopic camera 56 (46) and the robotic surgical arms 54 to left and right of center supporting tissue manipulation surgical instruments 18.

As a non-limiting example, patient console 16 includes robotic arms 54 and instruments, and is positioned alongside patient table. In one embodiment, the has four arms 54, and robotic instruments 18 with articulating joints near the tip that allow for wristed movement. As a non-limiting example, this can provide a number of degrees of freedom of movement for surgical tasks, including but not limited to suturing, dissection. A variety of different robotic instruments 18.

In one embodiment, robotic surgical system 10 includes a plurality of robotic arms 54, such as four robotic arms 54 coupled to a mount of the patient console 16. In one embodiment, a Visualization Device (VD) 58, described in greater detail hereafter, is coupled to any of the robotic arms 54 through a robotic trocar, providing optimized visualization of the surgical site. In one embodiment, the mount is used to provide laser targeting and improved anatomical access from almost any position In one embodiment, an assistant provides pre-positioning of patient console 16 relative to patient P as well as swapping surgical instruments 18 for alternative surgical instruments 18 while viewing the internal surgical site via an assistant's display 60. The image of the internal surgical site shown to A by the assistant's display 60 and surgeon O by surgeon's console 12 is provided by one of the surgical instruments supported by patient console 16. In one embodiment, robotic arms 54 include a positioning portion and a driven portion.

In one embodiment, the surgeon receives an image of an internal surgical site at display 24, and/or and assistant O by surgeon's console 12 is provided by one of the surgical instruments 18 supported by patient console 16. Real-time image recognitive can be used with end effectors 48 including, without limitation, robotic grippers 68 also known as (550), cutting instruments, (scalpels), cannulas, reamers, rongeurs, scissors, drills, bits, or the like. The degrees of freedom, sizes, and functionalities of end effectors 48 can be selected based on the procedure to be performed. For example, one end effector 48 can be used to cut and remove bone and another end effector 48 can be used to remove cartilage, discs, or the like. A variety of end effectors 48 can be used to perform a surgical procedure according to the surgical plan.

In one embodiment, robotic surgical system 10 takes an image of an area to be worked on in this step in the surgery and sends that image through an image recognition system with image recognition database 34. If the desired tissue type is identified by robotic surgical system 10, the progress through the surgical step may be calculated by comparing the number of layers of tissue affected by surgical robot 20 in the current procedure to the average number of layers affected to complete this surgical step in statistically similar patients who had the same procedure. That progress is displayed for the surgeon; the tissue is affected as prescribed in the surgical plan and the process repeats until the desired tissue type is not identified by the image recognition system with image recognition database 34. When the desired tissue type is not identified, surgical robot 20 stops its progress and the image is presented to the surgeon to define. If the surgeon defines the tissue as the desired type, the identified image library in the image recognition database 34 is updated and surgical robot 20 proceeds.

In some embodiments, system 10 obtains view, images of a selected site, which can be one or more images of a region of interest, and the images can be sent to image recognition system with image recognition database 34. The images can be still images or video. If a targeted tissue is identified by robotic surgical system 10, a surgical plan can be generated. The targeted tissue can be identified using a comparison image to reference images. The comparison can be used to identify tissue to be removed, determine when a procedure is completed, and the like.

In some embodiments, the targeted tissue can be identified by comparing the number of layers of tissue affected by surgical robot 20 in the current procedure to reference data (e.g., the average number of layers affected to complete this surgical step in statistically similar patients who had the same or similar procedure). That progress is displayed for the surgeon; the tissue is affected as prescribed in the surgical plan and the process repeats until the targeted tissue has been removed. The progress can stop the image is presented to the surgeon to define. If the surgeon defines the tissue as targeted tissue, the identified image recognition library in the image with image recognition database 34 is updated and the surgical robot 20 proceeds. This process can be applied to each individual step in the spinal surgery process as detailed herein.

As a non-limiting example, surgeon console 12 can include a viewer, including but not limited to Visualization Device (VD) 58, that can be a stereo viewer, with one or more sensors, as set forth below. In one embodiment, when the head is not positioned in the surgeon console 12, robotic surgical system 10 is deactivated and robotic arms 54 are locked in place. As a non-limiting example, the use of two master controllers provides that a surgeon's hand movements are processed by a computer 151 and sent to patient console 16. In one embodiment, patient console 16 controls the robotic instruments 18 inside the patient's body in real-time. Motion scaling can be performed to filter out physiologic tremor, allowing for finer movements. Each arm's 54 trajectory is dynamically refined by the AI engine 65 using probabilistic models that account for patient-specific anatomical deviations.

In one embodiment, processing by a computer 151 allows for intuitive motion. A movement of the surgeon's hands is translated to the movement of the instruments 18.

As a non-limiting example, adjustments to robotic surgical system 10, including but not limited to camera 46 control, scope setup, audio volume, console ergonomics, and the like, are made while the surgeon is seated at surgeon console 12. Surgeon console 12 can also toggle between robotic arms 54. In one embodiment, this is achieved with the use of surgeon console hand and foot pedal 68 controls, as more fully set forth below. As a non-limiting example, surgeon console 12 is connected to the vision console 240 and patient console components via cables. Each arm's 54 trajectory is dynamically refined by the AI engine 65 using probabilistic models that account for patient-specific anatomical deviations.

In some embodiments, robotic surgical system 10 includes a computer 151, computing system, for at least partially controlling robotic surgical apparatus 20 to perform surgical actions by obtaining a first image of a region of interest associated with a subject. A type of tissue shown in the first image can be identified based, at least in part, on a neural network model trained on an image training set. In response to determining that the identified type of tissue belongs to a set of targeted types, causing the robotic surgical apparatus 20 to perform a first surgical action with respect to the region of interest in accordance with a surgical plan. A second image of the region of interest can be obtained after completion of the first surgical action. Additionally surgical steps can be performed.

A computer-readable storage medium storing content that, when executed by one or more processors 62, causes the one or more processors 62 to perform actions including obtaining first image of a region of interest associated with a surgery subject, and identifying a type of tissue shown in the first image based, at least in part, on a neural network model. In response to determining that the identified type of tissue belongs to a set of targeted types, robotic surgical apparatus 20 performs a first surgical action with respect to the region of interest in accordance with a surgical plan. A second image of the region of interest is obtained after completion of the first surgical action. The actions can include displaying types of tissue comprises displaying one or more boundary indicators for indicating at least one of targeted tissue to be removed, protected tissue, delivery instrument 18 placement, or an end effector 48 working space within the subject.

In one embodiment, robotic surgical system 10 provides three-dimensional magnified with vision console 240. As a non-limiting example, a binocular telescopic camera 46 lens system is coupled to a high-resolution 3D HD camera 46, which can be Visualization Device (VD) 58 camera 46. As a non-limiting example, the two are held on the main robotic manipulator arm 54. In one embodiment, system 10 includes a Visualization Device (VD) 58 camera 46 with one or more digital image sensors positioned at a distal end of Visualization Device (VD) 58 camera 46. In one embodiment, digital image information is transmitted to one or more image processors. The binocular images are translated by computer 151 into a magnified 3D image when viewed at the surgeon console as a non-limiting example, the scope, Visualization Device (VD) camera 46 (58), can be 12 mm (Si) or 8 mm in diameter.

FIG. 7 illustrates robotic surgical system 10 and a method of utilizing AI to complete specific steps in a minimally invasive surgery, according to an embodiment.

Figure 9:
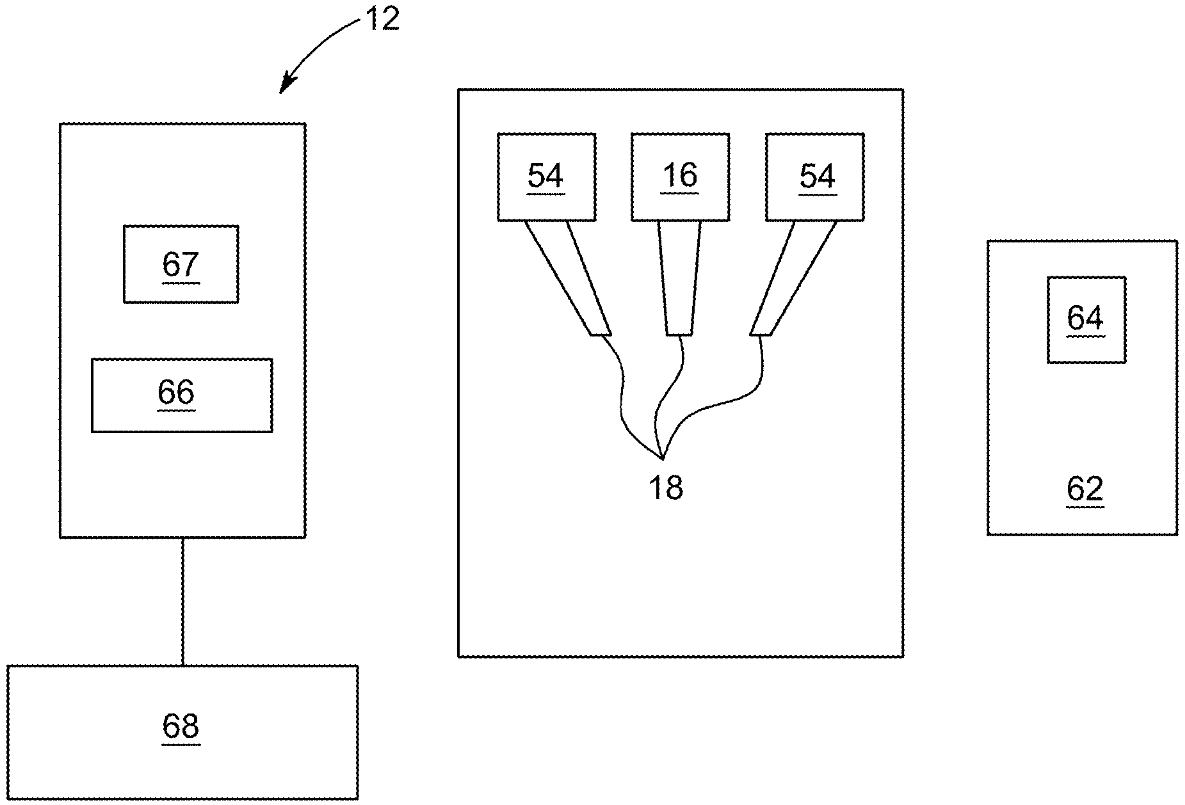
FIG. 9 illustrates one embodiment of a teleoperated surgical system of the present invention.

As a non-limiting example, illustrated in FIG. 9, signal(s) or input(s) are transmitted from surgeon console 12 as well as to one or more processors 62 at a surgeon console 12 and/or at control cart 64, which may interpret the input(s) and generate command(s) or output(s) to be transmitted to the patient console 16 to cause manipulation of one or more of surgical instruments 102 and/or patient side manipulators (arms) 54 which the surgical instruments 18 are coupled at the patient console 16, robotic surgical system 10 components in FIG. 9 are not shown in any particular positioning and can be arranged as desired, with the patient console 16 being disposed relative to the patient so as to affect surgery on the patient.

In one embodiment, surgeon console 12 receives inputs from a user, including but not limited to a surgeon or associate, by various input devices, including but not limited to, grippers 66 (550), such as gripping mechanisms 66 (550) and foot pedals 68, and serves as a master controller by which surgical instruments 18 mounted at the patient console 16 act as "slaves" to implement the desired motions of the surgical instrument(s) 18, and accordingly perform the desired surgical procedure. In one embodiment, grippers 66 (550) may act as master devices that may control the surgical instruments 18, which may act as the corresponding "slave" devices at the manipulator arms 54, and in particular control an end effector 48 and/or wrist of the instrument. In one embodiment, foot pedals 68 may be depressed to provide a variety of different actions, including but not limited to, suction, irrigation, etc.) at the instruments 18.

As a non-limiting example, output units may include a viewer or display 24, described in greater detail hereafter that allows the surgeon to view a three-dimensional image of the surgical site, including but not limited to during the surgical procedure, with Visualization Device (VD) 58 at patient console 16.

In one embodiment, surgeon console 12 includes input devices that a surgeon can manipulate to transmit signals to actuate surgical instruments 18 that can be mounted at arms 54 at the patient console 16. The surgeon console 12 can have output devices providing feedback to the surgeon. Surgeon console 12 can include a unit that integrates the various input and output devices, with, for example, a display 24, but also can include separate input and/or output devices that are in signal communication with the controllers, such as controllers provided at the surgeon console and accessible by a surgeon, although not necessarily integrated within a unit with various other input devices. As an example, input units may be provided directly at the surgeon console 12 and may provide input signals to a processor at the control cart. As a non-limiting example, surgeon console 12 does not necessarily require all of the input and output devices to be integrated into a single unit and can include one or more separate input and/or output devices.

Figure 10:
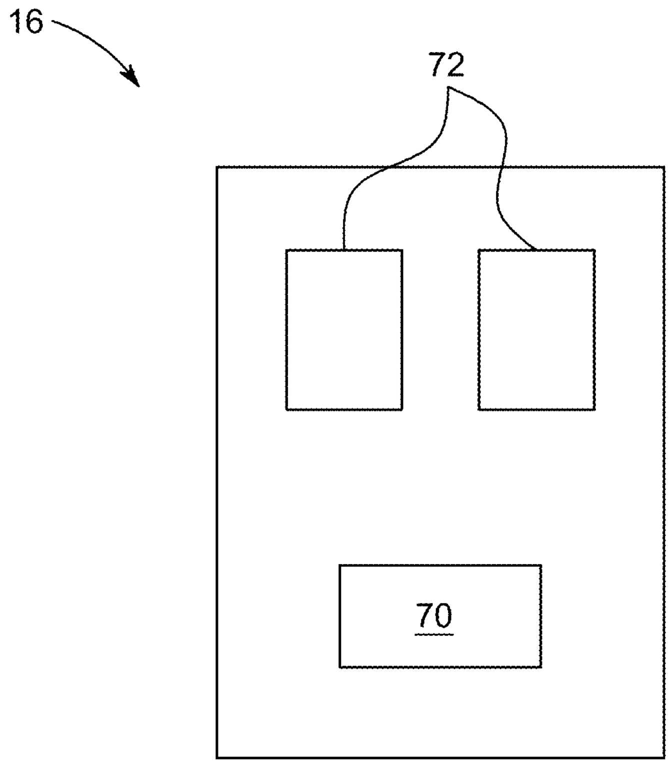
FIG. 10 illustrates one embodiment of a patient side cart that includes a steering interface of the present.

In one embodiment, patient console 16 can have a teleoperated surgical steering interface 70, FIG. 10. In one embodiment, steering interface 70 detects forces applied by surgeon or assistant to steering interface 70 that provides a signal to a controller of a drive system 80 of patient console 16, causing it to be driven and steered.

Steering interface 70 can be coupled to a rear of a patient console 16 with one or more manipulator arms 72. Information received at steering interface 70 can be by drive system 80 to provide motive force to one or more transportation mechanisms of patient console 16.

Figure 11:
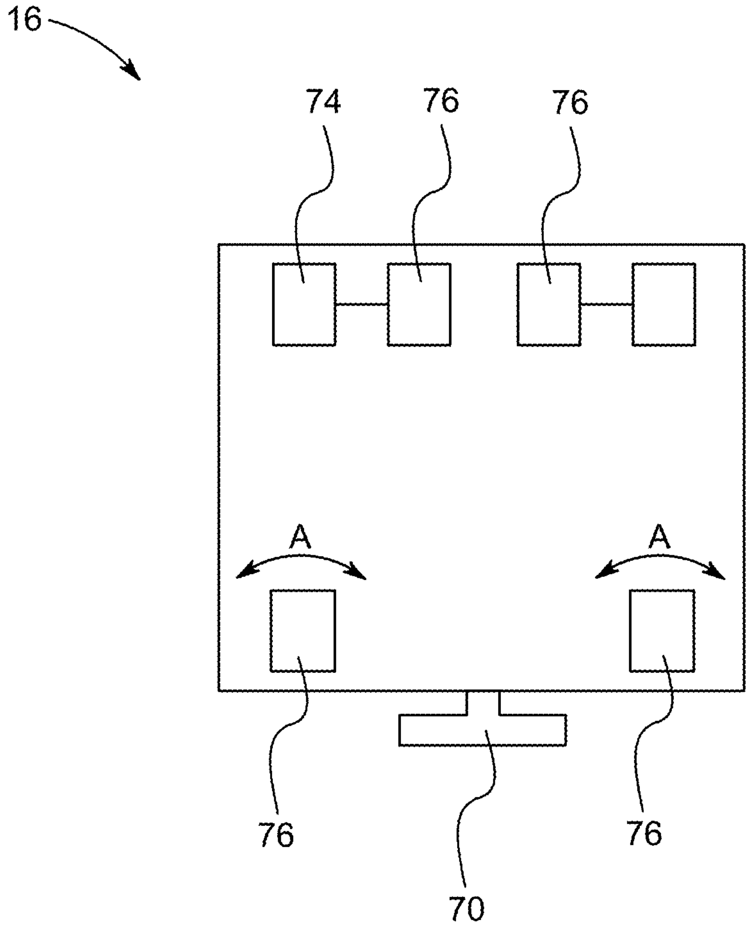
FIG. 11 illustrates one embodiment of a wheel arrangement of a patient side cart with a steering interface of the present invention.

Referring to FIG. 11, one or more wheels of a patient side cart 16 may be driven. In one exemplary embodiment, the front wheels 74 of a patient console 16 may be driven while rear wheels 76 are not driven. In one embodiment, driven wheels are individually driven by separate motors.

Figure 12:
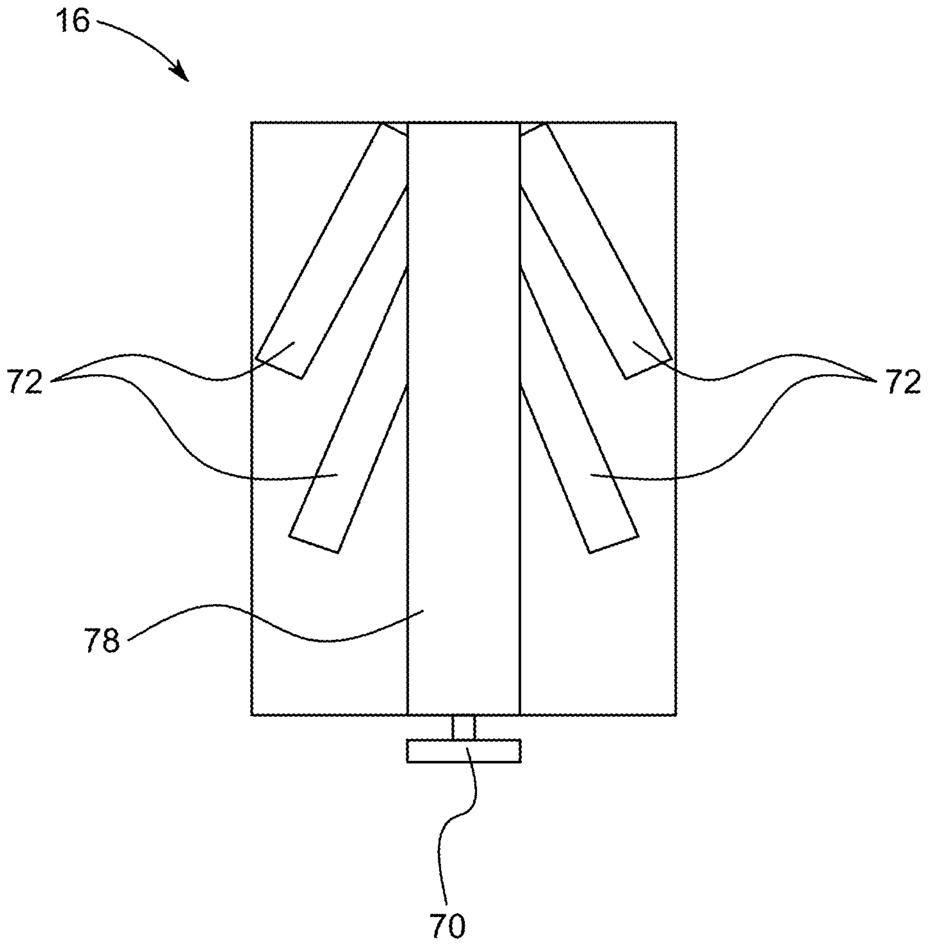
FIG. 12 illustrates one embodiment of a patient side cart in a stowed configuration of the present invention.

As illustrated in FIG. 12, patient control 16 includes steering interface 70 and a plurality of manipulator arms 72 that are configured to hold surgical instruments 18, tools, and the like. the manipulator arms 72 can be folded into a relatively compact arrangement toward a center of the patient console 15. As a non-limiting example, a post 78 where manipulator arms 72 can be positioned in a non-extended, compact configuration.

As a non-limiting example, patient console 16 includes a drive system 80 configured to receive signal(s) from steering interface 70. In one embodiment, steering interface 70 includes one or more sensors. Patient console 16 can include a control system or controller, which is part of the drive system 80 or a separate device or system in communication with the drive system. Robotic surgery control system 22 can be configured to receive signal(s) or input(s) from steering interface 70 of patient console 16. In response to received input(s), steering interface 70 can issue one or more command outputs or outputs to control the driven wheel(s) 76.

Figure 13:
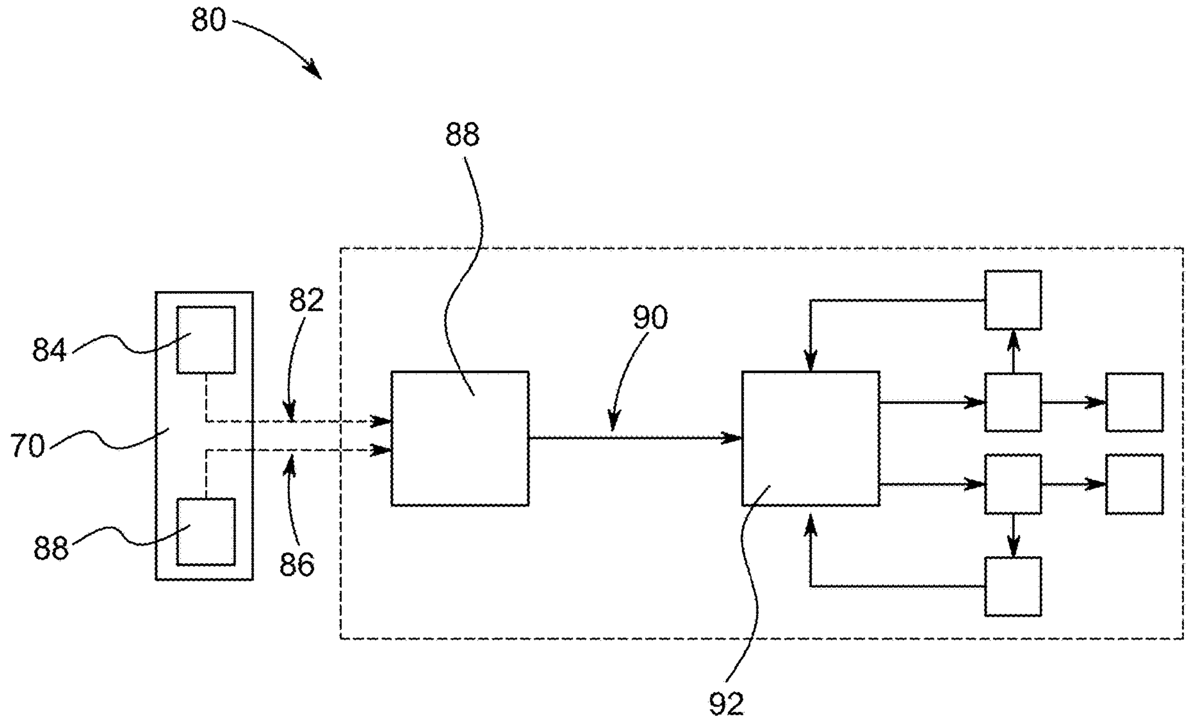
FIG. 13 illustrates one embodiment of a drive system for a patient side cart of the present invention.

Referring to FIG. 13, a drive system 80 for patient console 16 is shown in communication with a steering interface 70. Steering interface 70 transmits a first input or signal 82 from the first sensor 84 and a second input or signal 86 from a second sensor 88, which are received by the drive system 80.

Drive system 80 can include a signal conditioner 88 and one or more devices. As a non-limiting example, signal conditioner 88 includes an amplifier to increase the power of signals 82 and 86. Signal conditioner 88 can include an analog-to-digital converter to convert analog signals 82 and 86 to a digital form for further processing. As a non-limiting example, signal conditioner 88 includes these devices in combination with one another. Once signals 82 and 86 have been conditioned by signal conditioner 88, the signals are sent via a high-speed communication connection 90 to other components of the drive system 80. Drive system 80 can include a control system 94 or controller 92.

Figure 14:
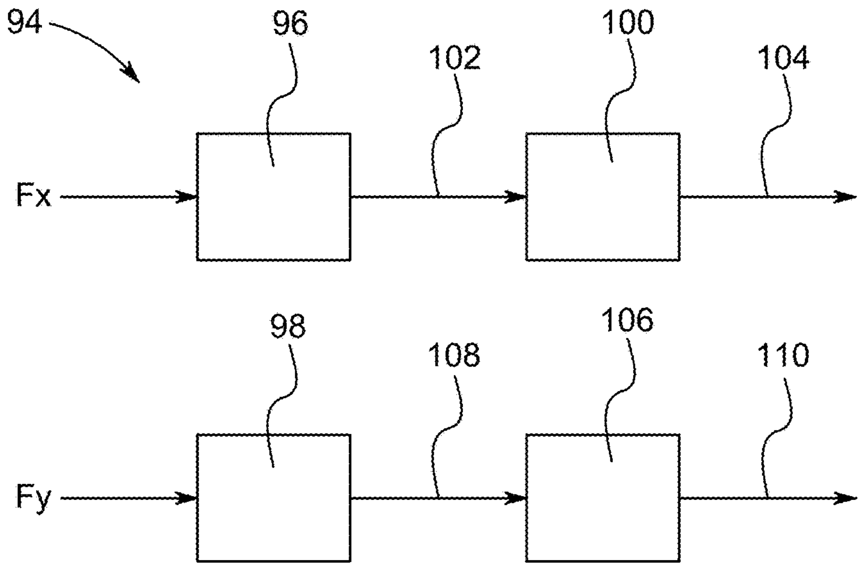
FIG. 14 illustrates one embodiment of a control system of a drive system for a patient side cart of the present invention.

In FIG. 14 illustrates a schematic block diagram of a control system 94 for drive system 80. As a non-limiting example, control system 94 receives one or more inputs or signals from steering interface 70. Control system 94 may include a first control module 96 and a second control module 98.

Control system 94 may include a fore/aft model section or module 100 configured to receive a desired raw fore/aft movement signal or input 102, analyze the signal, and issue or transmit a fore/aft command output 104 corresponding to the desired movement. Fore/aft command output 102 that is a command output to a motor to drive a driven wheel and produces a desired fore/aft movement. For instance, fore/aft command output 104 is in the form of a force or a torque command for a motor that drives a driven wheel. Control system 94 can include a yaw model section or module 106 to receive a desired raw yaw signal or input 108, analyze the signal, and issue or transmit a yaw rate command output 110 corresponding to the desired yaw rate for turning a patient side cart In one embodiment, a feedback portion of control system 94 measures output 108 of the driven components 98, such as a velocity, acceleration, and/or yaw rate. For example, a sensor may be configured to detect the velocity, acceleration, and/or yaw rate of one or more driven wheels or of patient console 16.

Figure 15:
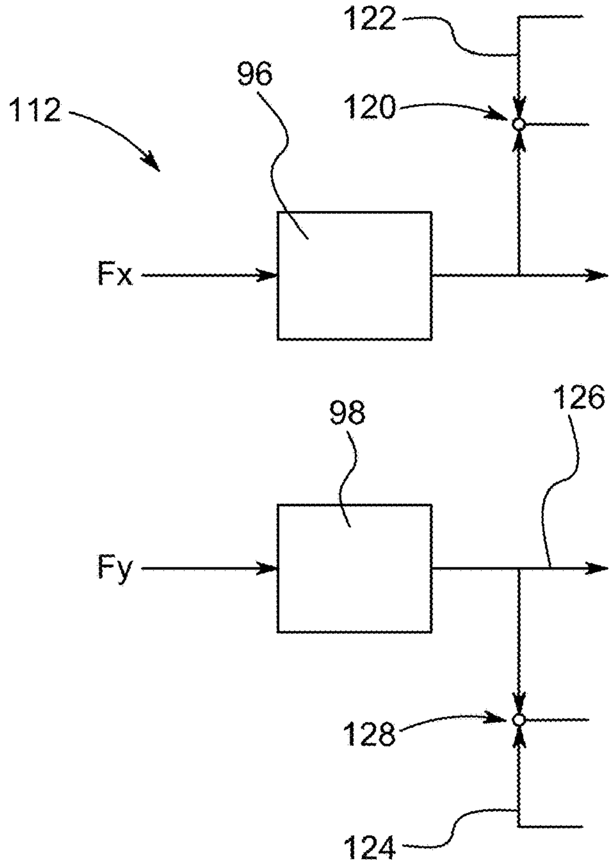
FIG. 15 illustrates one embodiment of another embodiment of a control system for a patient side cart that includes feedback control of the present invention.

FIG. 15 illustrates feedback control. Control system 112 can be used as control system 94 of FIG. 14. Feedback control output signals can be provided from patient console 16 to control system 94. As a non-limiting example, patient console dynamics section 114 can provide a fore/aft output signal 116 and a yaw rate output signal 118. Output signal 116 is compared with the desired fore/aft movement signal 120, such as at error detector 122, and yaw rate output signal 124 is compared with yaw rate signal 126, such as at error detector 122. Any differences resulting from the comparison at error detectors 122, 128 are sent to feedback control modules 130 and 132. Fore/aft feedback control module 130 produces a fore/aft feedback command output 134, which is combined with the fore/aft command output 136, such as at adder 138, to provide a corrected fore/aft command output 140, which is in turn sent to patient console section 114. Yaw feedback control module 132 produces a yaw rate feedback command output 142, which is combined with the yaw rate command output 144, such as at adder 146, to provide a corrected yaw rate command output 148 that is sent to cart dynamics section 114.

Figure 17:
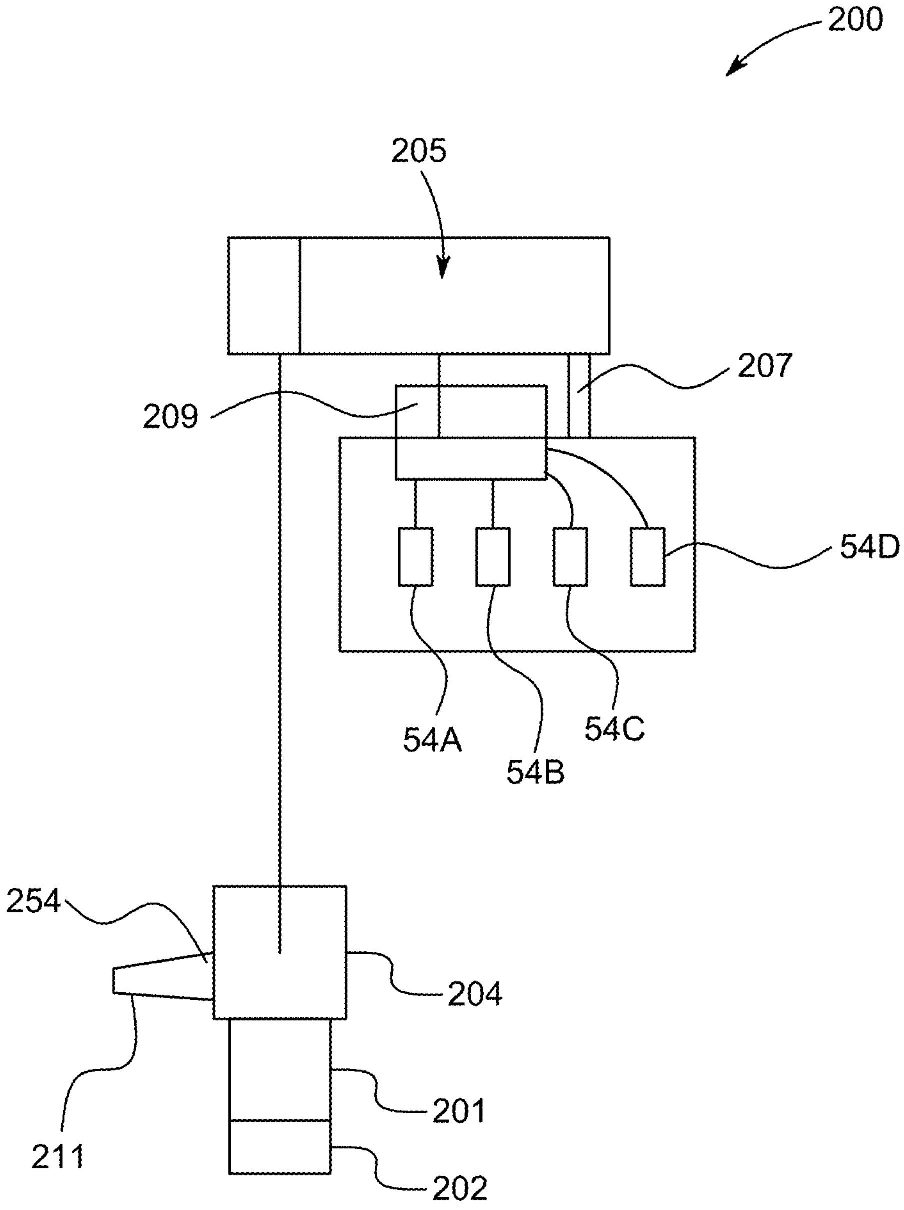
FIGS. 17, 18, 19 illustrate one embodiment of components that can be used with the FIG. 16 robotic surgical system of the present invention.
Figure 20:
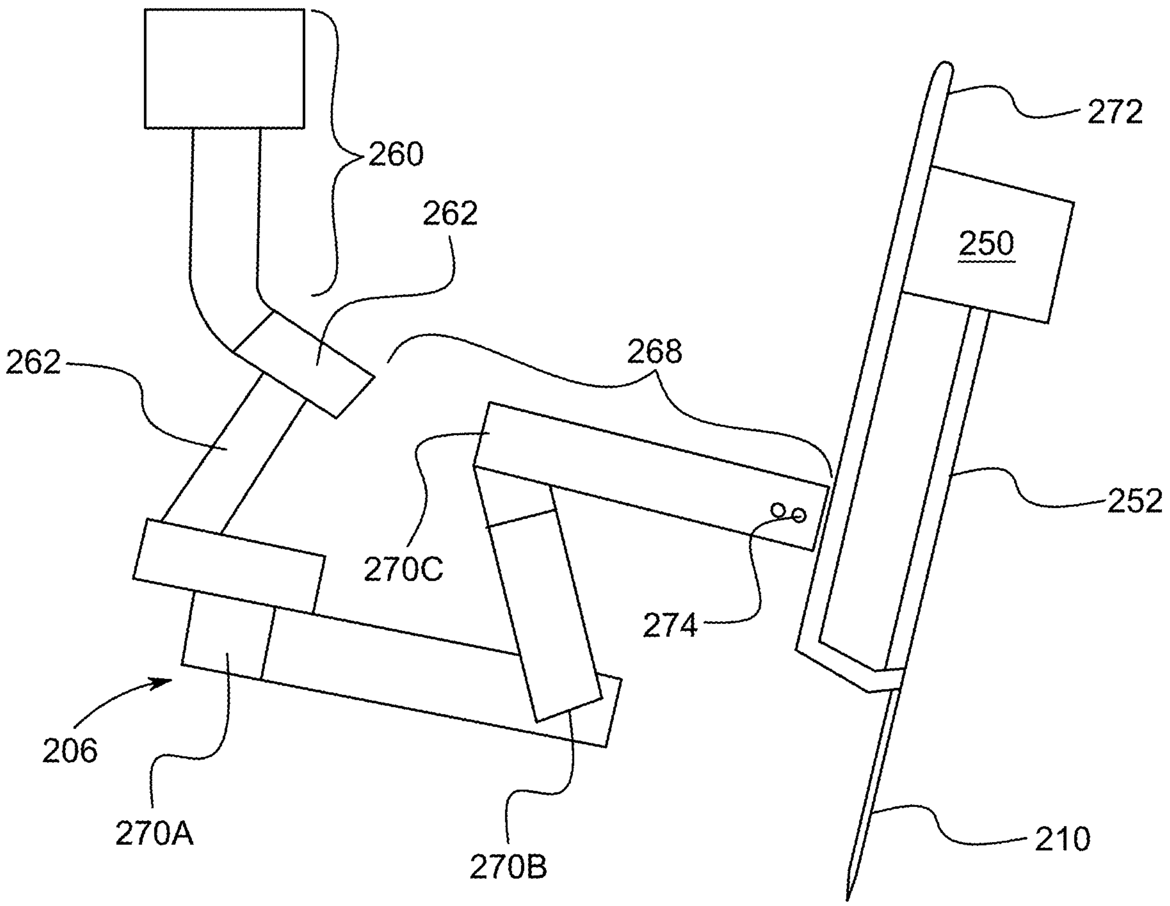
FIG. 20 illustrates one embodiment of an arm of a robotic surgical system of the present invention.

FIG. 20 illustrates an arm 54 of the robotic surgery robotic surgical system of FIG. 17 in one embodiment of the present invention.

Figure 19:
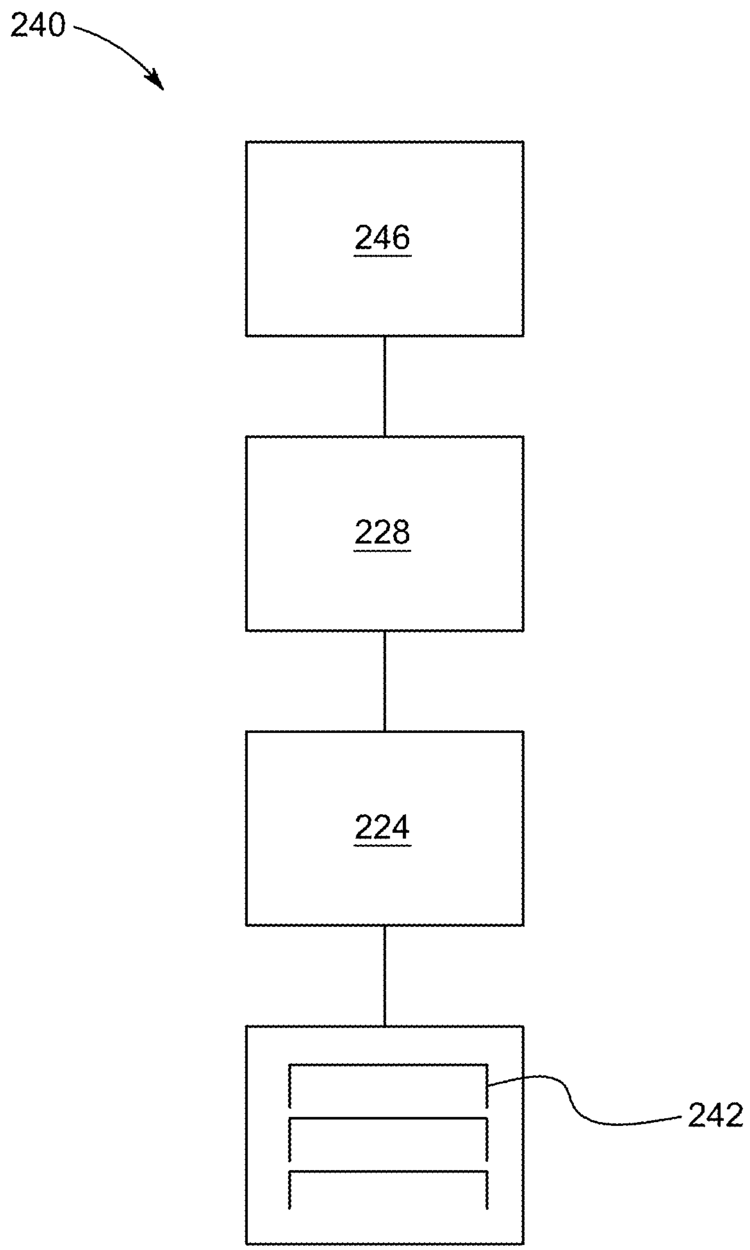

In one embodiment, as illustrated in FIG. 19, vision console 240 is part of robotic surgical system 10. The vision console 240 can house robotic surgical system's 10 central electronic data processing unit 242, which can be all or a portion of control system 250 (94), and vision equipment 244. In one embodiment, a central electronic data processing unit 222 includes much of the data processing used to operate robotic surgical system 10. In one embodiment, electronic data processing can be provided through surgeon console 12 and tele-operational assembly 200. As a non-limiting example, vision equipment 244 can include camera 46 control units for the left and right image capture functions of Visualization Device (VD) 58.

The vision equipment 244 may also include illumination equipment that provides illumination for imaging the surgical site. In one embodiment, vision console 240 includes an optional touchscreen monitor 246, which may be mounted elsewhere, such as on the assembly 200 or at patient console 16. In one embodiment, vision console 240 includes space 248 for auxiliary surgical equipment. As a non-limiting example, a teleoperated robotic surgical system 10 can include an intuitive telepresence for the surgeon.

In one embodiment, a control system 150 (94) is operatively linked to s touchpad, sensors, motors, actuators, encoders, hydraulic flow systems, and other components of the robotic surgical system 12. In one embodiment, robotic surgical system includes one or more teleoperational systems 200.

Figure 16:
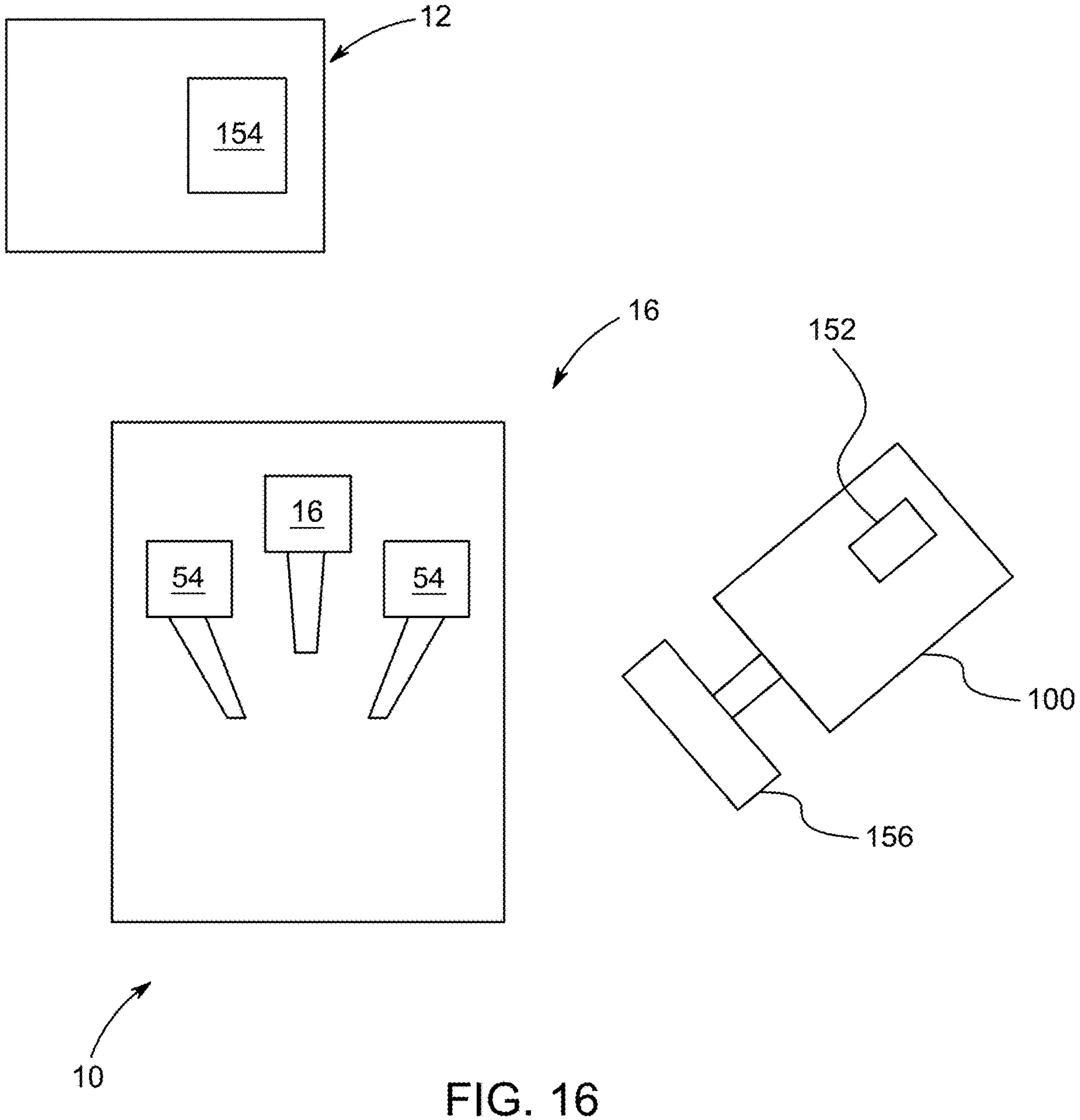
FIG. 16 illustrates one embodiment of a robotic surgical system of the present invention.

Referring to FIG. 16, control system 150, such as control system 94 of FIG. 14, includes one or more memories and processors 62, providing control between system 10, which can be tele-operational robotic surgical system 10, surgeon console 12, patient console 16 which provides surgeon input, image capture system 152 and a display system 154 (24). All are coupled together, which be by tele-operationally. As a non-limiting example, control system 150 can include programmed instruction, such as a computer-readable medium storing (instructions 67). While control system 150 is shown as a single contained element, robotic surgical system 10 can include two or more data processing circuits with one portion of the processing optionally being performed on or adjacent the teleoperational assembly 200. In one embodiment, centralized or distributed data processing architectures are used. As a non-limiting example, programmed instructions of surgical computing device 151 are provided as a number of separate programs or subroutines, or they may be integrated into a number of other aspects of the teleoperational systems 200. As a non-limiting example, control system 150 supports wireless communication protocols such as Bluetooth, IrDA, Home RF, IEEE 802.11, DECT, and Wireless Telemetry.

In one embodiment, robotic surgical system 10 includes a vision system 156 coupled with optical fiber communication links to surgeon console 12.

As a non-limiting example, control system 150 includes at least one memory and at least one processor (not shown) for effecting control between systems and elements of robotic surgical system 10. As a non-limiting example, control system 150 includes programmed instructions of surgical computing device 151 (e.g., a computer-readable medium storing instructions 67) to implement some or all of the robotic surgical system procedures and implementations. Programmed instructions of surgical computing device 151 can be provided with a number of separate programs or subroutines, or they may be integrated into a number of other aspects of robotic surgical system 10. As non-limiting examples, control system 150 supports wireless communication protocols such as Bluetooth, IrDA, HomeRF, IEEE 802.11, DECT, and Wireless Telemetry.

In one embodiment, control system 150 includes a surgeon or assistant interface configured to receive information from and convey information to a surgeon and assistants. As a non-limiting example, the surgeon or assistant interface can be a touchscreen monitor that may present prompts, suggestions, and status updates. In one embodiment, the touchscreen monitor is in a position in the operating room where it can be easily seen as the surgeon and assistants, in various embodiments, other interfaces can be used, including but not limited to: one or monitors or display screens 24, a keyboard, a computer mouse, rollers, buttons, knobs, and other user interfaces.

In some embodiments, control system 150 may include one or more servo controllers that receive force and/or torque feedback from the robotic surgical system 10.

In response to feedback, servo controllers transmit signals to surgeon and patient's consols 12 and 16, respectively. The servo-controller(s) can transmit signals instructing robotic surgical system 10 to move instruments 18. As a non-limiting example, any suitable conventional or specialized servo controller is used. The servo controller can be separate from, or integrated with, robotic surgical system 10.

In one embodiment, robotic surgical system 10 includes optional operation and support systems (not shown) such as illumination systems, steering control systems, eye tracking systems, fluid management systems such as irrigation systems and/or suction systems. In alternative embodiments, robotic surgical system 10 has more than one teleoperational assembly and/or more than one operator input system. The exact number of manipulator assemblies will depend on the surgical procedure and the space constraints within the operating room, among other factors. The operator input systems may be collocated, or they may be positioned, in separate locations. Multiple operator input systems allow more than one operator to control one or more manipulator assemblies in various combinations.

FIG. 17 illustrates one embodiment of a teleoperational assembly 200 (e.g., the teleoperational assembly 200 shown in FIG. 16. The assembly 200 includes an automated and motorized setup structure that supports projecting arms and may include a base 202 that rests on the floor, a telescoping support column 204 that is mounted on the base 202, a telescoping boom 205 that extends from the support column 204, and a platform portion as an orienting platform 207. The assembly 200 also includes support beams 209, and several arms 54 that support surgical (including portions of the image capture system 152). As shown in FIG. 17, arms 54(*a*), 54(*b*), 54(*c*), 54(*d*), such as arms 54, are instrument arms that support and move the surgical instruments used to manipulate tissue. One of these arms 54 may be designated as a camera 46 arm that supports and moves Visualization Device (VD) 58. shows one of the arms 54 with an interchangeable surgical instrument 210 mounted thereon. The surgical instrument may be Visualization Device (VD) 58 mounted on the arm 54 designated as the camera 46 arm. Visualization Device (VD) 58 may be a stereo Visualization Device (VD) 58 for capturing stereo images of the surgical site and providing the separate stereo images to the display system 24. In one embodiment, arms 54 that support surgical instruments 18 and the camera 46 may also be supported by a base platform (fixed or moveable) mounted to a ceiling or wall, or in some instances to another piece of equipment in the operating room (e.g., the operating table), two or more separate bases may be used (e.g., one base supporting each arm 54).

Figure 18:
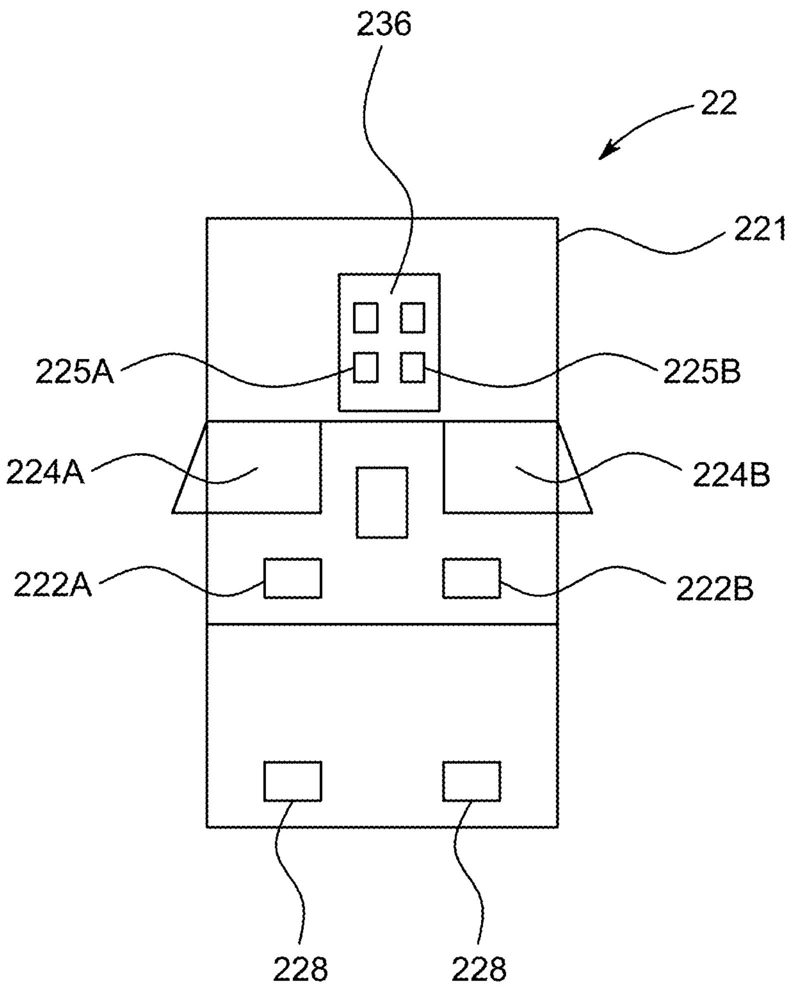

As is further illustrated in FIG. 20, instrument 200 includes an instrument interface 250 and an instrument shaft 252. In some embodiments, the teleoperational assembly 200 may include supports for cannulas that fix the instrument 210 with respect to the cannulas. In some embodiments, portions of each of the instrument arms 54 may be adjustable by personnel in the operating room in order to position the instrument with respect to a patient. Other portions of the arms 54 may be actuated and controlled by the operator at an operator input system 220 (as shown in FIG. 18. The surgical instrument 210 associated with each arm 54 may also be controlled by the operator at the operator input system 220.

In more detail, the arm 54 includes a vertical setup 260 connected via a setup joint 262 to a distal-most setup link 264. A yaw joint 266 connects the distal-most setup link 262 to a parallelogram pitch mechanism 268. The parallelogram pitch mechanism 264 includes a plurality of pitch joints 270(*a*), 270(*b*), 270(*c*) enabling it to move. A spar 272 connects to the parallelogram pitch mechanism 264 at a spar joint 274. Each of the setup joint 262, the yaw joint 266, the pitch joints 270(*a*), 270(*b*), 270(*c*), and the spar joint 274 are controlled by motors, referenced herein as a setup joint motor, a yaw joint motor, pitch joint motors, and a spar joint motor. Accordingly, the arm 54 is configured to move in a completely motorized fashion. In this embodiment, the motors are under the control of the control system 22 (94 and 150) and may be operated with motors of the other arms to take desired poses that may assist with draping, advancing over a patient, docking to surgical instruments, or storage, among others. In addition, encoders and sensors associated with each motor provide feedback to the control system 22 so that the control system senses or detects the position, status, and setup of the arm 54. In some embodiments, the spars 272 include sensors to detect the presence of surgical drapes on the arms 54.

The teleoperational assembly 200 also includes a helm 211 fixed relative to the base 202 on the support, column 204 with a user interface for controlling the setup and operation. In some embodiments, the user interface is a touchpad 254 capable of accepting user inputs and providing graphical, textual, auditory, or other feedback. The touchpad 254 provides features for teleoperational assembly 200 activities such as preparation for draping, docking, or stowing to help the user minimize the space it takes up in the OR. The touchpad 254 also provides a means for system fault notification and recovery. In some embodiments, the touchpad 254 is disposed along the support column 204 and is configured to be viewed by a user in the operating room, in other embodiments, the touchpad or other user interface is disposed elsewhere. It may be wired or wireless and may be disposed within bag or elsewhere for sterile use. The touchpad 254 in this embodiment is configured to display informational data relating to status of the teleoperational assembly 200, information relating to particular surgical procedures, and information relating to the overall teleoperational robotic surgical system 10. In some embodiments, the touchpad 254 is a touchpad display interface that presents information and accepts user inputs. As such, a user may input control instructions, including setup instructions, at the touchpad.

FIG. 18 is a front elevation view of an operator input system 220 (e.g., the operator input system 220 shown of FIG. 16. The operator input 220 includes a console 221 equipped with left and right multiple degree-of-freedom (DOE) control interfaces 222(*a*) and 222(*b*), which are kinematic chains that are used to control the surgical instruments 210 including Visualization Device (VD) 58. The surgeon grasps a pincher assembly 224(*a*), 224(*b*) on each of control interfaces 222, typically with the thumb and forefinger, and can move the pincher assembly to various positions and orientations. When a surgical instrument control mode is selected, each of control interfaces 222 is configured to control a corresponding surgical instrument and instrument arm 54. For example, a left control interface 222(*a*) may be coupled to control the instrument arm 54(*a*) and its associated surgical instrument 210, and a right control interface 222(*b*) may be coupled to the control instrument arm 54(*b*) and its associated surgical instrument 210. If the third instrument arm 54 *c* is used during a surgical procedure and is positioned on the left side, then left control interface 222(*a*) can be switched from controlling the arm 54(*a*) and its associated surgical instrument 210 to controlling the arm 54(*c*) and its associated surgical instrument 210. Likewise, if the third instrument arm 54(*c*) is used during a surgical procedure and is positioned on the right side, then the right control interface 222(*a*) can be switched from controlling arm 54(*b*) and its associated surgical instrument 210 to controlling the arm 54(*c*) and its associated surgical instrument 210. In some instances, control assignments between the control interfaces 222(*a*), 222(*b*) and combination of arm 54 surgical instrument 18, and combination of arm 54 and surgical instrument 18 may also be exchanged. This may be done, for example, if Visualization Device (VD) 58 is rolled 280 degrees, so that the instrument moving in the Visualization Device (VD)'s 58 field of view appears to be on the same side as the control interface the surgeon is moving. The pincher assembly is typically used to operate a jawed surgical end effector 48 (e.g., scissors, grasping retractor, and the like) at the distal end of a surgical instrument 210.

Additional controls are provided with foot pedals 228 (68). Each foot pedal 228 (68) can activate certain functionality on the selected one of instruments 210 (18). For example, foot pedals 228 (68) can activate a drill or a cautery surgical instrument 18 or may operate irrigation, suction, or other functions. Multiple instruments can be activated by depressing multiple ones of pedals 228 (68). Certain functionality of instruments 210 (18) may be activated by other controls.

As a non-limiting example, surgeon's console 12 also includes a stereo image viewer system 226 (e.g., the display system 24. Stereo image viewer system 226 includes a left eyepiece 225(*a*) and a right eyepiece 225(*b*), so that the surgeon may view left and right stereo images using the surgeon's left and right eyes respectively inside the stereo image viewer system 226. Left-side and right-side images captured by Visualization Device (VD) 58 (212) are outputted on corresponding left and right image displays, which the surgeon perceives as a three-dimensional image on a display system (e.g., the display system 24 shown in FIGS. 16 and (24). In an advantageous configuration, the control interfaces 222 are positioned below stereo image viewer system 226 so that the images of the surgical shown in display 24 appear to be located near the surgeon's hands below the display. This feature allows the surgeon to intuitively control the various surgical instruments in the three-dimensional display 24 as if watching the hands directly. In one embodiment, the servo control of the associated instrument arm 54 and instrument is based on the endoscopic image reference frame.

The endoscopic image reference frame is also used if the control interfaces 222 are switched to a camera 46 control mode, in some cases, if the camera 46 control mode is selected, the surgeon may move the distal end of Visualization Device (VD) 58 (212) by moving one or both of the control interfaces 222 together. The surgeon may then intuitively move (e.g., pan, tilt, zoom) the displayed stereoscopic image by moving the control interfaces 222 as if holding the image in his or her hands.

In one embodiment, illustrated in FIG. 18, a headrest 230 is positioned above stereo image viewer system 226. As the surgeon is looking through stereo image viewer system 226, the surgeon's forehead is positioned against headrest 230. In some embodiments of the present disclosure, manipulation of Visualization Device (VD) 58 (212) or other surgical instruments can be achieved through manipulation of head-rest 230 instead of utilization of the control interfaces 222.

FIG. 19 is a front view of a vision cart component 240 of a surgical system. For example, in one embodiment, the vision cart component 240 is part of robotic surgical system 10 shown in FIG. 16. The vision cart 240 can house robotic surgical system's 10 central electronic data processing unit 242 (e.g., all or portions of control system 22 shown in FIG. 16 and vision equipment 244 (e.g., portions of the image capture system 152 shown in FIG. 16. The central electronic data processing unit 242 includes much of the data processing used to operate the robotic surgical system 10. In various implementations, however, the electronic data processing may be distributed in the surgeon console 12 and teleoperational assembly 200. The vision equipment 244 may include camera 46 control units for the left and right image capture functions of Visualization Device (VD) 58 (212). The vision equipment 244 may also include illumination equipment (e.g., a Xenon lamp) that provides illumination for imaging the surgical site. As shown in FIG. 19, vision cart 240 includes an optional touchscreen monitor 246 (for example a 24-inch monitor), which may be mounted elsewhere, such as on the assembly 200 or on a patient side cart. The vision cart 240 further includes space 248 for optional auxiliary surgical equipment, such as electrosurgical units, insufflators, suction irrigation instruments, or third-party cautery equipment. The teleoperational assembly 200 and the surgeon's console 120 are coupled, for example, via optical fiber communications links to the vision cart 240 so that the three components together act as a single teleoperated minimally invasive robotic surgical system 10 that provides an intuitive telepresence for the surgeon.

The touchscreen monitors 246 can form a user interface that provides status and prompts during the guided setup process described herein. While a touchscreen monitor is shown, it is worth noting that other types of user interfaces may be used, including those, described above with reference to the touchpad 254. It is worth noting that some guided setup processes receive no user inputs at the user interface because the robotic surgical system is arranged to sense or otherwise recognize when a setup step is complete. Accordingly, in some embodiments the user interface is merely a display 24 that does not receive user inputs.

As non-limiting examples, some or all of the assembly 200 can be implemented in a virtual (simulated) environment, wherein some or all of the images seen by the surgeon at the surgeon's console 220 can be synthetic images of instruments and/or anatomy, in sonic embodiments, such synthetic imagery can be provided by the vision cart component 240 and/or directly generated at the surgeon's console 220 (e.g., via a simulation module).

In one embodiment, servo control is provided for transferring mechanical motion of masters to manipulator assemblies 220 to 223. As a non-limiting example, servo control provides force feedback and, in some respects, torque feedback from surgical instruments to the hand-operated masters. Servo control can include safety monitoring controller (not shown) to safely halt robotic surgical system operation, or at least inhibit all surgical robot 20 motion, in response to recognized undesirable conditions, e.g., exertion of excessive force on the patient, mismatched encoder readings, and the like.

A variety of different surgical instruments 18 can be used with robotic surgical system 10. These include but are not limited to: graspers, dissection instruments, scissors, coagulators, clip applicators, needle holders, electric scalpels, suction/irrigation instruments 18, laparoscopic tools, articulated instruments, instruments with actuating rods, and the like.

In certain embodiments, robotic surgical systems 10 can include the measuring of various parameters associated with an end effector 48 before, during, and/or after a surgical action or procedure. The monitored parameters can include rpms, angle, direction, sound, or the like. The monitored parameters can be combined with location data, tissue type data, and/or metadata to train an AI system 42 for guiding surgical instrument 18 to automatically perform a surgical action, procedure, or an entire surgery.

Figure 21A:
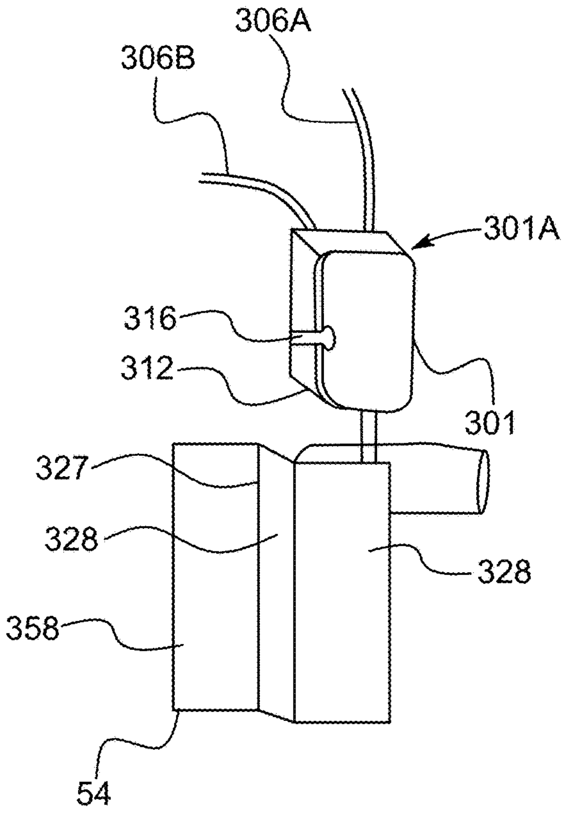
FIG. 21A illustrates one embodiment of mounting of a surgical tool to an adapter of a robotic surgical arm of the present invention.
Figure 21B:
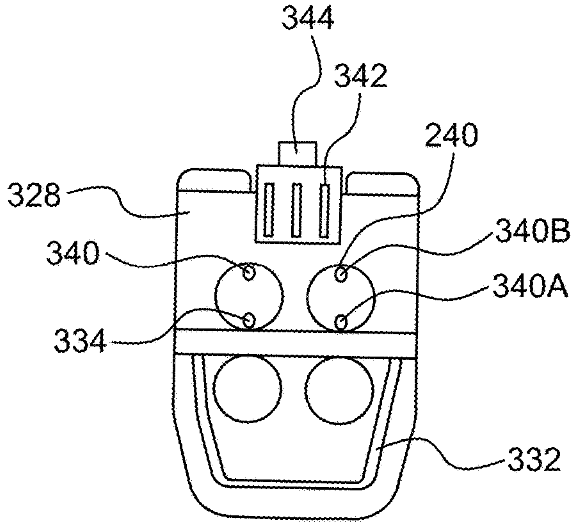
FIG. 21B illustrates one embodiment of an adapter of a robotic surgical arm for mounting a surgical instrument of the present invention.
Figure 21C:
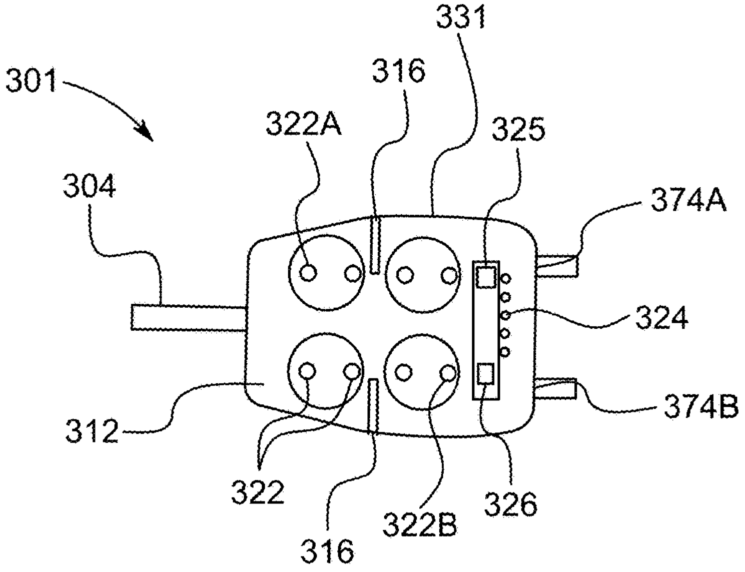
FIG. 21C illustrates one embodiment of a surgical instrument that interfaces to a robotic surgical arm of the present invention.

Referring to FIGS. 21A-21C each robotic arm 54 can include a linkage that constrains the movement of the surgical instrument 18. In one embodiment, linkage includes rigid links coupled together by rotational joints in a parallelogram arrangement so that the robotic surgical instruments rotate around a point in space. At the point in space, robotic arm 54 can pivot the surgical instrument 18 about a pitch axis and a yaw axis. The pitch and yaw axes intersect at the point, which is aligned along a shaft of a robotic surgical instrument 18. The shaft is a rotatable hollow tube that may have a number of cables of a cable drive system to control the movement of the end effectors 48 (312).

In one embodiment, robotic arm 54 provides further degrees of freedom of movement to the robotic surgical instrument 18. Along an insertion axis, parallel to the central axis of the shaft of the surgical instrument, the robotic surgical instrument 18 can be configured to slide into and out from a surgical site. Surgical instrument 18 can also rotate about the insertion axis. As surgical instrument 18 slides along or rotates about the insertion axis, the center point is relatively fixed with respect to the patient console 16. That is, the entire robotic arm is generally moved in order to maintain or re-position back to the center point.

In one embodiment, linkage of the robotic arm 54 is driven by a series of motors therein in response to commands from one or more processors 62 or computer 151. The motors in the robotic arm 54 are also used to rotate and/or pivot surgical instrument 18 at the center point around the axes. If a surgical instrument 18 further has end effectors 48 to be articulated or actuated, still other motors in the robotic arm 54 may be used to control the end effectors 48. Additionally, the motion provided by the motors may be mechanically transferred to a different location such as by using pulleys, cables, gears, links, cams, cam followers, and the like or other known means of transfer, such as pneumatics, hydraulics, or electronics.

In one embodiment, surgical arm 54 can include an adapter 328 or other surgical instruments 18 may be mounted. The front side of adaptor 328 is generally referred to as an instrument side 330 and the opposite side is generally referred to as a holder side (not shown).

As illustrated in FIGS. 21(*a*) and (*b*) surgical instrument 18 includes a mountable housing 301 including an interface base 312 that can be coupled to adapter 328 to mount surgical instrument 400. The interface base 312 and the adapter 328 may be electrically and mechanically coupled together to actuate the surgical instrument 18. Rotatably coupled to the interface base 312 are one or more rotatable receiving members 318, also referred to as input disks. Each of the one or more rotatable receiving members 318 includes a pair of pins 322*a* and 322*b* generally referred to as pins 322. Pin 322(*a*) is located closer to the center of each rotatable receive member 318 than pin 322(*b*). The one or more rotatable receiving members 318 can mechanically couple respectively to one or more rotatable drivers 334 of the adapter 328. The surgical instrument 18 may further include release levers 316 to release it from the adapter 328 and the robotic arm.

In one embodiment, interface base 312 can have one or more electrical contacts or pins 324 to electrically couple to terminals of an electrical connector 342 of the adapter 328. The interface base 312 can have a printed circuit board 325 and one or more integrated circuits 326 coupled thereto and to the one or more pins 324. The one or more integrated circuits 326 store surgical instrument information that may be used to identify the type of surgical instrument 18 coupled to the robotic arm, so that it may be properly controlled by the surgeon control console 12.

Referring to FIGS. 21A-21C, interface or surgical instrument base 312 of the surgical instrument 400 can couple to an adapter 328 so that it is removably connectable to the robotic surgical system 10. Other surgical instruments 18 with the same type of surgical instrument base may also couple to the adapter and then the robotic arm. During surgery, the adapter 328 is coupled to the moveable carriage 337. A surgical instrument 12 can translate with the carriage 337 along an insertion axis of the robotic surgical arm 353.

In one embodiment, surgical instrument base 312 includes receiving elements or input disks 318 that releasably couple through an adapter to a rotatable driving element 334 that is mounted on the carriage 337 of robotic arm assembly 54. The rotatable driving elements 334 of the carriage 337 are generally coupled to actuators (not shown), such as electric motors or the like, to cause selective angular displacement of each in the carriage 337.

In one embodiment, when mounted to a surgical arm 54, end effectors 48 may have a plurality of degrees of freedom of movement relative to arm 54, in addition to actuation movement of the end effectors 48. The end effectors 48 of the surgical instruments 18 are used in performing a surgical operation such as cutting, shearing, grasping, gripping 66 (550), clamping, engaging, or contacting tissue adjacent a surgical site.

As illustrated in FIG. 21C, surgical instrument base 312 may be enclosed by a cover 372 to which one or more electrical connectors 374(*a*)-374(*b*) may be mounted. In one embodiment, adapter 328 includes one or more rotatable drivers 334 rotatably coupled to a floating plate 336. The rotatable drivers 334 are resiliently mounted to the floating plate 336 by resilient radial members which extend into a circumferential indentation about the rotatable drivers. The rotatable drivers 334 can move axially relative to floating plate 336 by deflection of these resilient structures.

In one embodiment, floating plate 336 has a limited range of movement relative to the surrounding adaptor structure normal to the major surfaces of the adaptor. Axial movement of the floating plate helps decouple the rotatable drivers 334 from a surgical instrument 18 when its release levers 316 are actuated.

In one embodiment, one or more rotatable drivers 334 of the adapter 328 may mechanically couple to a part of the surgical instruments 18. Each of the rotatable drivers 34 may include one or more openings 340 to receive protrusions or pins 322 of rotatable receiving members 318 of the surgical instruments 18. The openings 340 in the rotatable drivers 334 are configured to accurately align with the rotatable receiving elements 318 of surgical instruments 18.

In one embodiment, inner pins 322(*a*) and the outer pins 322(*b*) of the rotatable receiving elements 318 respectively align with the opening 340(*a*) and the opening 340(*b*) in each rotatable driver. Pins 322(*a*) and openings 340(*a*) are at differing distances from the axis of rotation than the pins 322(*b*) and openings 340(*b*) so as to ensure that rotatable drivers 334 and the rotatable receiving elements 318 are not aligned 180 degrees out of phase from their intended position. Additionally, each of the openings 340 in the rotatable drivers may be slightly radially elongated so as to fittingly receive the pins in the circumferential orientation. This allows the pins 322 to slide radially within the openings 340 and accommodate some axial misalignment between the surgical instrument and the adapter 328, while minimizing any angular misalignment and backlash between the rotatable drivers 334 and the rotatable receiving elements 318. Additionally, the interaction between pins 322 and openings 340 helps restrain the surgical instrument 18 in the engaged position with the adapter 328 until the release levers 316 along the sides of the housing 301 push on the floating plate 236 axially from the interface so as to release the surgical instrument 18.

When disposed in a first axial position (away from the surgical instrument side 330) the rotatable drivers are free to rotate without angular limitation. The one or more rotatable drivers 334 may rotate clockwise or counterclockwise to further actuate the systems and instruments of the robotic surgical system 10. However, as the rotatable drivers move axially toward the surgical instrument side 330, tabs (extending radially from the rotatable drivers) may laterally engage detents on the floating plates so as to limit the angular rotation of the rotatable drivers about their axes. This limited rotation can be used to help engage the rotatable drivers the rotating members of the surgical instrument as the pins 322 may push the rotatable bodies into the limited rotation position until the pins are aligned with (and slide into) the openings 340 in the rotatable drivers.

In one embodiment, mounting of surgical instrument 18 to the adapter 328 can utilize an insertion of tip or distal end of the shaft or hollow tube of the surgical instrument 18 through a cannula (not shown) and sliding the interface base 312 into engagement with the adapter 328. A lip 332 on the surgical instrument side 330 of the adaptor 328 slidably receives the laterally extending portions of the interface base 312 of the robotic surgical instrument 18. A catch 344 of adapter 328 may latch onto the back end of the interface base 312 to hold the surgical instrument 18 in position. The protrusions or pins 322 extending from the one or more rotatable members 318 of the surgical instrument 18 couple into the holes 340*a*-340*b* (generally referred to as holes or openings 340) in the rotatable drivers 334 of the adapter 328.

In one embodiment, arrange of motion of the rotatable receiving elements 318 in the surgical instrument 18 may be limited. To complete the mechanical coupling between the rotatable drivers of the adapter and the rotatable receiving elements 318, the operator O at the surgeon console 12 may turn the rotatable drivers in one direction from center, turn the rotatable drivers in a second direction opposite the first, and then return the rotatable drivers to center. Further, to ensure that the pins 322 enter openings 340 of rotatable driver adapter 328, the adapter 328 and surgical instrument 18 mounted thereto may be moved together.

As discussed above, surgical instrument 18 can include one or more integrated circuits 326 to identify the type of surgical instrument 18 coupled to the robotic arm, in order to properly controlled by surgeon console 12. Robotic surgical system 10 can determine whether or not the surgical instrument 18 is compatible or not, prior to its use.

As a non-limiting example, robotic surgical system 10 verifies that the surgical instrument 18 is of the type which may be used with the robotic surgical system 10. The one or more integrated circuits 326 may signal to the computer 151 in the surgeon console 12 data regarding compatibility and instrument-type to determine compatibility as well as control information. One of the integrated circuits 326 may include a non-volatile memory to store and read out data regarding robotic surgical system compatibility, the instrument-type and the control information. In an exemplary embodiment, the data read from the memory includes a character string indicating surgical instrument compatibility with the robotic surgical system 10. Additionally, the data from the surgical instrument memory will often include an instrument-type to signal to the surgeon control console how it is to be controlled. In some cases, the data will also include surgical instrument calibration information. The data may be provided in response to a request signal from the computer 151.

In one embodiment, instrument-type data indicates the kind of surgical instrument 18 has been attached in a surgical instrument change operation. As a non-limiting example, instrument-type data can include information on wrist axis geometries, surgical instrument strengths, gripper 550 force, the range of motion of each joint, singularities in the joint motion space, the maximum force to be applied via the rotatable receiving elements, the surgical instrument transmission system characteristics including information regarding the coupling of rotatable receiving elements to actuation or articulation of a system within the robotic surgical instrument, and the like.

In one embodiment, instrument-type data is not stored in integrated circuits 326 but is stored in memory or a hard drive of the computer 151. In one embodiment, an identifier is stored in integrated circuits 326 to signal the computer 151 to read the relevant portions of data in a look up table store in the memory or the hard drive of computer 151. The instrument-type data in the look-up table may be loaded into a memory of computer 151 by the manufacturer of the robotic surgical system 10. As a non-limiting example, look-up table can be stored in a flash memory, EEPROM, or other type of non-volatile memory. As a new instrument-type is provided, the manufacturer can revise the look-up table to accommodate the new instrument-specific information. It should be recognized that the use of surgical instruments 18, which are not compatible with the robotic surgery system 10, for example, which do not have the appropriate instrument-type data in an information table, could result in inadequate robotic control over the surgical instrument 18 by the computer 151 and the operator O.

In one embodiment, surgical instrument specific information is stored in integrated circuits 326, such as for reconfiguring the programming of computer 151 to control surgical instrument 18. In one embodiment, this includes calibration information, such an offset, to correct a misalignment in the surgical instrument 18. The calibration information can be factored into the overall control of the surgical instrument 18. The storing of such calibration information can be used to overcome minor mechanical inconsistencies between surgical instruments 18 of a single type.

As a non-limiting example, information about a surgical instrument 18 life span, surgical instrument life, and cumulative surgical instrument 18 use can be stored on the surgical instrument memory and used by computer 151 to determine if the surgical instrument is still safe for use.

In one embodiment, surgeon console 12 generates the control signals to control surgical instruments 18 in a surgical site and medical equipment that supports surgical instruments 18. As a non-limiting example, surgeon console 12 can include a binocular or stereo viewer, an armrest, a microphone, a pair of master controllers for end effector 48 input control, wrist input control, and arm input control within a workspace, one or more speakers, foot pedals 68, viewing sensor, and the like.

Figure 22:
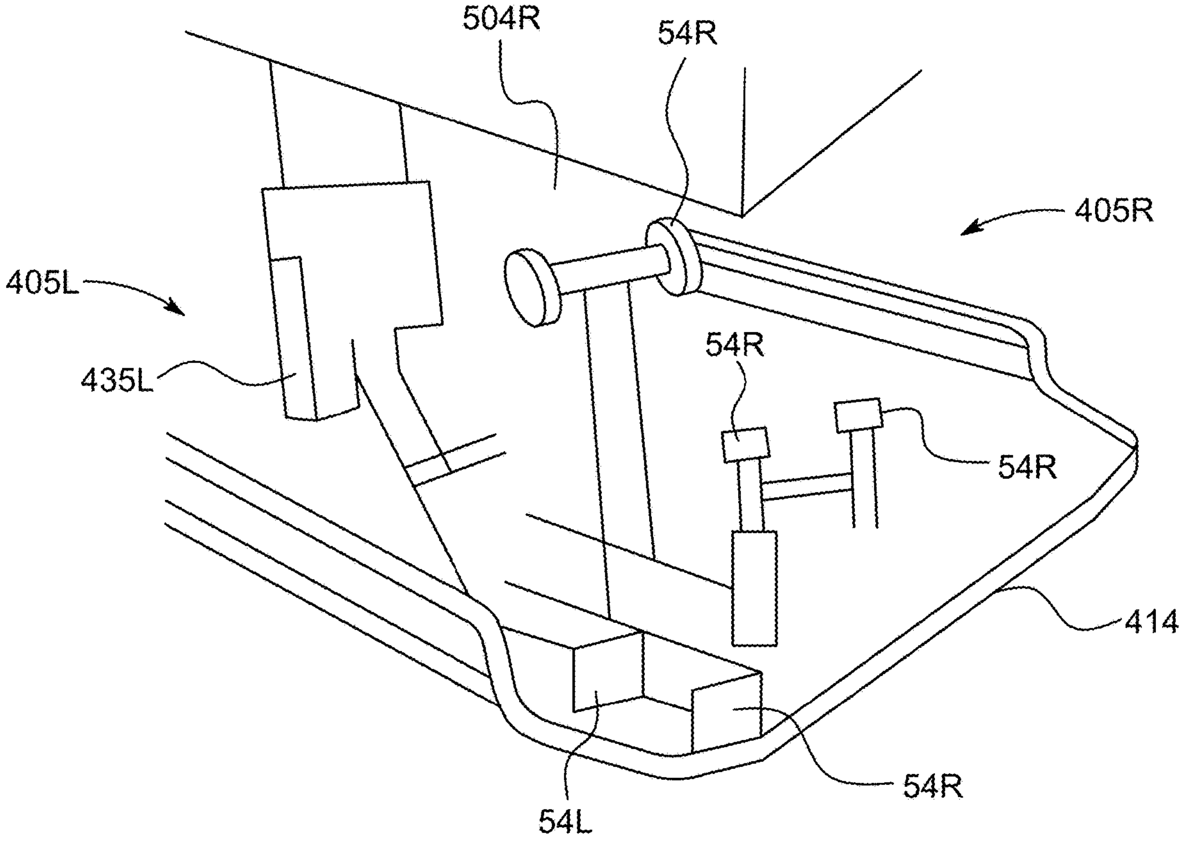
FIG. 22 illustrates one embodiment of a workspace in a surgeon's console showing a left master controller and a right master controller of the present invention.

As a non-limiting example, illustrated in FIG. 22, master controllers 405(L), and 405(R), at surgeon console 12 include a control input grip or master gripper 525 and a control input wrist 414 coupled together to control input arms 54(L), and 54(R). In one embodiment, control input wrist 414 is a gimbaled device that pivotally supports a master gripper 525 of surgeon console 12 to generate control signals that are used to control patient console 16 and surgical instruments 18. In one embodiment, control input wrists 414 for the left and right master controllers are supported by a pair of control input arms 54. Control input wrist 414 includes first, second, and third gimbal members. The surgeon console 12 has a left master controller 405(L) and a right master controller 405(R). The left master controller 405(L) includes a left control input arm 54(L), a left control input wrist 54(L) and a left control input grip 54(L). The right master controller 405R includes a right control input arm 54(R), a right control input wrist 54(R) and a right control input grip.

Figure 23:
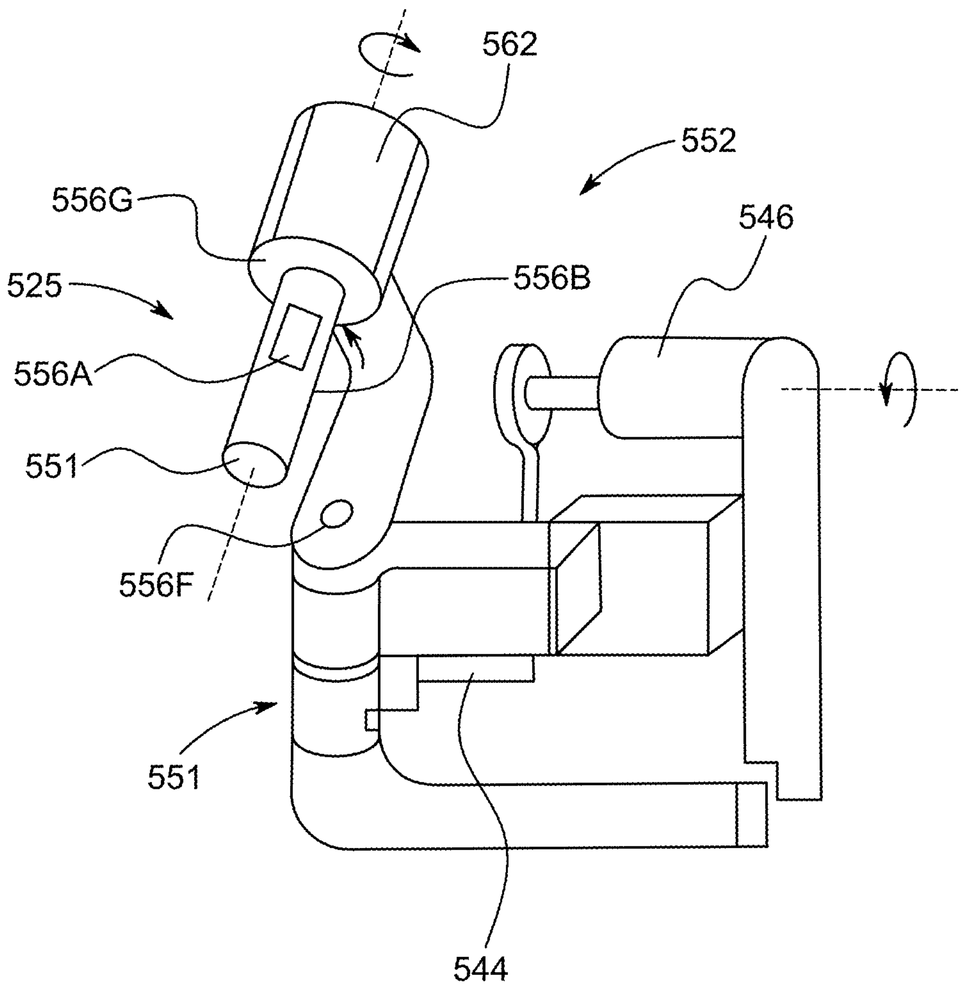
FIG. 23 illustrates one embodiment of a gimbaled control input wrist pivotally supporting a master grip control handle for a robotic surgical master control console of the present invention.
Figure 24:
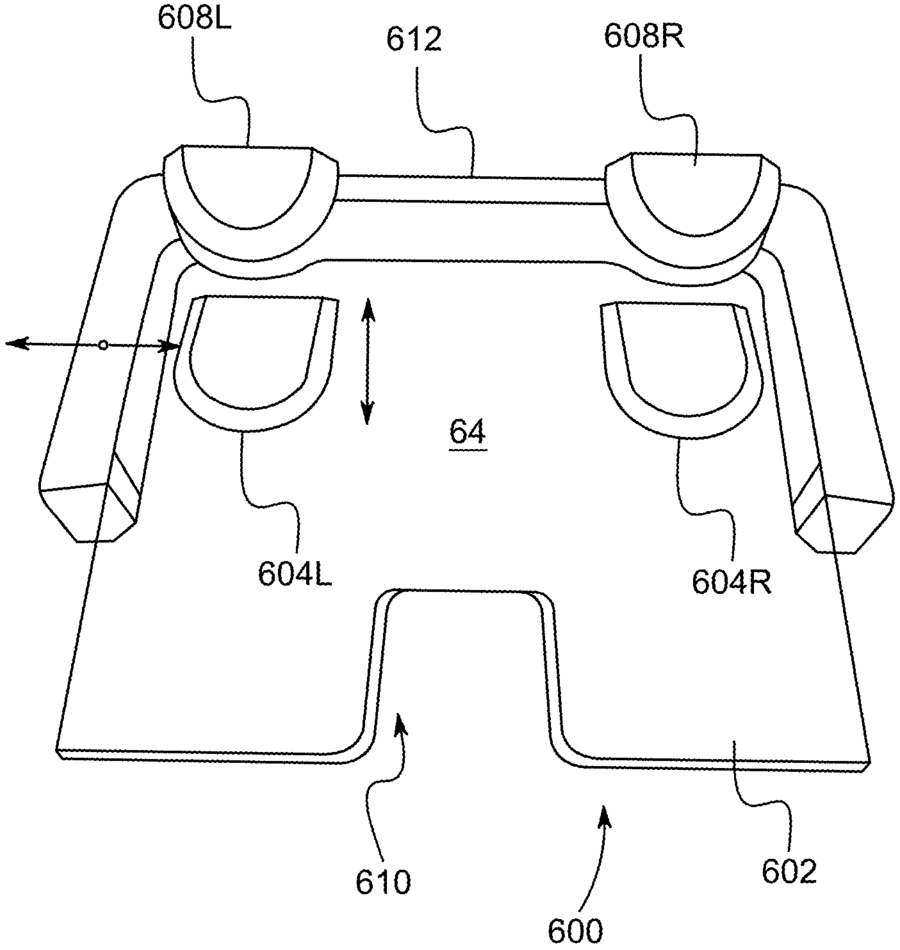
FIG. 24 illustrates one embodiment of an integrated pedal system of the surgeon's control console of the present invention.

FIG. 23 is a perspective view of a control input wrist 552 representative of the left control input wrist, and the right control input wrist is illustrated. The master controllers at the surgeon's console include a control input grip or master gripper 525 and a control input wrist 552 coupled together to a control arm (see control input arms 935(L), in FIG. 22). The control input wrist 552 is a gimbaled device that pivotally supports the master gripper 525 of the master control console 150 to generate control signals that are used to control patient console 16 surgical instruments 18, including electrosurgical robotic instruments 18(*a*) and 18(*b*). A pair of control input wrists 552 for the left and right master controllers are supported by a pair of control input arms in the work site 516 of the master control console, The control input wrist 552 includes first, second, and third gimbal members 562, 564, and 566. The third gimbal member 566 is rotationally coupled to a control input arm (not shown) of the master control console 150, 150(*a*).

Master gripper 525 includes a tubular support structure 551, a first gripper 550(*a*), and a second gripper 550(*b*). The first and second grippers 550(*a*) and 550(*b*) are supported at one end by the structure 551. The master gripper 525 can be rotated. Grippers 550(*a*), 550(*b*) can be squeezed or pinched together about the tubular structure 551.

Master gripper 525 is rotatably supported by the first gimbal member 562 by means of a rotational joint 556(*g*). The first gimbal member 562 is in turn, rotatably supported by the second gimbal member 564 by means of the rotational joint 556(*f*). Similarly, the second gimbal member 564 is rotatably supported by the third gimbal member 566 using a rotational joint 556 *d*. In this manner, the control wrist allows the master gripper 525 to be moved and oriented in the workspace 516 using three degrees of freedom. The movements in the gimbals of the control wrist 552 to reorient the master gripper 525 in space can be translated into control signals to control patient console 16 and surgical instruments 18.

Movements in grippers 550(*a*), and 550(*b*) of master gripper 525 can also be translated into control signals to control patient console 16 and surgical instruments 18. In particular, the squeezing motion of grippers 550(*a*), and 550(*b*) over their freedom of movement, and be used to control the end effectors 48 of the robotic surgical instruments 18.

To sense the movements in master gripper 525 and generate controls signals, sensors can be mounted in the handle of master gripper 525 as well as the gimbal member 562 of the control input wrist 552. Exemplary sensors may be a Hall effect transducer, a potentiometer, an encoder, or the like.

As a non-limiting example, the robotic surgical system 10 includes one or more of: one or more cameras 46 and multiple end effectors 48. surgical control software 38; surgeon controls; image recognition database 34; procedure database 36; a medical image database; and the like. As a non-limiting example, procedure database 36 can include medical records data, images (e.g., pre- and post-surgical images), physician input, sensor data, and the like. In one embodiment, image recognition database 34 is populated by images taken by the cameras 46 that defined by surgeons and can be updated with each use of robotic surgical system 10 for greater accuracy. In one embodiment, surgeon controls are used for manual manipulation of the surgical robot. Surgical control software 38 may include an incision marking module, and AI system 42 include a progression module. In one embodiment, the surgical control software 38 begins when initiated by the surgeon.

In one embodiment, robotic surgical system 10 initiates an incision marking module which ensure the patient is properly positioned and the incision site is marked. When the incision marking module is complete. AI system 42 may be initiated. In one embodiment, the incision marking module may be designed to cover the steps in the spinal surgery between when the patient is placed on the table and when AI system 42 system makes the first incision. In one embodiment, the module begins when it receives a prompt from the surgical control software 38. In one embodiment, the incision location, in this example just above the L4 vertebrae, is identified from the pre-operative plan. In one embodiment, the robotic surgical system 10 captures an image of the patient to determine if they are properly positioned on the operating table. If they are not, the surgeon or assistant are prompted for the necessary adjustment and a new image may be captured. This loop continues until robotic surgical system 10 is satisfied that the patient is properly positioned.

In one embodiment, AI system 42 system uses the camera 46 to take an image of the point of interest and the progression module may compare that image to the image recognition database 34 to determine if the tissue present is the desired tissue type that will allow the surgical robot 20 to proceed. In one embodiment, the progress through the tissue type is displayed based on the number of layers of the current tissue removed as compared to the average number of layers removed in other patients who had the same procedure and had a similar anatomical volume of their surgical point of interest.

As a non-limiting example, imaging system coupled to the image software 38 is in the same location. It can be co-located on the same robot arm as the bone removal end effector 48 or on another mount that allows it a view of the point of interest. In one embodiment, the imaging system may take an image of the point of interest, and the progression module will run. When the tissue type is confirmed, the bone removal end effector 48 removes a small layer of tissue. In one embodiment, the imaging system repeats the process of tissue type confirmation, followed by the end effector 48 removing another layer of tissue. This loop continues until the imaging system identifies a different tissue type.

In one embodiment, the imaging system and progression module are initially trained using a neural network/machine learning. Using machine learning systems which construct algorithms that can learn from and then make predictions on the image data, which is a common task in machine learning. Such algorithms work by making image data-driven predictions through building a mathematical model from image input data. In one embodiment, the image data is used to build the final model which usually comes from multiple datasets (in this case, dataset of previous operations visual data with metadata associated with the images from doctor articulated tissue types). In particular, three data sets (images, metadata of tissue type and metadata of bone portions unfolding in the images over time) may be used in different stages of the creation of the model. A third party, associate or surgeon can input or change metadata. For example, the metadata can include surgeon defined metadata. In some embodiments, the metadata can be defined by AI system 42. In some embodiments, the metadata can include both surgeon and assistants, prior surgeons and assistants, third parties, and AI defined data.

In one embodiment, the model is initially fit on a training dataset, which is a set of examples used to fit the parameters (e.g., weights of connections between "neurons" in artificial neural networks) of the model. In one embodiment, the model (e.g., a neural net or a naive Bayes classifier) may be trained on the training dataset using a supervised learning method (e.g., gradient descent or stochastic gradient descent). In practice, the training dataset often includes pairs of generated "input vectors" with the associated corresponding "answer vector" (commonly denoted as the target). In one embodiment, the current model is run with the training dataset and produces a result, which is then compared with the target, for each input vector in the training dataset. Based on the result of the comparison and the specific learning algorithm being used, the parameters of the model are adjusted. In one embodiment, the model fitting can include both variable selection and parameter estimation. One or more models predict the responses for the observations in a second dataset called the validation dataset. In one embodiment, the validation dataset provides an unbiased evaluation of a model fit on the training dataset while tuning the model's parameters. Validation datasets can be used for regularization by early stopping stop training when the error on the validation dataset increases, as this may be a sign of overfitting to the training dataset. This simple procedure is complicated in practice by the fact that the validation dataset's error may fluctuate during training, which would require added ad-hoc rules for deciding when overfitting has truly begun. Finally, the test dataset is a dataset used to provide an unbiased evaluation of a final model fit on the training data.

Once this trained dataset is built, the trained model may be fed into robotic surgical system 10 and as tissues are identified, the tissue types are annotated virtually over the real-time images, with a percent probability of identification. This allows the surgeon to have an AI image recognition assistant.

In one embodiment, robotic surgical system 10 includes a failsafe that allows the surgeon on hand to stop the process. Stopping the process may include a teaching step in which the surgeon defines the tissue type visible, to improve the functionality of the image recognition software of image recognition database 34.

In one embodiment, the failsafe robotic surgical system 10 provides historical data of many operations that stores the amount of time (video) and the virtual identified images on the tissue. In one embodiment, the tissues identified may be in a time sequence as the operation proceeds. In a real-time operation, the sequence of image-recognized tissue (and the timing of getting to and through these recognized tissues) is compared to the historical database. If the real-time recognized tissues are correlated with the same sequence of tissues in the historical database, robotic surgical system 10 proceeds. However, if a recognized tissue does not appear in the sequence history, or if the recognized tissue appears earlier than expected, robotic surgical system 10 is alerted, which causes an alarm, with a virtual message over the non-normal images.

In one embodiment, there could be other fail-safe triggers including but not limited to: the length of time between recognized tissues that are normal; the probability of the recognition trending down; and the image quality starting to degrade, etc. In this way the failsafe system could have multiple processes running simultaneously.

When AI system 42 system completes a step in its entirety, it may return to the surgical control software 38, which determines based on the pre-operative plan, if the procedure is complete. If the procedure is complete, the program ends.

If the program is not complete, the pre-operative plan is consulted to determine if the next surgical step requires a different end effector 48. End effectors 48 can include surgical instruments 18 such as retractor tubes and surgical hardware, in addition to the incision markers, bone removal tools, skin/muscle fascia incision tools, etc. If a new end effector 48 is needed, the surgeon or support staff makes the hardware adjustment before robotic surgical system 10 proceeds to the next step in the pre-operative plan. After the needed end effector 48/tool is put into place, or if the same end effector 48/tool from the previous step is appropriate, robotic surgical system 10 may go back to AI system 42 system until the next surgical step is completed. This process continues to loop until the procedure is complete. To perform multiple procedures on a patient, the end effector 48 can be replaced to begin another procedure.

In one embodiment, robotic surgical system 10 may then initiate the incision marking module which will ensure the patient is properly positioned and the incision site is marked. When the incision marking module is complete, AI system 42 system is initiated.

In one embodiment, AI system 42 system works through each step in the surgical process. When AI system 42 system completes a step in its entirety, it returns to the surgical control software 38, which determines based on the pre-operative plan, if the procedure is complete.

If the procedure is complete, the program ends, and the pre-operative plan is consulted to determine if the next surgical step requires a different end effector 48. End effectors 48 in this scenario also include surgical instruments 10 such as retractors and surgical hardware, in addition to the incision markers, bone removal tools, incision tools (e.g., skin/muscle fascia incision tools), etc. If a new end effector 48 is needed, the surgeon or support staff can make the hardware adjustment before robotic surgical system 10 proceeds to the next step in the pre-operative plan. After the needed end effector 48/tool is put into place, or if the same end effector 48/tool from the previous step is appropriate, robotic surgical system 10 may go back to the AI system 42 system until the next surgical step is completed. This process continues to loop until the procedure is complete.

In one embodiment, an incision marking module is provided that is part of the surgical control software 51, according to an embodiment. In one embodiment, the incision marking module is designed to cover the steps in the surgery between when the patient is placed on the table and when AI system 42 system suggests or implements the first incision.

In one embodiment, the module begins when it receives a prompt from the surgical control software. In one embodiment, the incision location, in this example just above the L4 vertebrae, is identified from the pre-operative plan.

In one embodiment, the module may then capture an image of the patient to determine if they are properly positioned on the operating table. If they are not, the surgeon or support staff are prompted for the necessary adjustment and a new image is captured. This loop continues until robotic surgical system 10 is satisfied that the patient is properly positioned.

In one embodiment, the end effector 48 is navigated to the point of interest.

In one embodiment, then the progression module is run, which may update the progress on the robotic surgery system 10 display 24 and return if the tissue at the point of interest is the desired tissue type. So, if the tissue type identified is not bone, robotic surgical system 10 stops, alerts the surgeon and polls for their input.

In one embodiment, the surgeon will need to define the tissue type currently at the point of interest. If the surgeon defines the current tissue type as the desired tissue type, this updates the image recognition database 34 and robotic surgical system 10 returns to the progression module with the updated image recognition definitions. If the surgeon defines the tissue as any other type of tissue than the desired tissue type, the image definition is added to the database 34 and the number of layers removed of the desired tissue type for the current patient is recorded in the 36.

Figure 5:
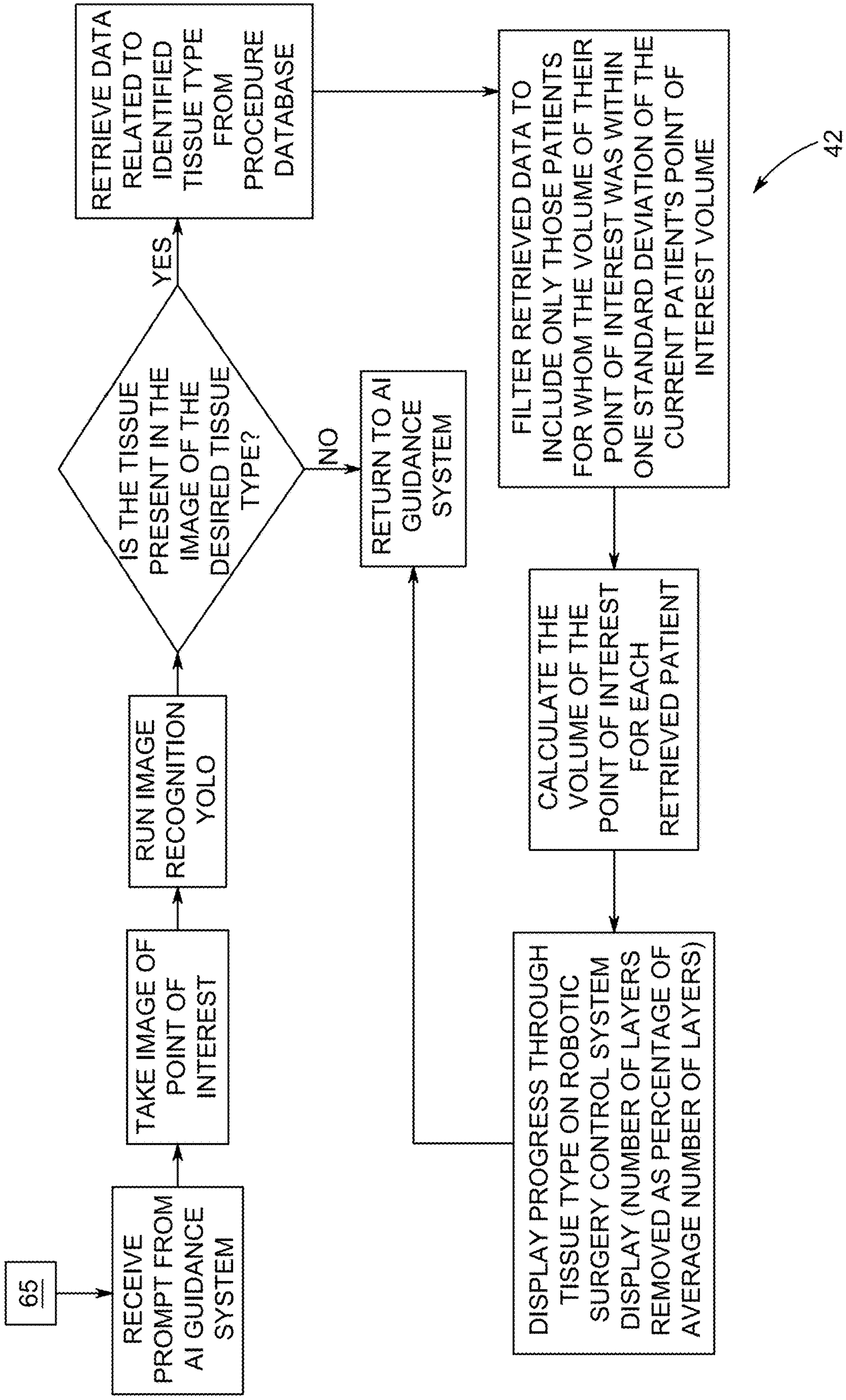
FIG. 5 illustrates one embodiment of a progression module of the present invention.

FIG. 5 represents the progression module, according to an embodiment. In one embodiment, the progression module is triggered by AI system 42 system when the imaging system and the end effector 48 are at the point of interest on the current patient.

An image of the point of interest is taken and an image recognition system associated with image recognition 34 is used to identify the tissue type present in the image taken of the point of interest on the current patient. In one embodiment, the image recognition system utilizes the database 34 to identify the tissue type and to store the definitions of tissue types found in images as they are defined by surgeons using the robotic surgical system 10.

In one embodiment, the real-time images may be fed into a "trained neutral network image system" as described above, which uses this historical data to inform a YOLO ("you only look once") system. In one embodiment, the real-time images may be used to identify the tissue type present in the image taken of the point of interest on the current patient. Unlike simply identifying the tissue types, which we have discussed above by adding a virtual tissue tag on the images, this YOLO system goes further, in that it can detect distances and positions between the boundary boxes. In this way, tissue type will not only be defined virtually over the real-time images, but virtual distances are overlaid and can be highlighted when they are outside norms (again these distances of boundary boxes are pre-trained). In one embodiment, the image recognition system utilizes the historical image database and YOLO to identify the tissue type and their positions to provide real-time augmentation data to the surgeons using the robotic surgical system.

If the tissue type identified is not the desired tissue type for the surgical robot 20 to proceed with tissue removal, the module ends and returns to AI system 42 system. If the tissue type identified is the desired tissue type to proceed with tissue removal, data related to the identified tissue type is retrieved from the 36

In one embodiment, pre-operative images are used. A surgeon, assistant or third party can input information for performing procedures. In one embodiment, the information can include, without limitation, targeted tissue, non-targeted tissue, critical tissue (e.g., tissue to be protected or avoided), access paths, cutting/drilling paths, instrument orientations (e.g., delivery instruments, surgical instruments 18, and the like), working spaces, safety barriers, hold spots, or the like. In one embodiment, the information can be used to determine or modify a surgical plan and can be inputted via a touch screen, keyboard, or the like. A method of using an image in which a sketch on the image indicates parts of the anatomical structure to be removed. This is a freehand adjustment by the surgeon to the preoperative plan, layered on top of medical imaging (MRI, CT, etc.). This adjustment to the surgical plan is transmitted to surgical robot 20 and it only removes the desired area; the surgeon supervises the surgical robot 20 during the procedure to take over/resume the operation if necessary.

In one embodiment, pre-operative image uses an interactive user interface. In one embodiment, the image received from the surgical robot 20 is displayed on a touch screen/user interface inside the operating room and the surgeon sketches on the image which of the corresponding area of tissue is supposed to be removed. Other important areas can be identified (such as nerves) to warn the surgical robot 20 to stay away from sensitive areas. This is applicable to all steps past this one in this process but is documented here as this is the first step in which the surgeon would mark out areas during the procedure as opposed to during pre-operative planning.

In one embodiment, incision localization/markings are made as pre-operative images on an actual image using interactive user interface. robotic surgical system 10 can deploy graphical surgical instruments 18, that allows the surgeon to draw shapes of different colors over the image. The shapes can be auto filled with the suggested colors and meta-tags (e.g., distance depth, speed of drill, amount of dither, etc.). For instance, robotic surgical system 10 could allow the surgeon in drawing mode to define the draw pen or mouse to be defined as "red, 1 mm deep, 100 rpm, +/−5 rpm", where red would correspond to drill, 1 mm deep at 100+/−5 rpm. In another area for instance, the surgeon could have defined a yellow +0.5 mm which is a region that the surgical robot 20 is barred from running. One could image many other user interface controls, such as (1) cutting or drilling paths, (2) degrees of safety barriers along the cutting, (3) hold spots, (4) jump to another spots, etc. The surgeon would stand by during the procedure and can turn off the machine at any time. The drill also has built-in safeguards. For example, it can detect if it is too close to a nerve, the instrument will automatically shut off.

As a non-limiting example, incision localization and markings are made using interactive user interface to resolve latency issues.

As a non-limiting example, incision localization and markings are made such as multiple imaging systems for problem space identification in spinal surgery. A method that combines multiple imaging systems to identify a problem space in a patient's spine. An algorithm is applied to the images to calculate the best incision location based on where the problem space is located. This algorithm accounts for the surgical procedure being used when identifying the incision site.

As a non-limiting example, methods are provided that allows surgeons to annotate where a surgical robot 20 should move or adjust to in order to place the guidewire while locating an incision site. The surgical robot 20 can learn where it is commanded to move and store the information in a database. The surgical robot 20 can access this database to use for references during future procedures. This increases efficiency, accuracy, and repeatability for locating incision sites.

As a nonlimiting example, robotic surgical system 10 allow the surgeon to pick the most applicable shape to use for different procedures or at a specific point in a procedure. The shapes can also be produced through the combining of different guide wires. Guidewire shape would be determined by AI using correlations between patient attributes, procedure type, wire shape, and postoperative outcomes.

As a non-limiting example, robotic surgical system 10 projects an imaging system output onto the patient to show where different tissue types are located underneath the skin. The projection would also include a projection of the guide wire to help the surgeon visualize the best point of incision. This increases the accuracy of the incision point. This can be done with high-speed projectors, or with an augmented reality 20 for the surgeon. Alternate embodiments can include virtual reality headsets for incision placement.

In one embodiment, robotic surgical system 10 uses surgical control software 38 that utilizes AI to determine the optimal trajectory and incision placement for any type of spinal surgery (e.g., spinal fusion, decompression procedures, screw placement, cage insertion, etc.). This method uses information about the surgery to decide the trajectory and incision site, such as screw size, the angle the screw will be inserted at, and other information. A virtual line is then drawn out from where the drill will be placed during surgery.

In one embodiment, robotic surgical system 10 marks the incision site for a spinal surgical procedure that includes information that cites where the screw needs to be placed, which was determined from a mathematical calculation. This information includes an image, which shows the projected incision site from an algorithm. This makes the incision site more accurate and the process for finding this site more repeatable, regardless of the patient's anatomy.

In one embodiment, robotic surgical system algorithms are to determine where the best incision site is on the patient based on the procedure and where the surgeon's point of interest is. This process will make the incision site more accurate and the process for finding this site more repeatable, regardless of the patient's anatomy. The amount of soft tissue damage that occurs in surgery will also decrease because the algorithm accounts for minimizing tissue damage.

In one embodiment, robotic surgical system 10 uses AI to map where an imaging port should be located on the patient to map the patient's body most effectively. This robotic surgical system considers where the surgeon is planning to make the initial incision on the patient's body to help determine where the imaging port should be located, robotic surgical system 10 re-evaluates where the imaging port should be placed during different steps throughout the procedure.

In one embodiment, robotic surgical system 10 virtualization is provided with a third person perspective of Visualization Device (VD) progress through augmented reality or virtual reality means. The third person perspective of the effort head would be mapped to other medical images used during surgery. This allows the camera 46 point of view to be virtualized, eliminating the need to have a second entry port. This method comprising of a camera 46 that is placed on the end effector 48 itself, which provides a real-time image; and a tracking system shows the position of the Visualization Device (VD) in the patient's body from the outside in real-time. All this real-time data is overlaid on the pre-constructed model, which provides the surgeon with information that allows him or her to dynamically changed the perspective.

In one embodiment, robotic surgical system 10 computer analysis of pre-operative MRI images using AI to identify the patient's abnormality. This information can be used to confirm the position of a robot. This would eliminate wrong level surgery. This is augmented with a method that quantifies the confirmation level of the robot's position, acting as a "confirmation meter." This may include using many sources, such as multiple images at different levels, using pre-operative images, inter-operative images, computer-assisted navigation, and other means, to calculate the accuracy of the robot's position. The higher the position accuracy, the higher the confirmation meter score.

In one embodiment, robotic surgical system 10 Visualization Devices (VD) s constantly interact with the anterior-posterior (AP) view, allowing the surgeon to be constantly looking at Visualization Device (VD) 58. This system is expanded to cover the entirety of the procedure by using the same functionality that allows Visualization Device (VD) 58 to function as a guide wire to locate Visualization Device (VD) 58 inside of the patient as an additional reference point for the surgical navigation program. The configuration of Visualization Device (VD) 58 can be selected based on the instrument to be delivered over it.

In one embodiment, robotic surgical system 10 used AI in which a surgeon identifies the different types of tissues (nerve, ligament, bone, etc.) and how to use different end effectors 48 for each type of tissue. Rules can be added to ensure that specific end effectors 48 can only be used on specific types of tissue (i.e. a drill is only used on bone, or a nerve is only touched with a probe or not allowed to be touched at all). This is applicable to all steps in the process but documented here as multiple tissue types are involved in this specific step.

In one embodiment, robotic surgical system 10 normalizes lighting for probing or imaging system for AI image recognition. Once robotic surgical system 10 identifies specific types of tissue, a normalized lighting process allows robotic surgical system 10 to see the same or similar colors to easily identify previously learned tissues.

In one embodiment, robotic surgical system 10 uses information such as color, texture, and force to what equipment is being utilized in a robotic surgery. Robotic surgical system 10 can understand when enough bone has been worked through to recognize that the surgical robot system 20 should stop using the drill. This is like the concept described in the disclosure, but rather than relying solely on image, robotic surgical system incorporates contact sensors, tissue type sensors (e.g., impedance sensors, optical sensors, etc.), pressure sensors, force sensors, to improve the accuracy of the tissue identification system. Robotic surgical system 10 can analyze signals from the sensors to determine, for example, the force required to continue through the tissue, tissue type, texture the tissue, or the like. Robotic surgical system 10 can perform procedures based, at least in part, on identifying the tissue type and its location.

As a non-limiting example, as a drill or scissors is robotically controlled, the drill or scissors provides sensitive force transducers. These force transducers produce a real-time X, Y, Z force set of data. The data is collected in many successful operations. The real-time images not only have all the previous metatags discussed, but also have the real-time X, Y, Z force data. robotic surgical system can be trained to show the delta force change going from one tissue type to another. As above, the change in force in X, Y, Z can be used to compare to real-time operations. If the tissues are identified correctly and within range, and the forces and changes of force are within range, the images are annotated with virtual information showing that tissues and forces and changes in force are in order. If, however, the forces or changes of force appear out of normal range, alarms would sound, and automated robotic stops would be done to investigate the out of norm situation. With this robotic surgical system, the surgeon can create a "sensitivity" of force change at various parts of the operations, so robotic surgical system may alarm when it approaches a nerve as the force and change of force alarm is set at a more sensitive level than another part of the operation.

As a non-limiting example, robotic surgical system 10 uses biomarkers to communicate with surgical robot 20 where it is during surgery. In one embodiment, robotic surgical system can recognize what type of tissue the surgical robot 20 is touching and then be able to mark the tissue accordingly. Using this robotic surgical system, a surgical robot 20 will be able to recognize what type of tissues it is near and use that information to determine where it is in the patient.

In one embodiment, robotic surgical system 10 uses AR or VR to display where a surgical instrument 18 is being inserted into the patient. The precise display of where the device should be located can be seen by the surgeon during an operation, so the device is accurately placed. The surgical device placement recommendations can be in response to information from AI examination of surgical procedure data, patient data, and postoperative outcomes, to identify correlations between surgical device placement and adverse events, or device placement and positive post-operative outcomes.

In one embodiment, robotic surgical system 10 includes retractor tube that is a part of a surgical robot that vibrates microscopically at a high speed. This would create a wavefront that would allow the tube to insert into the patient's body with greater case. This concept would be augmented using the AI in conjunction with the image recognition system to identify tissue types and adjust the vibration frequency/amplitude based upon correlations identified by the AI between vibration frequencies/amplitudes and positive outcomes/adverse events.

As non-limiting examples, robotic surgical system 10 provides: changing a temperature of the retractor tube (i.e. heating it up or cooling it down) instead of vibration; a hand-held ball-tip probe with sensors located in the robotic arm 54/surgical instrument 18 to determine the position of the probes location for creating a 5D map of a patient selected site; image recognition to show a "point of view" and can use AI pictures compared to a historical database of similar surgeries/operations; captures data from a camera 46 in which the data is uploaded into a historical database to refine and improve robotic surgical system 10 for future surgeries; collects data from pressure sensors on a surgical instrument 18 and data from touch sensors, along with AI to learn; and add to databases; mapping surgical paths for procedures that minimize damage through AI mapping; and the like.

Robotic surgical system 10 can include one or more joints, links, grippers 550, motors, and effector 48 interfaces, or the like. The configuration and functionality of robotic surgical system 10 can be selected based on the procedures to be performed.

In one embodiment, effectors 48 are installed in the robotic system The end effectors 48 can include one or more of: robotic grippers 550; cutting instruments (e.g., cutters, scalpels, or the like), drills; cannulas; reamers; rongeurs; scissors; clamps or the like.

As a non-limiting example, surgeries, processes, and the like can be implemented as computer-readable instructions stored on a computer-readable medium Each of the surgical instruments 18 are manipulated by a "slaved" robotic manipulator and remotely controlled by control signals received from a master control console. As a non-limiting example, surgeon performs surgical procedure on patient P by manipulating input devices at a surgeon console 12. A computer 151 can be used to direct movement of surgical instruments 18, effecting movement of surgical instruments 18 using patient console 16. Arms 54 can be supported by linkages, with a central arm supporting an endoscopic camera 46.

In one embodiment, arms 54 include a positioning portion and a driven portion. The positioning portion of the patient console 16 remain in a fixed configuration during surgery while manipulating tissue. The driven portion of patient console 16 is actively articulated under the direction of surgeon O generating control signals at the surgeon's console 12 during surgery. The actively driven portion of the arms 54 can be referred to as an actuating portion. The positioning portion of the arms 54 that are in a fixed configuration during surgery can be referred to as positioning linkage and/or set-up joint.

As a non-limiting example, a variety of different surgical instruments 18 and equipment can be used, including but not limited to electrosurgical, laser, and the like. Surgical instruments 18 can be used to supply vacuum, gasses, liquids, energy (e.g., electrical, laser, ultrasound), mechanical torques, mechanical push/pull forces, data signals, control signals, etc. to support functions of other types of surgical instruments 18 (e.g., ultrasound, lasers, staplers). As a non-limiting example, a surgical instrument 18 may combine the function of laser cutting and ultrasound together that is supported by a remote-controlled laser generator and a remote-controlled ultrasound generator, both of which can be remotely controlled from surgeon console 12.

In one embodiment, robotic surgical system 10 uses AR or VR to display 20 where a surgical instrument 18 is being inserted into the patient. The precise display of where the device should be located can be seen by the surgeon during an operation, so the device is accurately placed. The surgical device placement recommendations can be in response to information from AI examination of surgical procedure data, patient data, and postoperative outcomes, to identify correlations between surgical device placement and adverse events, or device placement and positive post-operative outcomes.

In one embodiment, robotic surgical system 10 uses one or more AI algorithms of AI system 42. As recited above, as non-limiting examples, AI system 42 can use a variety of different algorithms including but not limited to: supervised learning; classification and regression; decision tree; random forest; support vector machines; Naïve Bayes; linear regression; logistic regression; enhanced imaging; image recognition; treatment planning; risk assessment; robot-assisted navigation; path planning; collision avoidance; autonomous robotics; steady hand assistance; intraoperative decision support; real-time feedback; alert and warning; postoperative monitoring and analysis; prediction; patient outcomes: continuous learning and improvement; data analysis; and the like.

The large amount of data obtained pre-existing data, prior surgeries, current patient anatomy and information, can analyzed by AI algorithms to improve a patient's surgical results, post-operative recovery, pre-operative conditions, pre-operation analysis, and the like, can lead to more opportunities for proactive, modernized, and personalized patient surgeries, recoveries, pre-operation status, and the like. The combination of this information in combination with AI algorithms allows comprehensive information for surgeries.

Machine learning (ML) techniques can combine medical datasets from millions of patients, such as diagnostic profiles, imaging records, and wearable information, to analyze the internal structure of the ocean of medical big data, identify patterns of disease conditions, and overcome the general limitations on access to local datasets. Furthermore, the next-generation healthcare system supported by big data shifts from a centralized hospital-based mode to a parallel mode of monitoring at home, screening and detection at point-of-care testing (POCT), and monitoring during hospitalization, meanwhile, achieves doctor-patient interaction and data transferring via the cloud to case robotic surgery system 10 resources and facilitate personalized surgery.

Figure 25A:
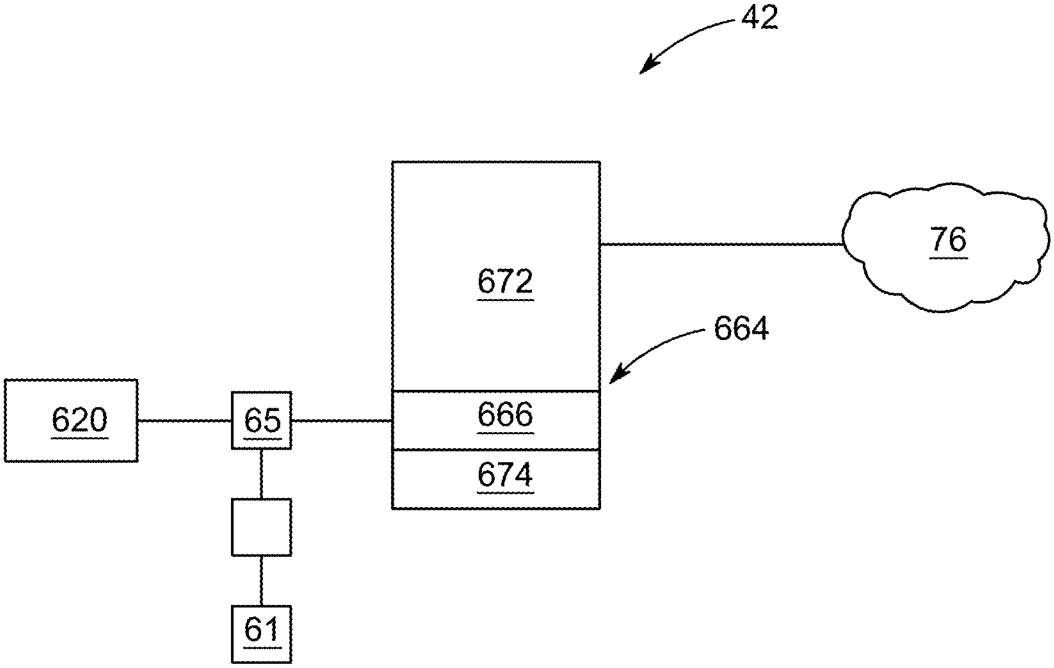
FIGS. 25A and 25B illustrate one embodiment of an AI system used with the present invention.
Figure 25B:
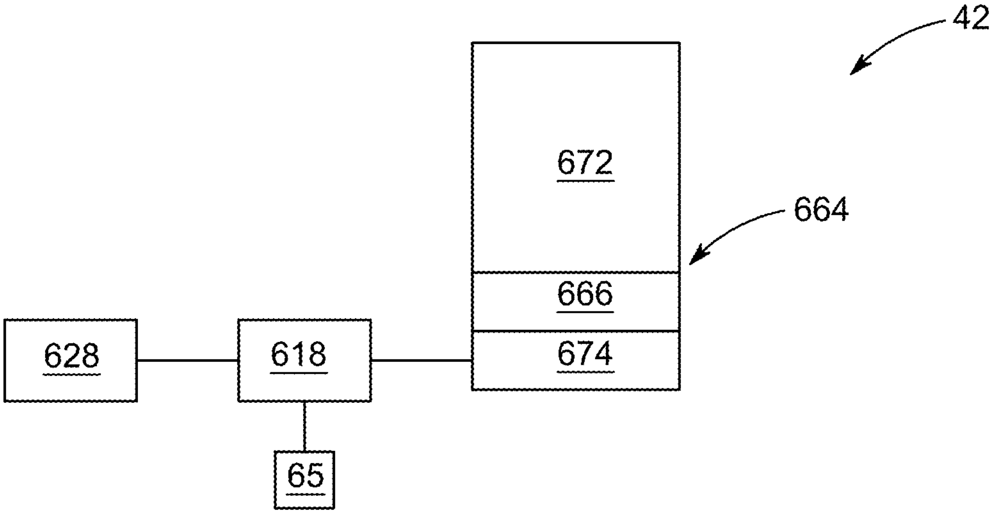
Figure 25C:
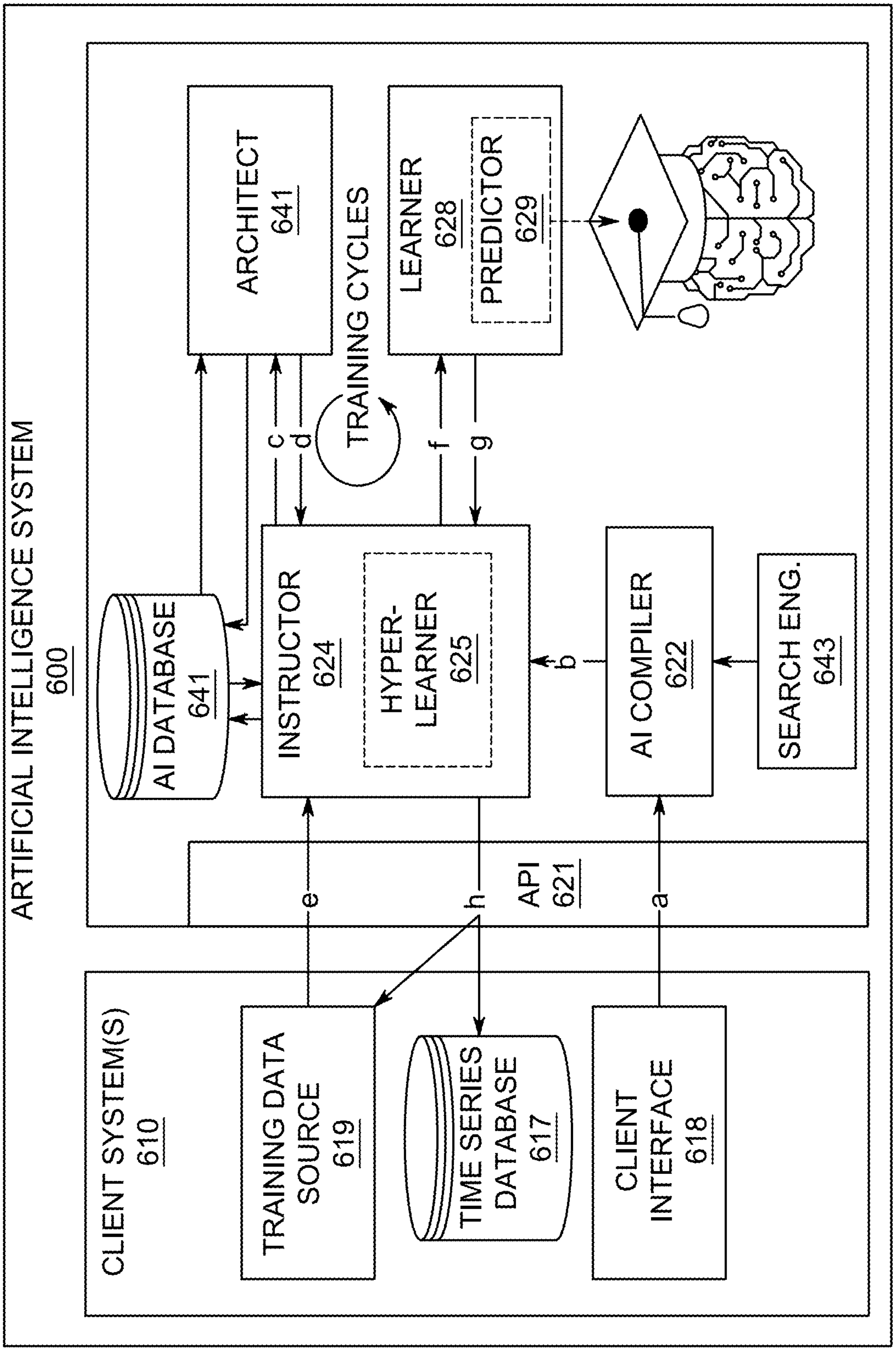
FIG. 25C illustrates a schematic diagram of one embodiment of an AI engine having multiple independent modules on one or more computing platforms of the present invention.
Figure 25D:
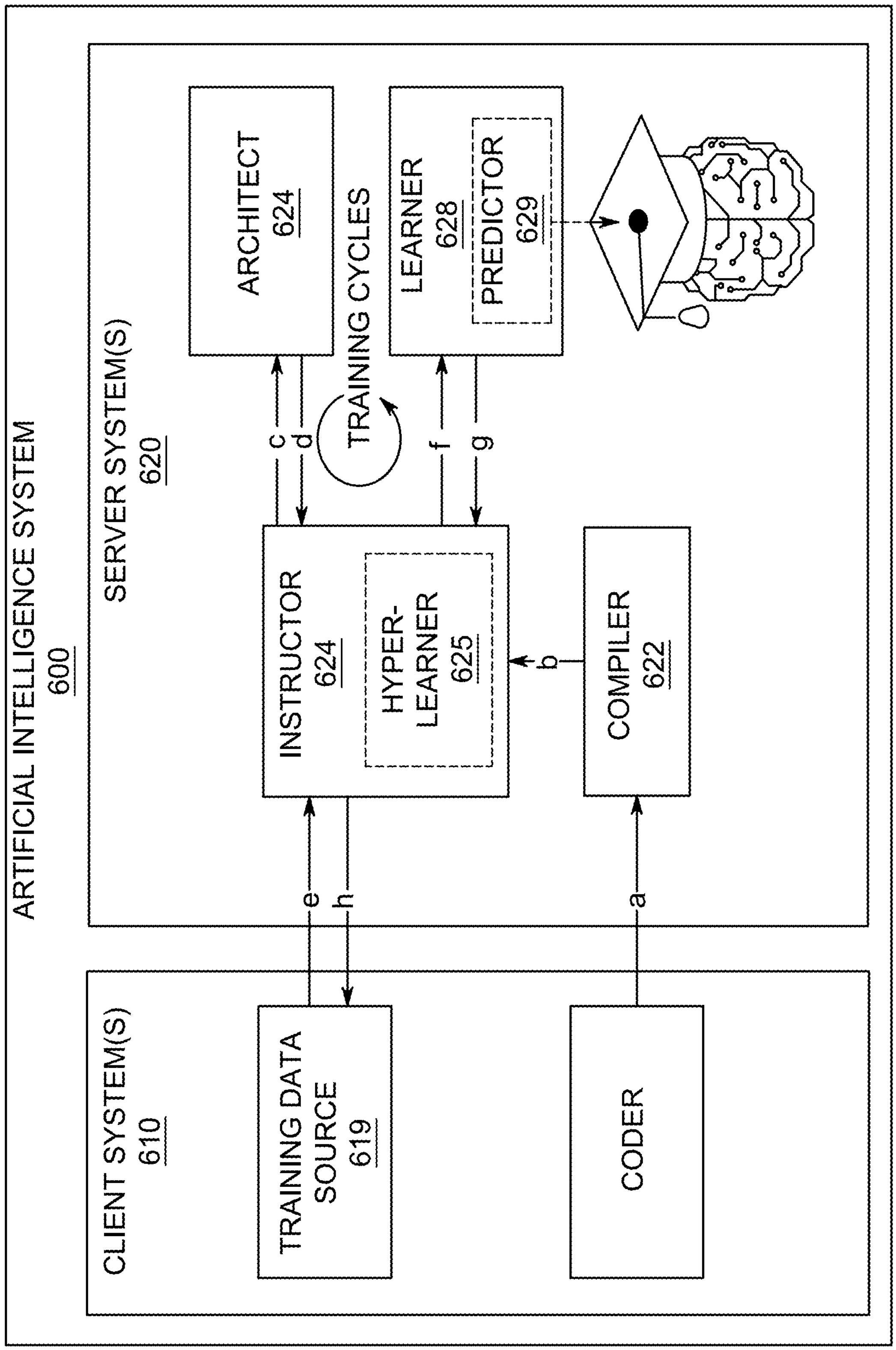
FIG. 25D illustrates a block diagram of an AI engine using one or more modules to create concept nodes in the graph of nodes in one embodiment of the present invention.
Figure 25E:
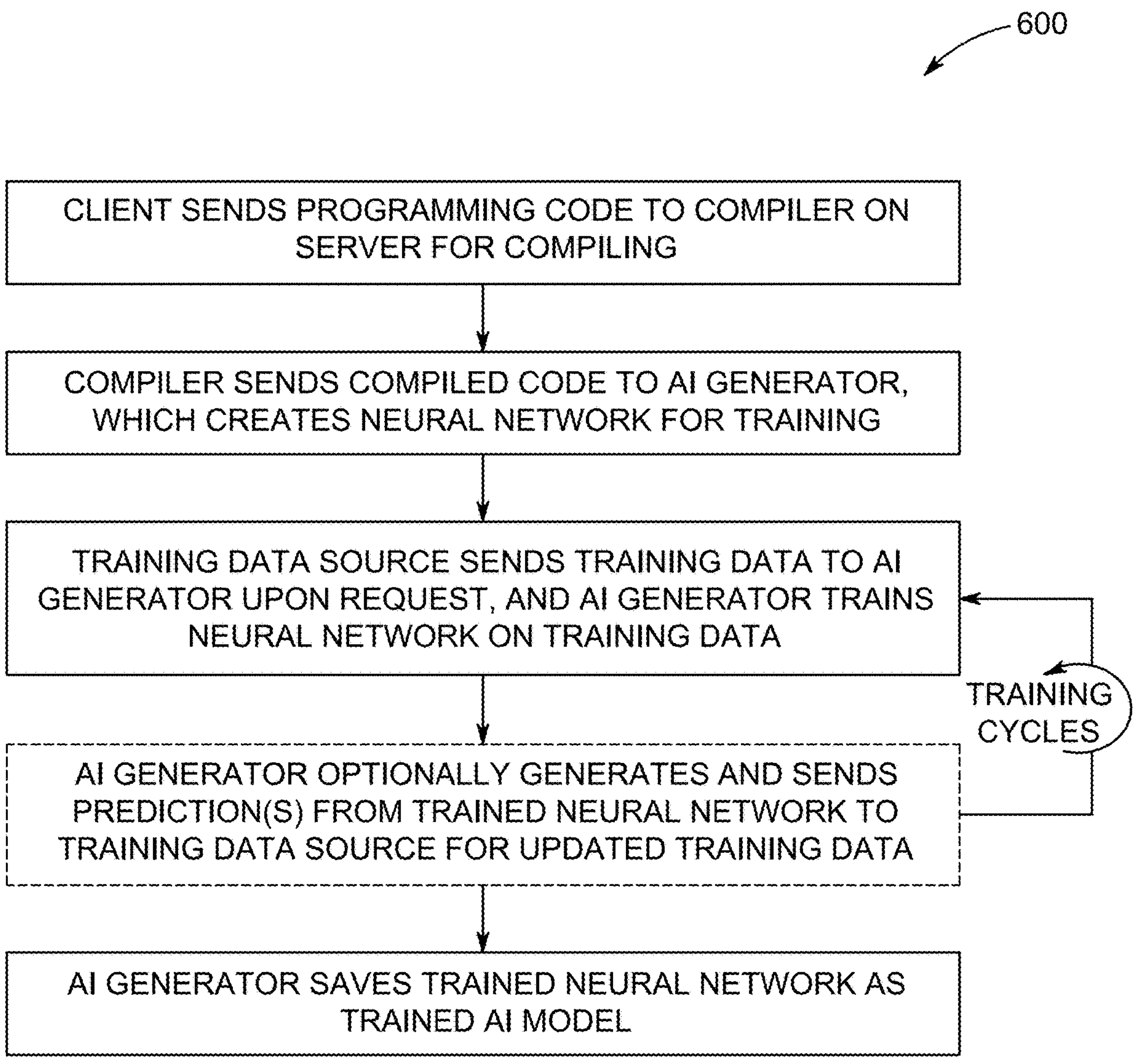
FIG. 25E illustrates one embodiment for a method associated with an AI system of FIGS. 25A through 25E of the present invention.

Referring to FIGS. 25A, 25B, and 25C, in one embodiment, a surgeon and/or assistant can seek from robotic surgery system 10 artificial intelligence from the server and/or an artificial intelligence engine (AI) engine 65. In one embodiment, AI engine 65 makes one or more of the following:

Image and Video Analysis

In one embodiment, enhanced imaging AI algorithms improve the quality and interpretation of medical imaging, providing surgeons with more detailed and accurate information during procedures.

As a non-limiting example, image recognition AI algorithms are used in real-time identification of anatomical structures, tumors, and critical tissues, assisting surgeons, and the like, in making more informed decisions.

Surgical Planning

In one embodiment, treatment planning AI algorithms analyze patient data, medical records, and imaging to assist in creating personalized surgical plans, considering individual variations and optimizing the robotic surgical approach. This is important with abnormal anatomy. Having an integrated overlay of imaging, within the view of the surgeon. This improves surgical accuracy in surgical oncology (particularly with partial nephrectomy or in untangling a tumor from surrounding nerves or blood vessels).

As a non-limiting example, risk assessment AI algorithms are used to predict potential complications, and assess the risks associated with specific procedures. This allows surgeons to make more informed decisions about the best course of action Robot-Assisted Navigation In one embodiment, path planning AI algorithms are used to plan optimal paths for robotic instruments, minimizing invasiveness and reducing the risk of damaging surrounding tissues.

As a non-limiting example, collision avoidance AI algorithms are used for the development of systems that can detect and prevent collisions between robotic instruments and anatomical structures in real-time.

Autonomous Robotics

In one embodiment steady hand assistance AI algorithms provide stability and precision to robotic instruments, compensating for hand tremors and improving the accuracy of movements.

Intraoperative Decision Support

In one embodiment, real-time feedback AI algorithms analyze real-time data from the surgery. This provides surgeons with instant feedback and suggestions to enhance decision-making during the procedure. As a non-limiting example, alert and warning AI algorithms issue alerts if deviations from a planned procedure, or potential issues, are detected. This allows for quick corrective actions. Postoperative Monitoring and Analysis:

In one embodiment, outcome prediction AI algorithms analyze postoperative data to predict patient outcomes and identify factors that contribute to successful surgeries or complications.

Continuous Learning and Improvement

As a non-limiting example, data analysis AI algorithms analyze large datasets of surgical procedures to identify patterns, trends, and best practices, contributing to ongoing improvements in surgical techniques and outcomes.

As a non-limiting example, adaptive systems AI helps develop robotic surgical systems 10 that continuously learn and adapt based on the experiences and feedback from various surgical procedures. This increases efficiency and reproducibility per surgeon.

In one embodiment, artificial intelligence engine 65 contains identifications and profiles of surgeons, assistants or third parties who have posted recommendations/ratings, as well as profiles for patients, surgeons, assistant and third parties, as well as usage feedback for videos and streamed media.

In one embodiment, AI engine 65 receives information from current and part surgeons, current and post assistants. A surgeon seeking to use the artificial intelligence engine 65 is presented (at some time) with a set of questions, or the surgical robotic system 10 obtains data inputs defining the characteristics of the surgeon, assistant or third-party. In this case, the surgeon, assistant or third-party characteristics generally define the context which is used to interpret or modify the basic goal of the surgeon, assistant or third party can define or modify the context at the time of use. Various considerations are used in a cluster analysis, in which recommendations relevant to the contexts may be presented, with a ranking according to the distance function from the "cluster definition." As discussed above, once the clustering is determined, advertisements may be selected as appropriate for the cluster, to provide a subsidy for operation of the system, and to provide relevant information for the surgeon, assistant or third party about available products.

Clustering algorithms partition data into a certain number of clusters (groups, subsets, or categories). Important considerations include feature selection or extraction (choosing distinguishing or important features, and only such features); Clustering algorithm design or selection (accuracy and precision with respect to the intended use of the classification result; feasibility and computational cost; and the like); and to the extent different from the clustering criterion, optimization algorithm design or selection.

Finding nearest neighbors can require computing the pairwise distance between all points. However, clusters and their cluster prototypes might be found more efficiently. If the clustering distance metric reasonably includes close points, and excludes far points, then the neighbor analysis may be limited to members of nearby clusters, thus reducing the complexity of the computation.

There are many situations in which a point could reasonably be placed in more than one cluster, and these situations are better addressed by non-exclusive clustering. In the most general sense, an overlapping or non-exclusive clustering is used to reflect the fact that an object can simultaneously belong to more than one group (class). A non-exclusive clustering is also often used when, for example, an object is "between" two or more clusters and could reasonably be assigned to any of these clusters. In a fuzzy clustering, every object belongs to every cluster with a membership weight. In other words, clusters are treated as fuzzy sets. Similarly, probabilistic clustering techniques compute the probability with which each point belongs to each cluster.

In many cases, a fuzzy or probabilistic clustering is converted to an exclusive clustering by assigning each object to the cluster in which its membership weight or probability is highest. Thus, the inter-cluster and intra-cluster distance function is symmetric. However, it is also possible to apply a different function to uniquely assign objects to a particular cluster.

A well-separated cluster is a set of objects in which each object is closer (or more similar) to every other object in the cluster than to any object not in the cluster. Sometimes a threshold is used to specify that all the objects in a cluster must be sufficiently close (or similar) to one another. The distance between any two points in different groups is larger than the distance between any two points within a group. Well-separated clusters do not need to be spherical but can have any shape.

If the data is represented as a graph, where the nodes are objects and the links represent connections among objects, then a cluster can be defined as a connected component, i.e., a group of objects that are significantly connected to one another, but that have less connected to objects outside the group. This implies that each object in a contiguity-based cluster is closer to some other object in the cluster than to any point in a different cluster.

A density-based cluster is a dense region of objects that is surrounded by a region of low density. A density-based definition of a cluster is often employed when the clusters are irregular or intertwined, and when noise and outliers are present. DBSCAN is a density-based clustering algorithm that produces a partitional clustering, in which the number of clusters is automatically determined by the algorithm. Points in low-density regions are classified as noise and omitted; thus, DBSCAN does not produce a complete clustering.

A prototype-based cluster is a set of objects in which each object is closer (more similar) to the prototype that defines the cluster than to the prototype of any other cluster. For data with continuous attributes, the prototype of a cluster is often a centroid, i.e., the average (mean) of all the points in the cluster. When a centroid is not meaningful, such as when the data has categorical attributes, the prototype is often a medoid, i.e., the most representative point of a cluster. For many types of data, the prototype can be regarded as the most central point. These clusters tend to be globular. K-means is a prototype-based, partitional clustering technique that attempts to find a surgeon, assistant or third party-specified number of clusters (K), which are represented by their centroids. Prototype-based clustering techniques create a one-level partitioning of the data objects. There are a number of such techniques, but two of the most prominent are K-means and K-medoid. K-means defines a prototype in terms of a centroid, which is usually the mean of a group of points and is typically applied to objects in a continuous n-dimensional space. K-medoid defines a prototype in terms of a medoid, which is the most representative point for a group of points and can be applied to a wide range of data since it requires only a proximity measure for a pair of objects. While a centroid almost never corresponds to an actual data point, a medoid, by its definition, must be an actual data point.

In the k-means clustering technique K initial centroids are selected, the number of clusters desired. Each point in the data set is then assigned to the closest centroid, and each collection of points assigned to a centroid is a cluster. The centroid of each cluster is then updated based on the points assigned to the cluster. We iteratively assign points and update until convergence (no point changes clusters), or equivalently, until the centroids remain the same. For some combinations of proximity functions and types of centroids, K-means always converges to a solution, i.e., K-means reaches a state in which no points are shifting from one cluster to another, and hence, the centroids do not change. Because convergence tends to b asymptotic, the end condition may be set as a maximum change between iterations. Because of the possibility that the optimization results in a local minimum instead of a global minimum, errors may be maintained unless and until corrected. Therefore, a human assignment or reassignment of data points into classes, either as a constraint on the optimization, or as an initial condition, is possible.

To assign a point to the closest centroid, a proximity measure is required. Euclidean (L2) distance is often used for data points in Euclidean space, while cosine similarity may be more appropriate for documents. However, there may be several types of proximity measures that are appropriate for a given type of data. For example, Manhattan (L1) distance can be used for Euclidean data, while the Jaccard measure is often employed for documents. Usually, the similarity measures used for K-means are relatively simple since the algorithm repeatedly calculates the similarity of each point to each centroid, and thus complex distance functions incur computational complexity. The clustering may be computed as a statistical function, e.g., mean square error of the distance of each data point according to the distance function from the centroid. Note that the K-means may only find a local minimum, since the algorithm does not test each point for each possible centroid, and the starting presumptions may influence the outcome. The typical distance functions for documents include the Manhattan (L1) distance, Bregman divergence, Mahalanobis distance, squared Euclidean distance and cosine similarity.

An optimal clustering can be obtained as long as two initial centroids fall anywhere in a pair of clusters, since the centroids will redistribute themselves, one to each cluster. As the number of clusters increases, it is increasingly likely that at least one pair of clusters will have only one initial centroid, and because the pairs of clusters are further apart than clusters within a pair, the K-means algorithm will not redistribute the centroids between pairs of clusters, leading to a suboptimal local minimum. One effective approach is to take a sample of points and cluster them using a hierarchical clustering technique. K clusters are extracted from the hierarchical clustering, and the centroids of those clusters are used as the initial centroids. This approach often works well but is practical only if the sample is relatively small, e.g., a few hundred to a few thousand (hierarchical clustering is expensive), and K is relatively small compared to the sample size. Other selection schemes are also available.

In the one embodiment, space requirements for K-means are modest because only the data points and centroids are stored. Specifically, the storage required is $O((m+K)n)$, where m is the number of points and n is the number of attributes. The time requirements for K-means are also modest-basically linear in the number of data points. In particular, the time required is $O(I \times K \times m \times n)$, where I is the number of iterations required for convergence. As mentioned, I is often small and can usually be safely bounded, as most changes typically occur in the first few iterations. Therefore, K-means is linear in m, the number of points, and is efficient as well as simple provided that K, the number of clusters, is significantly less than m.

In the one embodiment, outliers can unduly influence the clusters, especially when a squared error criterion is used. However, in some clustering applications, the outliers should not be eliminated or discounted, as their appropriate inclusion may lead to important insights. In some cases, such as financial analysis, apparent outliers, e.g., unusually profitable investments, can be the most interesting points.

Hierarchical clustering techniques are a second important category of clustering methods. There are two basic approaches for generating a hierarchical clustering: Agglomerative and divisive. Agglomerative clustering merges close clusters in an initially high dimensionality space, while divisive splits large clusters. Agglomerative clustering relies upon a cluster distance, as opposed to an object distance. For example, the distance between centroids or medoids of the clusters, the closest points in two clusters, the further points in two clusters, or some average distance metric. Ward's method measures the proximity between two clusters in terms of the increase in the sum of the squares of the errors that results from merging the two clusters.

Agglomerative Hierarchical Clustering refers to clustering techniques that produce a hierarchical clustering by starting with each point as a singleton cluster and then repeatedly merging the two closest clusters until a single, all-encompassing cluster remains. Agglomerative hierarchical clustering cannot be viewed as globally optimizing an objective function. Instead, agglomerative hierarchical clustering techniques use various criteria to decide locally, at each step, which clusters should be merged (or split for divisive approaches). This approach yields clustering algorithms that avoid the difficulty of attempting to solve a hard combinatorial optimization problem. Furthermore, such approaches do not have problems with local minima or difficulties in choosing initial points. Of course, the time complexity of O(m2 log m) and the space complexity of O(m2) are prohibitive in many cases. Agglomerative hierarchical clustering algorithms tend to make good local decisions about combining two clusters since they can use information about the pair-wise similarity of all points. However, once a decision is made to merge two clusters, it cannot be undone at a later time. This approach prevents a local optimization criterion from becoming a global optimization criterion.

In supervised classification, the evaluation of the resulting classification model is an integral part of the process of developing a classification model. Being able to distinguish whether there is non-random structure in the data is an important aspect of cluster validation.

In one embodiment, a k-means algorithm is used as follows:

The K Means Clustering algorithm finds observations in a dataset that are like each other and places them in a set. The process starts by randomly assigning each data point to an initial group and calculating the centroid for each one. A centroid is the center of the group. Note that some forms of the procedure allow you to specify the initial sets.

Then the algorithm continues as follows: it evaluates each observation, assigning it to the closest cluster. The definition of "closest" is that the Euclidean distance between a data point and a group's centroid is shorter than the distances to the other centroids.

When a cluster gains or loses a data point, the K means clustering algorithm recalculates its centroid. The algorithm repeats until it can no longer assign data points to a closer set.

When the K means clustering algorithm finishes, all groups have the minimum within-cluster variance, which keeps them as small as possible. Sets with minimum variance and size have data points that are as similar as possible. There is variability amongst the characteristics in each cluster, but the algorithm minimizes it.

In the one embodiment, the observations within a set should share characteristics. In some cases, the analysts might need to specify different numbers of groups to determine which value of K produces the most useful results.

In one embodiment, an artificial intelligence engine 65 is used to predict what will happen; or prescriptive, meaning using data to make suggestions about what action to take. As a nonlimiting example, AI provides predictive information about a patient's health.

As a non-limiting example, AI engine 65 is used for systems with a deep learning network with many layers. The layered network can process extensive amounts of data and determine the "weight" of each link in the network for example, in an image recognition system, some layers of the neural network might detect individual features of a face, like eyes, nose, or mouth, while another layer would be able to tell whether those features appear in a way that indicates a face.

In the one embodiment, there are many different AI engines 65 that can be trained to generate suitable output values for a range of input values; the neuro-fuzzy logic engine 65 is merely one embodiment.

In the one embodiment, measurement data, the information feeds, and the output parameters may be used to train an AI engine 65 to control the one or more devices in response to the measurement data and information feeds. In one embodiment, AI engines 65 can be trained to recognize temporal patterns.

In one embodiment, measurement data, the information feeds, and the output parameters may be used to train an AI engine 65 to control the one or more devices in response to the measurement data and information feeds.

In one embodiment, illustrated in FIGS. 25A through 25E a computing system 664 includes a logic subsystem 666 and a storage subsystem 668. Computing system 664 may further include an input subsystem 670, an output subsystem 672, a communication subsystem 674, and/or other components not shown in FIGS. 25A through 25E In the one embodiment, logic subsystem 666 may include one or more physical logic devices configured to execute programmed instructions 667 of surgical computing device 151. For example, the logic subsystem 666 may be configured to execute programmed instructions 67 of surgical computing device 151 that are part of one or more applications, services, programs, routines, libraries, objects, components, data structures, or other logical constructs. Such programmed instructions 67 of surgical computing device 151 may be implemented to perform a task, implement a data type, transform the state of one or more components, achieve a technical effect, or otherwise arrive at a desired result.

In the one embodiment, logic subsystem 666 includes one or more processors 62 (as an example of physical logic devices) configured to execute software programmed instructions 67 of surgical computing device 151. Additionally, or alternatively, the logic subsystem 666 may include one or more hardware and/or firmware logic machines (as an example of physical logic devices) configured to execute hardware or firmware programmed instructions 67 of surgical computing device 151. Processors 62 of the logic subsystem may be single-core or multi-core, and the programmed instructions 67 of surgical computing device 151 executed thereon may be configured for sequential, parallel, and/or distributed processing. Individual components of the logic subsystem may be distributed among two or more separate devices, which may be remotely located and/or configured for coordinated processing. Aspects of the logic subsystem may be virtualized and executed by remotely accessible, networked computing devices configured in a cloud-computing configuration.

In the one embodiment, storage subsystem 668 includes one or more physical, non-transitory memory devices configured to hold programmed instructions 67 of surgical computing device 151 executable by the logic subsystem in non-transitory form, to implement the methods and processes described herein. When such methods and processes are implemented, the state of storage subsystem 68 may be transformed. e.g., to hold different data. Storage subsystem 68 may include removable and/or built-in devices. Storage subsystem 668 may include optical memory devices, semiconductor memory devices, and/or magnetic memory devices, among other suitable forms. Storage subsystem 668 may include volatile, nonvolatile, dynamic, static, read/write, read-only, random-access, sequential-access, location-addressable, file-addressable, and/or content-addressable devices. Aspects of logic subsystem 666 and storage subsystem 68 may be integrated together into one or more hardware-logic components. While storage subsystem 668 includes one or more physical devices, aspects of the programmed instructions 67 of surgical computing device 151 described herein alternatively may be propagated by a communication medium (e.g., an electromagnetic signal, an optical signal, etc.) that is not necessarily held by a physical device for a finite duration.

In one embodiment, an AI generator 623 generates the trained neural network 606 and can include one or more AI-generator modules selected from at least an instructor module 624, an architect module 626, and a learner module 628. The instructor module 624, the architect module 626, and the learner module 628 can respectively be referred to herein as the Instructor, the Architect, and the Learner. The instructor module 624 can optionally include hyperlearner module 625, which can be referred to herein as the hyperlearner, and which can be configured to select one or more hyperparameters for any one or more of a neural network configuration, a learning algorithm, a learning optimizer, and the like. Before selecting the one or more hyperparameters, the hyperlearner module 625 can access a database of solution statistics gathered from one or more repositories of previous problems and previously built AI models therefor and take a fingerprint of a sample of available data by using random predictions. The hyperlearner module 625 can optionally be contained in a different AI-generator module such as the architect module 626 or the learner module 628, or the hyperlearner module 625 can be an AI-generator module itself. The learner module 628 can optionally include a predictor module 629, which can be referred to herein as the Predictor, and which can provide one or more predictions for a trained neural network such as the trained neural network 106 hosted in a prediction mode. The predictor module 629 can optionally be contained in a different AI-generator module such as the instructor module 624 or the architect module 326, or the predictor module 629 can be an AI-generator module itself. The AI generator 623 including the foregoing one or more AI-generator modules can be configured to generate the trained neural network from compiled code via one or more training cycles in the AI generator 623.

In the one embodiment, an AI database, such as AI database 741, hosted on cloud platform 76 is configured to cooperate with AI engine 65. In an embodiment, the AI database stores and indexes trained AI objects, and its class of AI objects have searchable criteria. The AI database cooperates with AI search engine 65 to utilize search criteria supplied from a surgeon, assistant or third party, from one or more of: scripted software code; and data put into defined fields of a surgeon, assistant or third party interface 61 can search engine 65 utilizes the search criteria in order for AI search engine 65 to retrieve one or more AI data objects that have already been trained as query results. The AI database is coupled to AI engine 65 to allow any of reuse, reconfigure ability, and recomposition of the one or more trained AI data objects from the AI database into a new trained AI model. These and other features of the design provided herein can be better understood with reference to the drawings, description, and claims, all of which form the disclosure of this patent application.

In one embodiment, a surgeon or assistant can search the database, that can be a medical device database based on one or more of the surgical procedures to be performed, the anatomical characteristics, and the surgical instrument kinematics using the above-described metadata to identify structural relationships for the video and information of interest. Additionally, in one aspect, the surgical planning tool includes a computer-based morphology matching and analysis algorithm. In one aspect, the morphology matching algorithm is selected through videos stored on an electronic medical records database to identify correlations between visual characteristics in the video records and associated metadata identifications made by medical personnel. The surgical planning tool can apply these correlations to newly encountered anatomical structures to help medical personnel performing the procedure determine patient anatomy, preferred surgical approaches, disease states, potential complications, and the like.

In one embodiment, a surgeon or assistant can search the database, that uses a morphology matching algorithm and look for recorded motion map image information and optionally kinematic information to identify correlations between anatomical features (such as geometry) and instrument motion. This morphology can be useful, for example, to identify various anatomical features associated with various instrument motions. This modality can also be useful, for example, to identify various anatomical features that are not associated with various instrument motions. For example, this morphological information can be used as a basis for generating surgical guidance to present to the surgeon during surgery. For example, this morphological information can be used as a basis for arresting or imparting certain surgical instrument motion to the surgical procedure during the surgical procedure.

In one embodiment, a morphology matching algorithm is coupled to the database, and can access recorded motion map image information to identify correlations between anatomical features (such as geometry) and reactive forces imparted by tissue structures in response to touches by the surgical instrument. This modality can be useful, for example, to identify correlations between visualized anatomical tissue structures and tactile feedback imparted by the tissue structures in response to palpation by a robotically assisted instrument. In some embodiments, the correlated motion map image morphology and tactile feedback information is associated with an expert surgeon diagnostic assessment used in surgeon training.

In one embodiment, a surgeon or assistant can search the database with relevant information of one or more of the surgical procedures to be performed. In one embodiment, the database can include past procedures information of third parties and/or the patient, including electronic medical records, imaging data, and the like.

In one embodiment, a surgeon or assistant can search the database and includes relevant information of a surgical procedure to be performed the surgeon can define the tissue as the desired type, and the database can include image recognition information that can be updated and the robot 20 proceeds.

In one embodiment, a surgeon or assistant can search the database and utilize AI to operate one or more surgical robot systems 10, an AI guidance system, an image recognition system, an image recognition database, and/or a database of past procedures, electronic medical records, and/or imaging data. The image recognition system may identify the tissue type present in the patient. If it is the desired or targeted tissue type, the AI guidance system may remove that tissue using an end effector on the surgical robot. The surgeon can define the tissue type if the image recognition system identified the tissue as anything other than the desired tissue type to perform a procedure. The system can identify anatomical features, abnormalities, tissue margins, tissue characteristics, tissue types, tissue interfaces, or combinations thereof based on, for example, preset criteria, physician input, etc. For example, the image recognition system can evaluate images to identify landmarks and generate a surgical plan based, at least in part, on those landmarks. The landmarks can be identified by the system, physician, or both. In some procedures, the landmarks can be identifiable anatomical features (e.g., spinous processes, bony protrusions, facet joints, nerves, spinal cord, intervertebral disc, vertebral endplates, etc.) along the patient's spine to generate a surgical plan.

Robotic surgical system 10 and methods can use images obtained prior to and/or during surgery to guide a robotic surgical apparatus, end effector, surgical tool, or the like. Robotic surgical system 10 can access a database to that has information covering the entirety of a surgical procedure.

Robotic surgical system 10, and methods, can monitor a patient's brain activity during surgery to determine a level of consciousness, patient response during a procedure, or the like. For example, using of a wireless EEG system during surgery can provide a basis for determining the amount of medication to give a patient. The EEG can track the amount of discomfort the patient is experiencing, and more medication (i.e., anesthesia) can be administered if the amount of discomfort exceeds a threshold. The system can include an AI unit that receive monitored brain activity data (e.g., brain activity patterns, brain activity spikes, and the like.) and identify correlations with anesthesia based adverse events. Pain, discomfort, and other patient parameters can be monitored and evaluated to determine whether to modify the treatment plan, administer anesthesia, etc. The AI/machine learning can be used to analyze brain activity, patient feedback, or other patient parameters to, for example, improve safety, comfort, or the like.

Robotic surgical system 10 and methods can access the database for measurement of various parameters in a database, associated with an end effector before, during, and/or after a surgical action or procedure. The monitored parameters can include rpms, angle, direction, sound, or the like. The monitored parameters can be combined with location data, tissue type data, and/or metadata to train an AI system 42 for guiding a robotic surgical tool to automatically perform a surgical action, procedure, or an entire surgery.

Robotic surgical system 10 and methods can access the database and be implemented in a computing system for at least partially controlling a robotic surgical apparatus to perform surgical actions by obtaining a first image of a region of interest associated with a subject. A type of tissue shown in the first image can be identified based, at least in part, on a neural network model trained on an image training set. In response to determining that the identified type of tissue belongs to a set of targeted types, causing the robotic surgical apparatus to perform a first surgical action with respect to the region of interest in accordance with a surgical plan. A second image of the region of interest can be obtained after completion of the first surgical action. Additionally surgical steps can be performed.

In one embodiment, robotic surgical system 10 can access a computer-readable storage medium storing content that, when executed by one or more processors 62, causes the one or more processors 62 to perform actions including obtaining first image of a region of interest associated with a surgery subject, and identifying a type of tissue shown in the first image based, at least in part, on a neural network model. In response to determining that the identified type of tissue belongs to a set of targeted types, robotic surgical apparatus performs a first surgical action with respect to the region of interest in accordance with a surgical plan. A second image of the region of interest is obtained after completion of the first surgical action. The actions can include displaying types of tissue comprises displaying one or more boundary indicators for indicating at least one of targeted tissue to be removed, protected tissue, delivery instrument placement, or an end effector working space within the subject.

In general, AI database stores and indexes trained AI objects, and its class of AI objects have searchable criteria. AI database cooperates with search engine 65 to utilize search criteria supplied from a surgeon, assistant or third party to retrieve one or more AI data objects that have already been trained as query results. The AI database is coupled to AI engine 65 to allow any of reuse, reconfigure ability, and recomposition of the one or more trained AI data objects from the AI database into a new trained AI model.

In one embodiment, AI engine 65 (600) includes multiple independent modules on one or more computing platforms, where the architect module is configured to create one or more concept nodes by wrapping each external entity of code into a software container with an interface configured to exchange information in a protocol of a software language used by that external entity of code in accordance with an embodiment.

As shown, the AI system 42 (600) includes one or more client systems 610 and one or more server systems 620, wherein each server system or any two or more servers' systems of the one or more server systems 620 can be referred to herein as an AI engine 65. The one or more client systems 610 can be client systems and include a coder 612 or coding means for generating programming code such as programming code in a pedagogical programming language (e.g., Inkling™). The one or more client systems 610 can further include a training data source 614. As a non-limiting example, the training data source 614 can alternatively be included in the one or more server systems 620, or the training data source 614 can be include in both the one or more client systems 610 and the one or more server systems 620. The one or more server systems 620 can be server systems and include a compiler for the programming code and an AI generator 623 for generating the trained neural network via one or more training cycles in the AI generator 623.

One or more client systems 610 and the one or more server systems 620, it should be understood that the one or more client systems 610 and the one or more server systems 620 need not be deployed exactly as shown or with local and remote systems tele communicatively coupled over substantially large geographic distances. The one or more client systems 610, the one or more server systems 620, or one or more components thereof can be deployed at a single geographic location such as in a building or room of the building. Moreover, the one or more client systems 610 and the one or more server systems 620 can be deployed in a single system such as a powerful, single-enclosure machine. As used herein, the foregoing refers to so-called on-premises installations, which is another operating environment for building AI, training AI, deploying AI, or a combination thereof.

In an embodiment, other independent processes cooperate together and contain functionality from the instructor module, the learner module, etc. For example, a scholar process is coded to handle both the training for a given concept (lesson management) and training a lesson. The scholar process trains a given concept (e.g. does the job of instructor and learner in an alternative architecture). When the AI engine 65 trains the same concept or multiple different concepts in parallel then the AI engine 65 will have multiple scholars running in parallel. A director module manages the training of a concept graph. A conductor process merely manages resource allocation required for training an AI model. The director module determines how the resources are used to train the graph of nodes in parallel. Each concept is trained by a scholar process and in the case of multiple concepts being trained in parallel multiple scholar processes are run simultaneously. This is all managed by the director module.

Figure 26A:
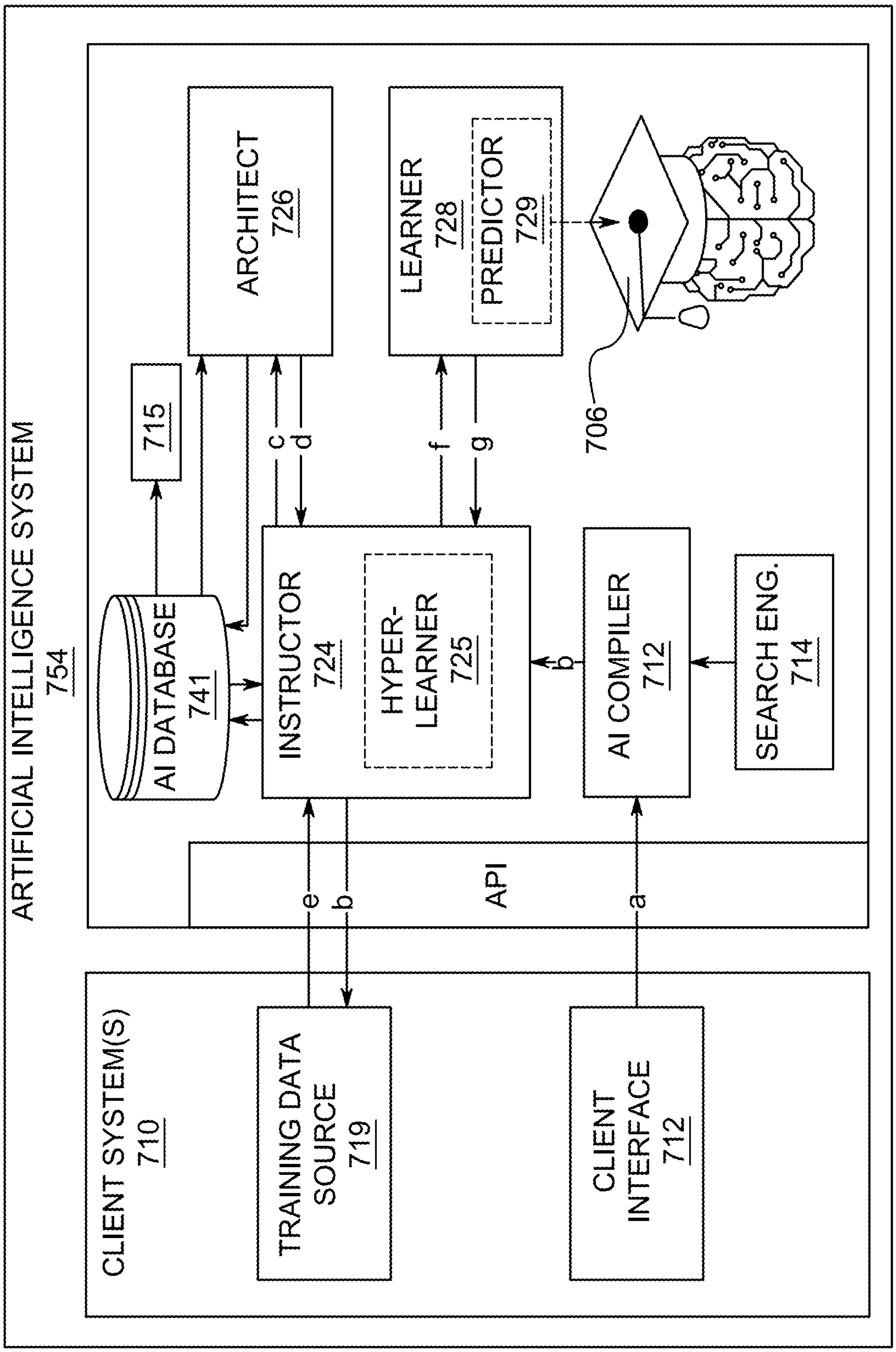
FIG. 26A illustrates one embodiment of an artificial intelligence system of the present invention.
Figure 26B:
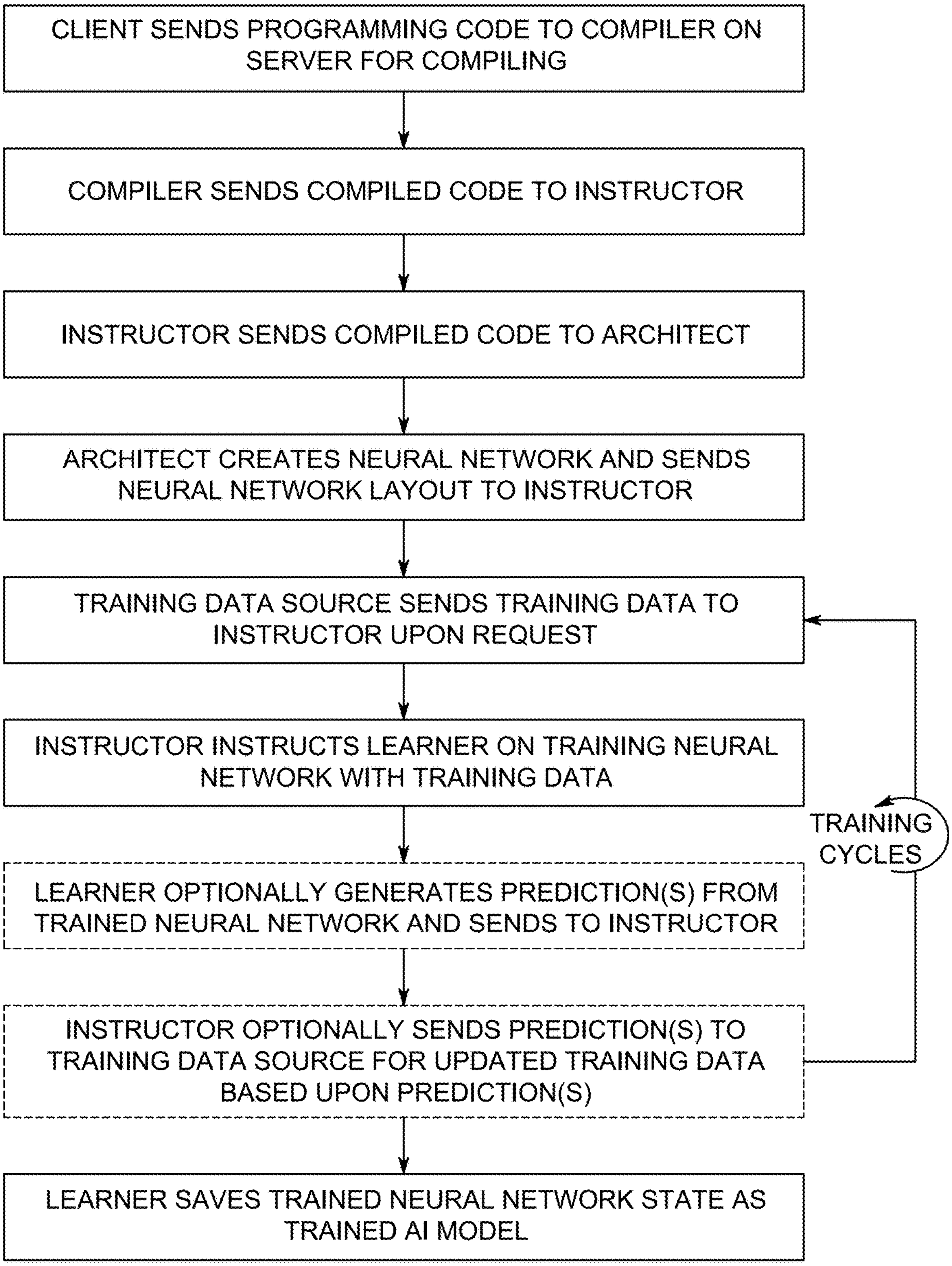
FIG. 26B is a block diagram illustrates an embodiment of a method using the FIG. 26A AI system of the present invention.

As illustrated in FIGS. 26A and 26B in response to received data, the AI database 741 stores and indexes trained AI objects, and the class of AI objects have searchable criteria. The AI database 741 of searchable AI objects indexes parameters and characteristics known about the AI objects that allows searching of surgeon, assistant or third party supplied criteria from either or both of: scripted code and defined fields in a surgeon, assistant or third-party interface.

In the one embodiment, AI engine 65 utilizes this search criteria supplied from the current or past surgeons and current and past surgeons, current and past algorithms, newly or partially created algorithms. This is achieved through scripted software code, data put into defined fields of a surgeon, assistant or third-party interface, and the like, in order for AI engine 65 to find and retrieve relevant AI data objects that have already been trained as query results. In 0 . . . itself, because the untrained model has not yet been trained. In the one embodiment, engine 65 use of the surgeon, assistant or third party supplied search criteria from the surgeon, assistant or third-party interfaces to find relevant trained AI objects stored in the AI data will be described in more detail later.

AI database can index AI objects corresponding to the main concept and the set of sub concepts making up a given trained AI model so that reuse, recomposition, and reconfiguration of all or part of a trained AI model is possible.

AI database 741 can be also coupled to AI engine 65 to allow any of reuse, reconfigure ability, and recomposition of the one or more trained AI data objects into a new trained AI model. As a non-limiting example, AI engine 65 can generates AI models, such as a first AI model. The AI database 741 may be part of and cooperate with various other modules of AI engine 65. In one embodiment, AI engine 65 has a set of surgeon, assistant or third party interfaces 112 to import from either or both 1) scripted software code written in a pedagogical software programming language, such as Inkling, and/or 2) from the surgeon, assistant or third party interface 712 with defined fields that map surgeon, assistant or third party supply criteria to searchable criteria of the AI objects indexed in AI database 741

AI database 741 can be part of cloud-based AI service. AI database 741 can be hosted on cloud platform with the search engine 715 (65).

As a non-limiting example, AI database 741 cooperates with AI engine 65. AI engine 65 can further include an architect module 126, an instructor module 124, and a learner module 128. In the one embodiment, architect module 126 creates and optimizes learning topologies of an AI object, such as the topology of a graph of processing nodes, for the AI objects. The instructor module 724 carries out a training plan codified in a pedagogical software programming language. The learner module 728 carries out an actual execution of the underlying AI learning algorithms during a training session. The architect module 726, when reconfiguring or recomposing the AI objects, composes one or more trained AI data objects into a new AI model and then the instructor module 724 and learner module 728 cooperate with one or more data sources to train the new AI model.

Surgeon, assistant or third-party interface, to the AI database 741 and search engine 715, can be configured to present a population of known trained AI objects. In the one embodiment, search engine 715 cooperates with the AI database 741 is configured to search the population of known trained AI objects to return a set of one or more already trained AI objects similar to a problem trying to be solved by the surgeon, assistant or third party supplying the search criteria.

The database management system tracking and indexing trained AI objects corresponding to concepts is configured to make it easy to search past experiments, view results, share with others, and start new variants of a new trained AI model.

In the one embodiment, AI database 741 may be an object orientated database, a relational database, or other similar database, that stores a collection of AI objects (i.e., the trained main concept and sub concepts forming each trained AI model). The AI database 741 can be composed of a set of one or more databases in which each database has a different profile and indexing, where the set of databases are configured to operate in a parallel to then send back accurate, fast, and efficient returns of trained AI objects that satisfy the search query.

In the one embodiment, AI engine 65 generates a trained AI model 706 and can include one or more AI-generator modules selected from at least an instructor module 724, an architect module 726, and a learner module 728 as shown. The instructor module 724 can optionally include a hyperlearner module 725, and which can be configured to select one or more hyperparameters for any one or more of a neural network configuration, a learning algorithm, a learning optimizer, and the like. The hyperlearner module 725 can optionally be contained in a different AI-generator module such as the architect module 726 or the learner module 728, or the hyperlearner module 725 can be an AI-generator module itself. The learner module 732 can optionally include a predictor module 729, which can provide one or more predictions for a trained AI model. The predictor module 729 can optionally be contained in a different AI-generator module such as the instructor module 724 or the architect module 726, or the predictor module 729 can be an AI-generator module itself. AI engine 65 can generate the trained AI model 706, such as trained AI model 706, from compiled scripted software code written in a pedagogical software programming language via one or more training cycles with AI engine 65.

One or more surgeons, assistants and the like 710 can make a submission to create a trained AI model. Once a Mental Model and Curricula have been coded in the pedagogical software programming language, then the code can be compiled and sent to the three main modules, the learner module 728, the instructor module 724, and the architect module 726 of AI engine 65 for training. One or more surgeon, assistant or third-party interfaces 712, such a web interface, a graphical surgeon, assistant or third-party interface, and/or command line interface, will handle assembling the scripted code written in the pedagogical software programming language, as well as other ancillary steps like registering the line segments with AI engine 65, together with a single command. However, with each module of the AI compiler module 722, the web enabled interface to AI engine 65, the learner module 728 be used in a standalone manner, so if the author prefers to manually invoke the AI compiler module, manually perform the API call to upload the compiled pedagogical software programming language to the modules of AI engine 65, and the like As a non-limiting example, one or more clients 710 can send scripted code from a coder 712 or another surgeon, assistant or third-party interface to AI compiler 722. AI compiler 722 compiles the scripted software code written in a pedagogical software programming language. AI compiler 722 can send the compiled scripted code, similar to an assembly code, to the instructor module 724, which, in turn, can send the code to the architect module 726. In one embodiment, AI compiler 222 can send the compiled scripted code in parallel to all of the modules needing to perform an action on the compiled scripted code. The architect module 726 can propose a vast array of machine learning algorithms, such as various neural network layouts, as well as optimize the topology of a network of intelligent processing nodes making up an AI object. The architect module 726 can map between concepts and layers of the network of nodes and send one or more instantiated AI objects to the learner module 728. Once the architect module 726 creates the topological graph of concept nodes, hierarchy of sub concepts feeding parameters into that main concept (if a hierarchy exists in this layout) and learning algorithm for each of the main concept and sub concepts, then training by the learner module 728 and instructor module 724, which can be couped to a hyper learner 725, can begin.

The instructor module 724 can request training data from the training data source 219. Training can be initiated with an explicit start command in the pedagogical software programming language from the surgeon, assistant or third party to begin training. In order for training to proceed, the surgeon, assistant or third party needs to have already submitted compiled pedagogical software programming language code and registered all of their external data sources such as simulators (if any are to be used) via the surgeon, assistant or third-party interfaces with the learner and instructor modules 724, 726 of AI engine 65.

The training data source 719 can send the training data to the instructor module 724 upon the request. The instructor module 724 can subsequently instruct the learner module 728 on training the AI object with pedagogical software programming language-based curricula for training the concepts into the AI objects. Training an AI model 706 can take place in one or more training cycles to yield a trained state of the AI model 706. The instructor module 724 can decide what pedagogical software programming language-based concepts and streams should be actively trained in a mental model. The instructor module 724 can know what the terminating conditions are for training the concepts based on surgeon, assistant or third-party criteria and/or known best practices. The learner module 728 or the predictor 729 can elicit a prediction from the trained AI model 706 and send the prediction to the instructor module 724. The instructor module 724, in turn, can send the prediction to the training data source 719 for updated training data based upon the prediction and, optionally, instruct the learner module 328 in additional training cycles. When the one or more training cycles are complete, the learner module 728 can save the trained state of the network of processing nodes in the trained AI model 706. (Note a more detailed discussion of different embodiments of the components making up AI engine 65 occurs later.)

The AI database 741 may consist of a storage layer which is configured to know how to efficiently store database objects, in this case AI objects, an indexing mechanism to speed retrieval of the stored AI objects, engine 715 to translate a query request into a retrieval strategy to retrieve AI objects that satisfy a query, and a query language which describes to the AI database 741 what AI objects are desired to be retrieved.

As a non-limiting example, search engine 715 is configured to parse scripted software code written in a pedagogical software programming language and then map that to one or more searchable criteria as well as 2) import the data put into defined fields of the surgeon, assistant or third party interface to use as searchable criteria to find relevant trained AI objects indexed in the AI database 741. In an embodiment, the search engine 715 is configured to also be able to do a natural language search of a submitted description from a surgeon, assistant or third party to determine what a similar trained object would be by referencing the: indexed criteria and/or signatures and/or example models in the database.

In one embodiment, AI database 741 is indexed with keywords and problems solved about each stored AI object In one embodiment, search engine 715 in query results will return relevant AI objects. The relevant AI objects can be evaluated and return based on a number of different weighting factors including number of resources consumed to train that concept learned by the AI object In one embodiment, search engine 715 information from the current surgeon, prior surgeons who have performed similar surgeries, assistants, prior assistants, can provide information for relevant trained AI objects. In an embodiment, search engine 743 refers to: the signatures of the stored AI objects as well as; any indexed parameters for the AI objects indexed by the AI database 741.

In an embodiment, the AI database 741 and search engine 715 build an index of algorithms and parameters that have been tried in past.

Figure 27:
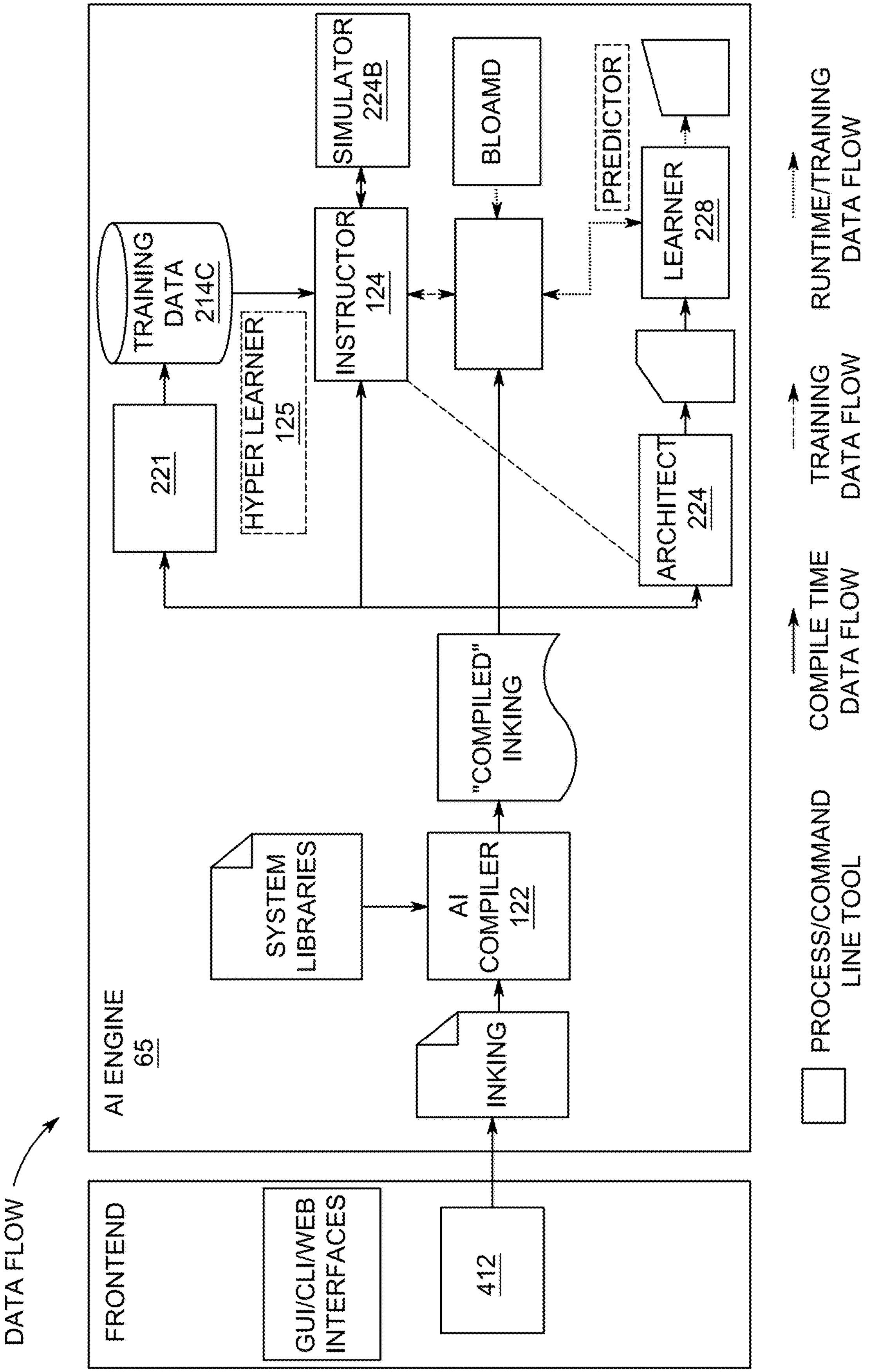
FIG. 27 provides a block diagram of an AI engine using an interface infrastructure to allow uploading of user code and data from their local development environment into the AI engine learning framework, via the user files specified in a file, such as a project file, associated with the container in accordance with an embodiment.
Figure 28:
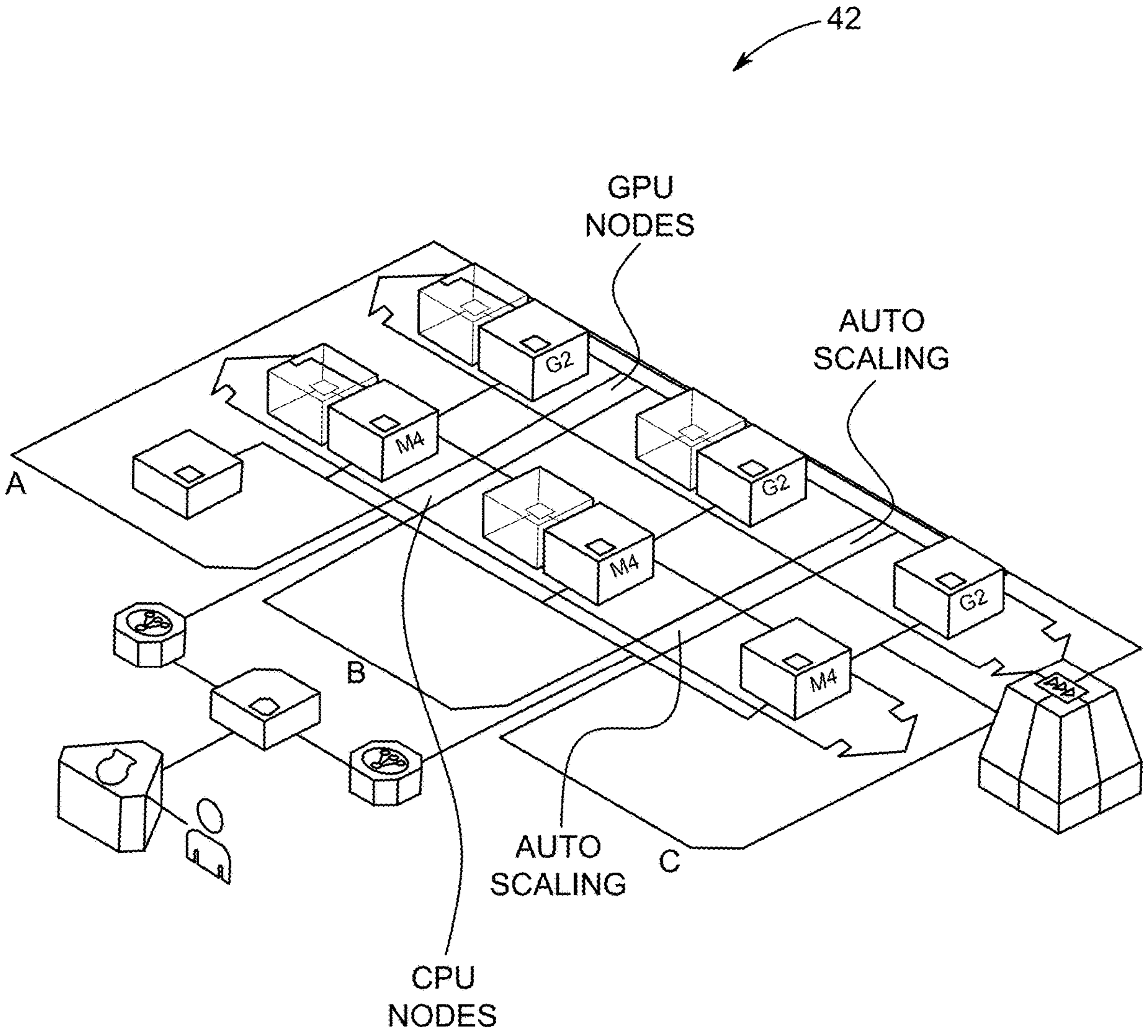
FIG. 28 provides a block diagram illustrating an AI system and its cloud-based computing platforms infrastructure in accordance with an embodiment.

FIG. 27 shows the architect module configured to propose a neural network layout such as the neural network layout and the learner module configured to save a trained state of a neural network such as the trained neural network.

Figure 29:
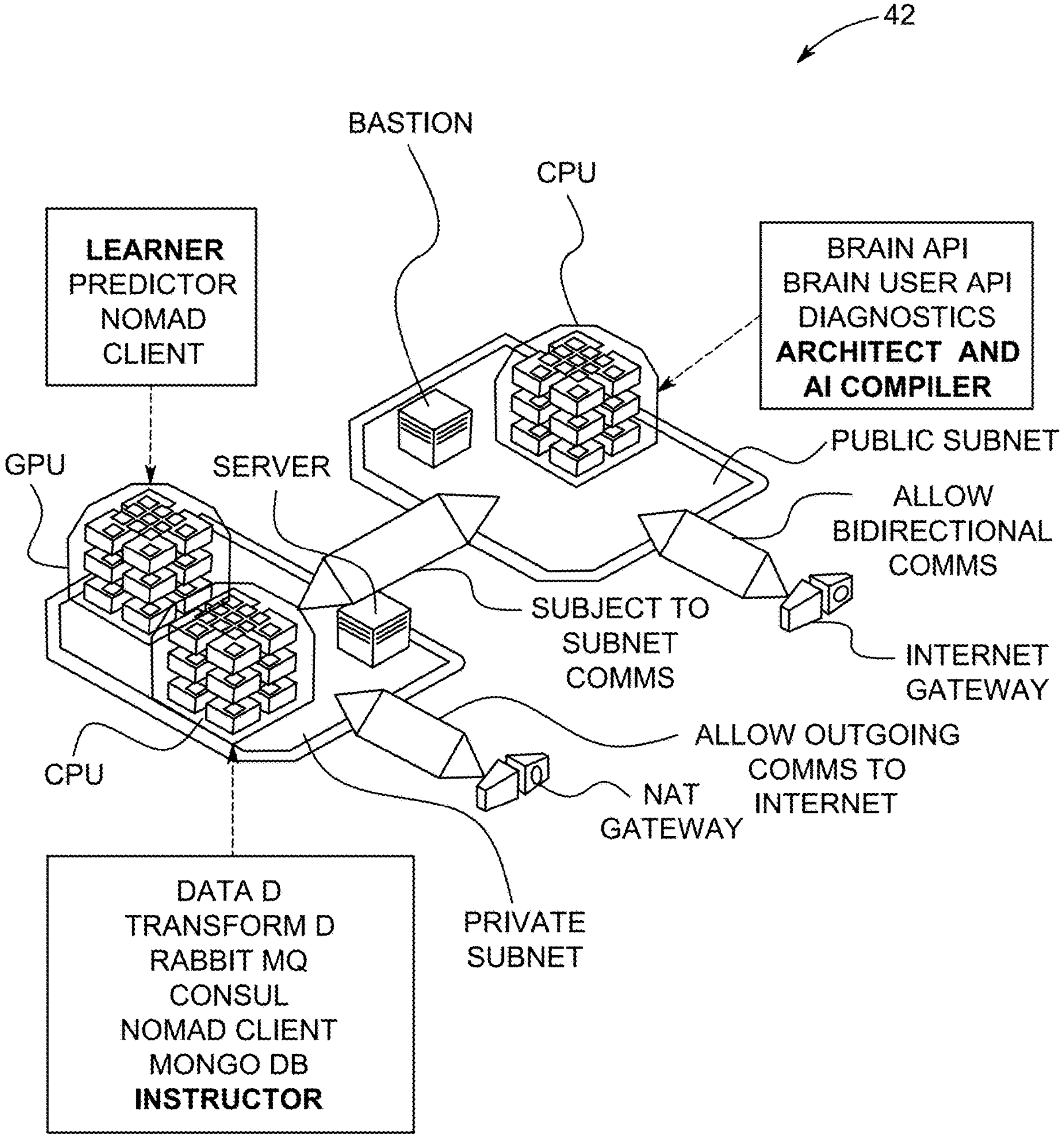
FIG. 29 provides a block diagram illustrating an AI system and its on-premises based computing platforms infrastructure in accordance with an embodiment.

As illustrated in FIG. 29, a user, such as prior and current surgeons, prior and current assistants, third parties, and the like (users), can interface with the AI system 42 through an online interface. AI system 42 can enable a user to make API and web requests through a domain name system. API load balancer can be configured to distribute the API requests among multiple BRAIN service containers running in a Docker network or containerization platform configured to wrap one or more pieces of software in a complete filesystem containing everything for execution including code, runtime, system tools, system libraries, etc. The web load balancer can be configured to distribute the web requests among multiple web service containers running in the Docker network. The Docker network or Docker BRAIN network can include central processing unit ("CPU") nodes and graphics processing unit ("GPU") nodes, the nodes of which Docker network can be auto scaled as needed. The CPU nodes can be utilized for most BRAIN-service containers running on the Docker network, and the GPU nodes can be utilized for the more computationally intensive components such as TensorFlow and the learner module.

FIG. 29 provides a block diagram illustrating AI system 42 and its on-premises computing platforms infrastructure in accordance with an embodiment of the present.

Computing system 800 that can be, wholly or partially, part of one or more of the server or client computing devices in accordance with an embodiment. Computing system 800 can include, but are not limited to, a processing unit 820 having one or more processing cores, a system memory 830, and a system bus 821 that couples various system components including the system memory 830 to the processing unit 820. The system bus 821 may be any of several types of bus structures selected from a memory bus or memory controller, a peripheral bus, and a local bus using any of a variety of bus architectures.

Computing system 800 typically includes a variety of computing machine-readable media. Computing machine-readable media can be any available media that can be accessed by computing system 800 and includes both volatile and nonvolatile media, and removable and non-removable media. By way of example, and not limitation, computing machine-readable media use includes storage of information, such as computer-readable instructions, data structures, other executable software or other data. Computer-storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other tangible medium which can be used to store the desired information and which can be accessed by the computing device 800. Transitory media such as wireless channels are not included in the machine-readable media. Communication media typically embody computer readable instructions, data structures, other executable software, or other transport mechanism and includes any information delivery media. As an example, some client computing systems on the network 820 of FIG. 7 might not have optical or magnetic storage.

The system memory 830 includes computer storage media in the form of volatile and/or nonvolatile memory such as read only memory (ROM) 831 and random-access memory (RAM) 832. A basic input/output system 833 (BIOS) containing the basic routines that help to transfer information between elements within the computing system 800, such as during start-up, is typically stored in ROM 831. RAM 832 typically contains data and/or software that are immediately accessible to and/or presently being operated on by the processing unit 820.

The computing system 800 can also include other removable/non-removable volatile/nonvolatile computer storage media. Other removable/non-removable, volatile/nonvolatile computer storage media that can be used in the example operating environment include, but are not limited to, USB drives and devices, flash memory cards, solid state RAM, solid state ROM, and the like. The solid-state memory 841 is typically connected to the system bus 821 through a non-removable memory interface such as interface 840, and USB drive 851 is typically connected to the system bus 821 by a removable memory interface, such as interface 850.

Figure 30:
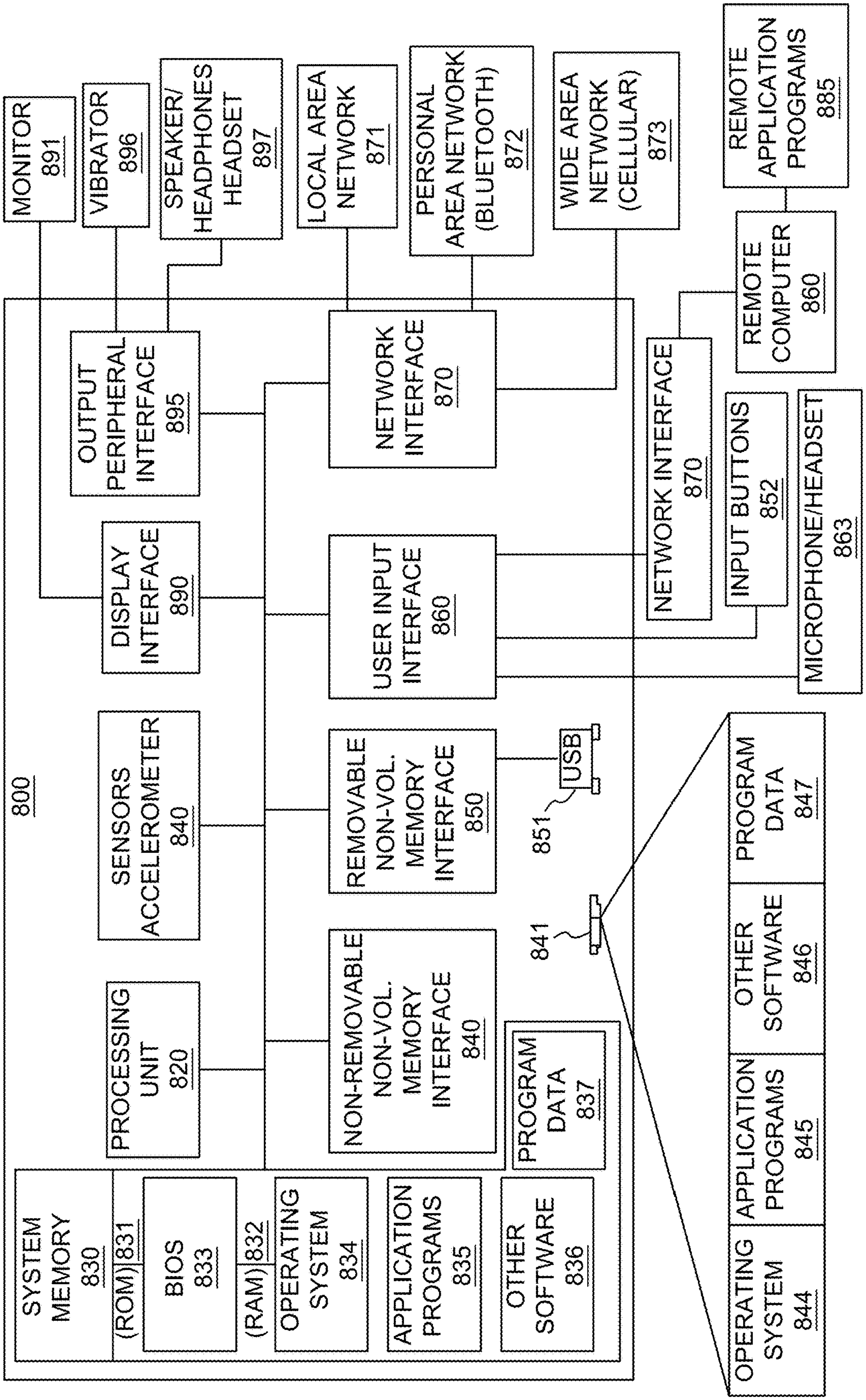
FIG. 30 provides one or more computing systems in accordance with an embodiment.

FIG. 30 provides one or more computing systems in accordance with an embodiment.

Figure 31:
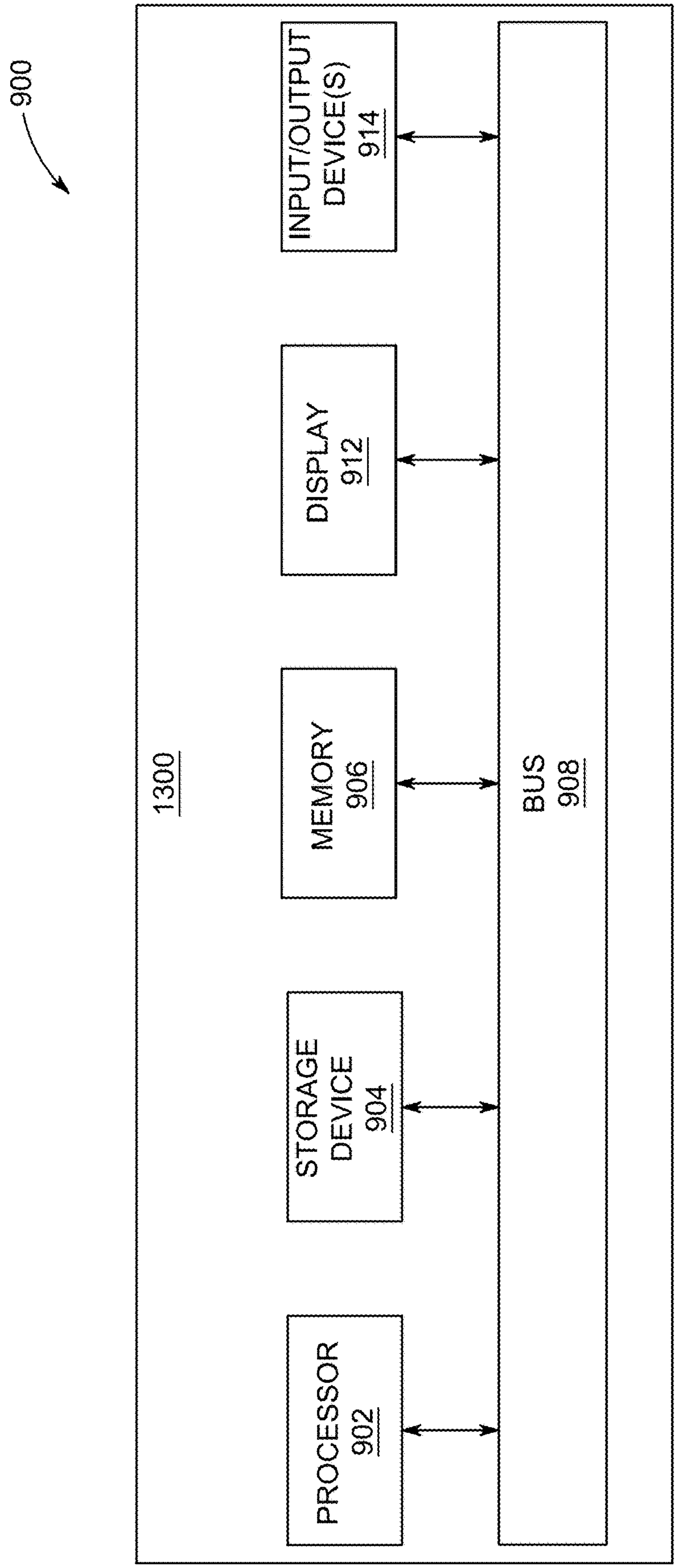
FIG. 31 illustrates one embodiment of block diagram that illustrates components of a computing device of the present invention.

FIG. 31 illustrates one embodiment of block diagram that illustrates components of a computing device 900. The computing device 900 can implement aspects of the present disclosure, and, in particular, aspects of the patient management and 111, including but not limited to a frontend server, a patient data service, the patient care management service, and/or the patient monitoring service. The computing device 900 can communicate with other computing devices.

The computing device 900 can include a hardware processor 902, a data storage device 904, a memory device 906, a bus 908, a display 912, and one or more input/output devices 914. A processor 902 can also be implemented as a combination of computing devices, e.g., a combination of a digital signal processor and a microprocessor, a plurality of microprocessors, one or more microprocessors in conjunction with a digital signal processor, or any other such configuration. The processor 902 can be configured, among other things, to process data, execute programmed instructions 67 of surgical computing device 151 to perform one or more functions, such as process one or more physiological signals to obtain one or measurements, as described herein. The data storage device 904 can include a magnetic disk, optical disk, or flash drive, etc., and is provided and coupled to the bus 908 for storing information and programmed instructions 67 of surgical computing device 151. The memory 906 can include one or more memory devices that store data, including without limitation, random access memory (RAM) and read-only memory (ROM). The computing device 900 may be coupled via the bus 908 to a display 912, such as an LCD display 24 or touch screen, for displaying information to a user, such as a clinician. The computing device 900 may be coupled via the bus 908 to one or more input/output devices 914. The input device 914 can include, but is not limited to, a keyboard, mouse, digital pen, microphone, touch screen, gesture recognition system, voice recognition system, imaging device (which may capture eye, hand, head, or body tracking data and/or placement), gamepad, accelerometer, or gyroscope.

In one embodiment, a control device is coupled to the robotic surgical arms 54. The control device can be configured or programmed to control the robotic surgical arms 54.

In one embodiment AI system 42 has a plurality of machine learning algorithms. The robotic surgical arms 54 are at least partially controlled by the AI system 42 and the control device which processes intraoperative data including images captured by cameras and sensor inputs. The machine learning algorithms analyze the intraoperative data in real-time, compare it with stored images and procedural information in image recognition and procedure databases. The one or more machine algorithms enable at least a partial identification of anatomical structures. In response to detection of the anatomical structures, the AI system 42 at least partially adjusts movement of the robotic surgical arms 54 to avoid the anatomical structures while performing the robotic surgery procedure. This allows for precise targeting at the surgical site while minimizing damage to surrounding tissue and the anatomical structures near the surgical site. AI system 42 provides a surgeon with improved dexterity when the surgeon uses the robotic surgical arms 54 at the surgical site. The improved dexterity results, at least partially by real-time data analysis of the intraoperative data by the one or more machine learning algorithms, precise and adaptive manipulation of the robotic surgical arms 54 at the robotic surgical site, executing a planned surgical step of the robotic surgery procedure using the one or more machine learning algorithms. The AI system comprises a modular architecture: a Training Module for continual model improvement, an Inference Engine for intraoperative predictions, and a Feedback Module for real-time adaptation based on system performance.

Real-time AI image enhancement allows for enhanced identification of anatomical structures, and robotic surgical arms. System 10 provides an online preprocessing framework capable of denoising, deblurring, and color-correcting real-time camera imaging to enhance intraoperative visualization for tumor, blood vessel and nerve identification. System 10 can use augmented reality integrated through AI for overlaying important information such as vitals and hemodynamic state of a patient in real-time to the surgeon.

The improved dexterity of the robotic surgical arms 54 can provide seamless integration of real-time data processing, advanced machine learning, and adaptive instrument control. This allows robotic system to perform highly intricate surgical tasks while responding dynamically to intraoperative changes, significantly enhancing surgical precision, safety, and efficiency. In one embodiment, the use of computer vision and machine learning (particularly deep learning) is used to analyze operative video data and recognize the anatomical structures.

The anatomical structures can include one or more of: tumors, blood vessels and nerves. The anatomical structures can include one or more of: skin, subcutaneous tissue, adipose tissue, fascia, muscle, tendons, ligaments, bones, joints, cartilage, hollow or solid organs, vascular structures (arteries, veins, capillaries, lymphatic vessels and nodes), peripheral nerves, spinal cord and nerve roots, autonomic nerves, peritoneum, pleura, and pericardium. These anatomical structures are avoided during the robotic surgical procedure, allowing a more targeted to the robotic surgical site. Identification of these structures intra-operatively can be facilitated by anatomical landmarks. However, these landmarks can be variable. Once these anatomical structures are identified, AI system 42 calculates optimal instrument movements, adjusting parameters such as trajectory, force, and angle to ensure precise targeting while avoiding damage to surrounding tissues.

In one embodiment, system continuously monitors the interaction between the robotic instruments and the surgical site. If irregularities are detected, such as unexpected tissue resistance, anatomical variations, or anomalies in the planned path, AI system 42 prompts immediate recalibration of the robotic arms 54' movements. For instance, if the robotic arms 54 encounter an area with higher tissue density than anticipated, the system calculates the necessary adjustments, such as reducing applied force or changing the angle of approach. These calculations and adjustments occur in real-time, allowing the robotic arms 54 to maintain accuracy and avoid unintended damage.

Additionally, the system leverages predictive modeling, and historical data can be used to refine movement predictions. Using patterns learned from prior procedures (either surgeon specific or from a database of prior surgeries), the AI system 42 can anticipate challenges such as tissue shifts caused by patient movement or physiological processes such as breathing. By synchronizing robotic movements with these variables, the system ensures smooth and consistent instrument operation. The machine learning algorithms also assign confidence scores to each planned movement based on the analysis of intraoperative data. This can prompt and guide the surgeon to the optimal path. The AI system comprises a modular architecture: a Training Module for continual model improvement, an Inference Engine for intraoperative predictions, and a Feedback Module for real-time adaptation based on system performance.

The robotic arms 54 enhanced dexterity also includes the ability to make ultra-fine movements, such as micro-suturing or precise dissections, by utilizing feedback from sensors, camera and the like. These sensors and cameras produce images, detect pressure, vibration, and other tactile information, which the AI system 42 processes to further refine instrument control. For example, during tumor resection, the system can detect and adjust for subtle differences in tissue texture, ensuring the tumor is removed with minimal impact on surrounding healthy tissue. Each arm's 54 trajectory is dynamically refined by the AI engine using probabilistic models that account for patient-specific anatomical deviations.

At least a portion of the sensor data may contain noisy data, including errors, outliers, and inconsistencies. System 10 provides functionality for identifying, cleaning, and transforming such noisy data to optimize its use in machine learning algorithms. The system includes a preprocessing module, which may be integrated into the system or implemented as a separate component and employs advanced techniques such as rule-based filters, machine learning algorithms, or heuristic methods to detect and address anomalies or inconsistencies. For example, it can identify missing values, duplicate records, or formatting errors and either correct these issues based on predefined rules or remove the problematic records entirely. Additionally, the module can leverage external data sources or context-aware algorithms to validate and enrich the data, enhancing its quality and relevance. The preprocessing functionality is highly adaptable, allowing customization to suit specific dataset requirements or applications. It supports both real-time and batch processing workflows, enabling efficient handling of large-scale data while ensuring data integrity, reliability, and usability for downstream analytics, modeling, or other processes. Further, the system can detect incomplete, incorrect, or inaccurate data and then replace, modify, or delete the affected records. Data cleansing can be performed interactively using data wrangling tools or through batch processing, often implemented via scripts or a data quality firewall, to maintain consistent and reliable datasets.

As a non-limiting example, system 10 provides for data cleaning, also referred to as data scrubbing or data cleansing, that is the process of preparing data for analysis by identifying and correcting errors, inconsistencies, and inaccuracies. This can be achieved in the AI module/engine and/or in a separate preprocessing module.

In one embodiment, system 10 provides for sensor data preprocessing that transforms raw, unstructured, or noisy data into a clean, structured format suitable for analysis. As stated previously, raw sensor data may contain missing values, outliers, inconsistencies, or redundant information, all of which can adversely impact the performance of machine learning algorithms. In one embodiment, system 10 provides systematic data preprocessing.

In one embodiment, system 10 gathers relevant data for sensor data, the sensor data is cleaned and optionally splitting it into training and testing sets. The training set is used to train, while the testing set evaluates its performance As a non-limiting example, system 10 can preprocess sensor data and to eliminate or reduce noise. This can include but is not limited to the following types of sensor data noise: Feature Noise that refers to superfluous or irrelevant features present in the dataset that might cause confusion and impede the process of learning; Systematic Noise: Recurring biases or mistakes in measuring or data collection procedures that cause data to be biased or incorrect; Random Noise: unpredictable fluctuations in data brought on by variables such as measurement errors or ambient circumstances; Background noise: information in the sensor data that is unnecessary or irrelevant and could distract the model from the learning job, and the like.

As a non-limiting example, noise can include measuring errors, anomalies, or discrepancies in the sensor data. Handling noise is important because it might result in AI machine learning algorithm that are unreliable and forecasts that are not correct.

As a non-limiting example, system 10 preprocesses at least of sensor data by a preprocessing module that can be include with or separate from AI module. It can include methods to improve the quality of the sensor data and lessen noise from errors or inconsistencies, such as data cleaning, normalization, and outlier elimination. Sensor data can be preprocessed with the use of Fourier Transform which can be a mathematical technique used to transform signals from the time or spatial domain to the frequency domain. In the context of noise removal, it can help identify and filter out noise by representing the signal as a combination of different frequencies. Relevant frequencies can be retained while noise frequencies can be filtered out.

In one embodiment, constructive learning involves training a machine learning model to distinguish between clean and noisy data instances. This can require labeled data where the noise level is known. The model learns to classify instances as either clean or noisy, allowing for the removal of noisy data points from the dataset.

Autoencoders can be utilized, with autoencoders being neural network architectures that can include an encoder and a decoder. The encoder compresses the input data into a lower-dimensional representation, while the decoder reconstructs the original data from this representation. Autoencoders can be trained to reconstruct clean signals while effectively filtering out noise during the reconstruction process.

As a non-limiting example, principal component analysis (PCA) can be used by system 10 to reduce and/or eliminate noisy data. PCA is a dimensionality reduction technique that identifies the principal components of a dataset, which are orthogonal vectors that capture the maximum variance in the data. By projecting the data onto a reduced set of principal components, PCA can help reduce noise by focusing on the most informative dimensions of the data while discarding noise-related dimensions.

As a non-limiting example, noisy data cross-validation and ensemble models can be used to eliminate or reduce noisy data. Cross-validation is a resampling technique used to assess how well a predictive model generalizes to an independent dataset. It involves partitioning the dataset into complementary subsets, performing training on one subset (training set) and validation on the other (validation set). This process is repeated multiple times with different partitions of the data. Common cross-validation methods include k-fold cross-validation and leave-one-out cross-validation. By training on different subsets of data, cross-validation helps in reducing the impact of noise in the data. It also aids in avoiding overfitting by providing a more accurate estimate of the model's performance. Ensemble learning involves combining multiple individual models to improve predictive performance compared to any single model alone. Ensemble models work by aggregating the predictions of multiple base models, such as decision trees, neural networks, or other machine learning algorithms. Popular ensemble techniques include bagging (bootstrap aggregating), boosting, and stacking. By combining models trained on different subsets of the data or using different algorithms, ensemble models can mitigate the impact of noise in the data. Ensemble methods are particularly effective when individual models may be sensitive to noise or may overfit the data. They help in improving robustness and generalization performance by reducing the variance of the predictions.

As a non-limiting example, system 10 provides for the removable and/or adding the following: missing values that are missing entries that arise due to incomplete data collection or errors during data entry. Inconsistencies; differences in data formats, units, or encoding that can create confusion and errors during processing; outliers which can be extreme or anomalous values that skew results, leading to incorrect insights or predictions; redundancy that can include non-relevant duplicate records which inflate dataset size and misrepresent actual trends; irrelevance with features that are unrelated to target variable can introduce noise and hinder model performance.

Patient health information is collected in real-time data and can be used to improve disease monitoring and management. Additionally, it is used for early disease detection and prevention. The Health Information Technology for Economic and Clinical Health Act (HITECH Act), enacted as part of the American Recovery and Reinvestment Act of 2009, (ARRA) contains provisions that strengthen the privacy and security protections for certain health information established under HIPAA. From blockchain-based solutions to artificial intelligence-powered threat detection systems, system 10 can include resources to mitigate the risks associated with cyber threats and protect the integrity of medical devices including but not limited to surgical robot system 10.

As a non-limiting example, system 10 provides logic resource.

In one embodiment, system 10 cyber security resources are included that minimize hacking of patient data in compliance with HIPAA.

In one embodiment, cryptography algorithms function by: encrypting data into ciphertext, making it unreadable to unauthorized users; ensuring secure communication by encrypting data during transit; and the like. In one embodiment, machine learning algorithms and AI help identify and prevent cyberthreats by: using supervised learning models with labeled data to train a system and recognize patterns associated with malicious activity; employing anomaly detection to flag deviations from normal network behavior; applying reinforcement learning to adaptively respond to evolving threats; and continuously updating threat models based on real-time data to improve predictive accuracy and responsiveness.

In various embodiment, system 10 the robotic surgical arms 54 are at least partially controlled by the AI system 42 and the control device (system) 22 to process intraoperative data including images captured by cameras and sensor inputs. The machine learning algorithms analyze the intraoperative data in real-time, compare it with stored images and procedural information in image recognition and procedure databases. The one or more machine algorithms enable at least partial identification of anatomical structures. In response to detection of the anatomical structures the AI system 42 at least partially adjusts movement of the robotic surgical arms 54 to avoid critical anatomical structures while performing the robotic surgery procedure to ensure precise targeting at the surgical site while minimizing damage to surrounding tissue at a surgical site. The AI system 42 provides a surgeon with improved dexterity when the surgeon uses the robotic surgical arms 54 at the surgical site. The improved dexterity results from at least partially analyzing the intraoperative data in real-time by the one or more machine learning algorithms and enables precise and adaptive manipulation of the robotic surgical arms 54 *s* at the surgical site. The AI system comprises a modular architecture: a Training Module for continual model improvement, an Inference Engine for intraoperative predictions, and a Feedback Module for real-time adaptation based on system performance.

A force feedback system can be coupled to the sensors and surgical apparatus to detect force exerted on tissue and adjust resistance on a hand-actuated selector in response to tissue density, elasticity, and at least one physiological process, wherein the physiological process includes one or more of tissue perfusion, nerve activity, and temperature.

One or more sensors can be provided, including a combination of ultrasound, x-ray, and optical sensors, and optionally one or more of electromagnetic (EM) tracking sensors, force sensors, pressure sensors, tactile sensors, inertial measurement units (IMUs), temperature sensors, bioimpedance sensors, optical coherence tomography (OCT) sensors, fluorescence imaging sensors, near-infrared spectroscopy (NIRS) sensors, and micro-endoscopes. The sensors are positioned on the robotic arms 54, integrated into the surgical instruments, integrated into the surgical operating table, or placed on or near the patient; and haptic feedback devices that provide the surgeon with tactile sensations corresponding to the forces encountered by the robotic surgical arms 54.

One or more interactive 4D visualization tools integrate time as a fourth dimension, enabling the surgeon to visualize physiological processes in real-time.

System can enable a user to manipulate time-synchronized 3D models using hand gestures detected via a touch-free interface. A feedback loop can provide real-time analysis of the complexity of an anatomical region.

In one embodiment, AI system 42 includes one or more of: a reinforcement learning module that refines the machine learning algorithms based on surgical outcomes and intraoperative data from previous procedures; generates suggested surgical plans or modifications to existing plans based on the analysis of patient-specific data and the information stored in the image recognition and procedure databases; autonomously adjusts the robotic surgical arms 54 to compensate for patient movement or changes in anatomy during the procedure; provides real-time feedback to the surgeon regarding potential risks or complications based on the intraoperative data; predicts the likelihood of success for different surgical approaches based on the analysis of patient data and historical outcomes; automatically documents the surgical procedure, including images, sensor data, and annotations, for later review and analysis; aligns a model to a patient's anatomy, the model being generated from pre-operative CT, MRI, X-ray, ultrasound, or other imaging studies, registered to the patient's anatomy using fiducial markers or image registration algorithms, and dynamically updated to reflect tissue deformation and intraoperative sensor data; and provides an overlay highlighting a region of interest, wherein the region of interest is selected from one or more of: skin, subcutaneous tissue, adipose tissue, fascia, muscle, tendons, ligaments, bones, joints, cartilage, hollow or solid organs, vascular structures (arteries, veins, capillaries, lymphatic vessels and nodes), peripheral nerves, spinal cord and nerve roots, autonomic nerves, peritoneum, pleura, pericardium, and benign or malignant neoplasms. The AI system comprises a modular architecture: a Training Module for continual model improvement, an Inference Engine for intraoperative predictions, and a Feedback Module for real-time adaptation based on system performance.

In one embodiment, AI system 42 provides one or more of: a hybrid pose estimation model that combines image-based pose estimation (including marker-based tracking, marker-less tracking, and deep learning-based methods), sensor-based pose estimation (including encoders, IMUs, and electromagnetic tracking), and model-based pose estimation, using Kalman filters or other state estimation techniques to combine data from multiple sources to produce an accurate and robust estimate of object pose, and optionally predict future pose; generates enhanced or synthetic images of anatomical structures based on limited or incomplete imaging data; improves the resolution or quality of intraoperative images using deep learning techniques; generates three-dimensional reconstructions of anatomical structures from two-dimensional images or sparse data; predicts the future deformation or movement of anatomical structures based on real-time image analysis and biomechanical models; segments anatomical structures in images, automatically identifying and delineating organs, tissues, or other regions of interest; registers intraoperative images to pre-operative image data or anatomical models; provides real-time guidance to the surgeon by overlaying virtual models or annotations onto the live surgical field and suggests optimal surgical paths or instrument trajectories based on pre-operative planning and intraoperative data; automatically adjusts the robotic surgical arms 54 to maintain alignment with target anatomical structures or avoid critical regions and provides warnings or alerts to the surgeon regarding potential risks or complications based on real-time image analysis; adapts surgical plans in real-time based on changes in the patient's anatomy or unforeseen events during the procedure and quantifies tissue properties or characteristics, such as stiffness or perfusion, based on image analysis; generates enhanced intraoperative images and provides real-time guidance to the surgeon by highlighting critical structures and suggesting optimal surgical paths; segments anatomical structures in real-time, registers them to pre-operative models, and provides automated adjustments to the robotic surgical arms 54 to ensure precise targeting; and utilizes reinforcement learning to optimize surgical strategies based on past outcomes.

The surgeon can interact with the AI system 42 through voice commands or gesture recognition. The display 912 on the surgeon console can overlay real-time intraoperative images with virtual models of the anatomy and the surgical plan. In one embodiment, system 10 allows for remote collaboration between surgeons, enabling experts to provide guidance or assistance during a procedure. The system can be specifically adapted for minimally invasive surgical procedures. The system 10 can be specifically adapted for a particular surgical specialty, such as cardiac surgery, neurosurgery, or orthopedic surgery. The system is used cam deliver targeted therapy, such as drugs or radiation, to specific anatomical locations.

A network interface can securely transmit surgical data to remote servers for storage, analysis, or collaboration. The system 10 integrates with electronic health records (EHR) systems to access patient data and update records. Feedback loop can be provided, wherein the machine learning algorithms monitor the surgeon's cognitive state, including stress and fatigue levels (measured through heart rate variability analysis, eye-tracking metrics, and optionally other physiological measures and response times), and dynamically adjusts the robotic control system 22 and surgical displays to optimize surgeon performance and patient safety. The feedback loop can be provided, wherein the machine learning algorithms use data from the sensors to provide real-time tissue regeneration simulation. In one embodiment, feedback loop executed the machine learning algorithms to provide a visualization of the outcome of one or more surgical decisions on tissue regeneration.

In one embodiment, the robot adjusts one or more of motion scaling, tool dynamics, and visualizations based on data from prior surgeries.

1Integrated AI-Powered Adaptive Robotic Surgery System

In one embodiment, robotic surgical system, includes surgeon console 12 with at least one input device and an interactive display 24 configured to receive multi-modal surgeon commands and present real-time visual and contextual feedback. The patient console 16 has at least one robotic arm 54 configured to manipulate a surgical instrument 18. The robotic arm 54 is capable of fine-grained motion control in multiple degrees of freedom.

A plurality of sensors acquires system and user data, including at least one of: intraoperative image data; instrument 18 force and torque data; motion tracking data; physiological signals from the patient or surgeon; environmental data (including but not limited to temperature, humidity, air flow, air quality, lighting levels, noise levels, proximity of personnel or objects, vibration or movement, sterile field breaches, device status, thermal data, diagnostics of the robotic system, or sterility data), surgeon eye tracking, gesture recognition, voice input, or biometric indicators.

A control system 22 is coupled to the surgeon console, patient console, and the plurality of sensors. The control system 22 manages execution of robotic control instructions and synchronize system components, communicatively coupled to the surgeon console, patient console, and the plurality of sensors, the control system 22 comprising one or more processors and memory storing programmed instructions, the control system 22 configured to: receive control inputs from the surgeon console 12 and translate them into robotic motion instructions; receive sensor data from the plurality of sensors and monitor intraoperative conditions in real-time; manage execution of robotic control instructions by generating and transmitting synchronized actuation commands to the patient console; provide feedback to the surgeon console based on real-time sensor input and system status; and synchronize and coordinate system components, including visual output, haptic feedback, robotic actuation, and AI-based decision support modules, to ensure safe and efficient execution of the surgical procedure.

Artificial intelligence (AI) system 42 provided that includes at least one processor and memory storing instructions that, when executed, cause the system to: receive and process sensor data in real-time; construct and dynamically update a user model, the user model comprising at least one of: surgeon skill level; physiological state, cognitive load; task performance metrics; prior interaction patterns; and analyze the user model and intraoperative data using one or more machine learning algorithms.

The one or more machine learning algorithms provide one or more of: identify anatomical structures, procedural risks, and user behavior patterns; predict potential deviations, complications, or errors; modify robotic and interface parameters accordingly; adapt one or more of: robotic arm 54 motion trajectory, velocity, force application; user interface responsiveness, automation thresholds, visual overlays, audio/haptic feedback profiles; deliver predictive alerts or autonomous control interventions; log procedural data, AI-generated decisions, and system responses for post-procedure review and training.

As a non-limiting example, AI system 42 integrates real-time intraoperative data with: pre-operative planning data including patient-specific imaging and surgical plans; procedural databases of historical surgical cases; surgeon-specific interaction logs or prior procedure outcomes; to enhance predictive accuracy, adapt tool behavior, and support dynamic surgical decision-making.

In one embodiment, the robotic control system 22 dynamically recalibrates reference frames or spatial models based on one or more of: changes in patient positioning, tool (surgical instrument 18) exchange events; movement of imaging devices; as well as tissue deformation detected by imaging or force feedback sensors.

System can include a contextual intent inference module configured to: monitor surgeon gestures, voice commands, gaze patterns, or biometric indicators; infer likely next actions or intended tool use; and proactively adjust system interface elements or prepare instruments for deployment.

As a non-limiting example, system includes an augmented reality (AR) subsystem integrated with the surgeon console, configured to: superimpose anatomical structures, procedural suggestions, tool projections, or AI alerts onto live imaging feeds; and adjust display layers based on surgeon attention or user model.

In one embodiment, system includes an autonomous override mode, triggered upon detection of high-risk procedural deviation or surgeon fatigue, The mode is configured to: temporarily modulate or inhibit manual input; execute safety protocols; provide real-time justification via the interface; and allow surgeon override or consent continuation.

AI system 42 can be one of: convolutional neural networks (CNNs) for image interpretation; be a transformer model or temporal convolutional network for procedural state modeling; reinforces learning agents for adaptive tool control; generates adversarial networks (GANs) for content generation; and uses federated learning models for decentralized model training across surgical systems. As a non-limiting example, control system 22 is a latency-optimized co-processor configured to execute edge AI inference for sub-50 ms response time for safety events or anatomical detection. In one embodiment, robotic arm 54 includes embedded haptic sensors, and the surgeon console includes tactile actuators that enables real-time bidirectional force feedback.

As a non-limiting example, user interface includes: an adaptive audio feedback module configured to adjust pitch, volume, spatialization, and content according to environmental noise and surgeon stress levels; a modular framework for real-time interface reconfiguration based on user role or task requirements; and supports hot-swappable visual or control widgets without interrupting ongoing procedures. System can include a situational awareness engine, configured to: interpret external environmental context (e.g., lighting, emergency codes, equipment proximity); correlate with the user model; adjust safety thresholds; adjusts alert presentation, and automation engagement. In one embodiment, system includes a remote collaboration module that enables: multiple surgeons or observers to engage with the procedure in real-time or asynchronously; role-based access control and individualized interface rendering; and synchronized interaction with shared AI data and imaging overlays.

As a non-limiting example, the user model includes biometric authentication features, enabling immediate surgeon identification and retrieval of personalized control profiles, learning data, and UI configurations. System can include a simulation and training mode that uses: real intraoperative case data; AI-generated performance metrics; and surgeon-specific predictive feedback to support credentialing, peer review, and ongoing training.

In one embodiment, AI system 42 is configured to: analyze post-operative outcomes and link them to intraoperative decisions; iteratively refine its models via outcome tracking; shares insights across installations via federated learning while preserving HIPAA-compliant data boundaries.

In one embodiment, a method for intelligent and adaptive control of robotic surgery: receives intraoperative and operator state data from a robotic surgical system; constructs a dynamic user model based on physiological signals, skill level, and behavioral patterns.

Machine learning analyzes a current procedural state; predicts deviations, risks, or complications; adapts control parameters and user interface presentation; generates predictive alerts and, if necessary, autonomous interventions; and records all system decisions, control adjustments, and user interactions for postoperative review.

In one embodiment, robotic surgical system 10 has: at least one robotic arm 54 configured to manipulate a surgical instrument 18; a plurality of sensors integrated with or proximate to the surgical instrument 18, configured to measure force, torque, and optionally other physical parameters at a tool-tissue interface; an imaging system configured to capture real-time images of a surgical site. A surgeon console 12 can include at least one feedback device configured to render tactile sensations to an operator. A biometric authentication module can be included at surgeon console 12 to ensure secure system operation and surgeon-specific feedback personalization.

An artificial intelligence (AI) processing system (hereafter AI system 42) is coupled to the sensors, imaging system, and surgeon console 12. A surgeon training module can be provided in which simulated surgical environments and virtual tissue properties are rendered to the haptic feedback device for rehearsal or skill acquisition purposes. Haptic feedback can be enhanced with synchronized audio or visual cues to provide multi-modal sensory integration for improved situational awareness.

AI processing location for can include one or more processors configured to execute instructions stored in memory to: receive and synchronize force sensor data and image data in real-time; analyzes the synchronized data using one or more trained machine learning models to determine real-time tissue properties at or near the tool-tissue interface, the tissue properties comprising at least one of stiffness, elasticity, density, or tissue type; generates adaptive haptic feedback signals based on the determined tissue properties and optionally predicts tissue behavior; and a data transmission module configured to transmit the adaptive haptic feedback signals to the haptic feedback device at the surgeon console 12. Generating the adaptive haptic feedback signals can includes modifying raw force sensor data by performing at least one of: scaling, filtering, adding virtual texture or compliance data, or simulating anticipated force variations. AI processing system 42 can generate haptic boundary alerts when the surgical instrument 18 approaches a predetermined critical anatomical structure or tissue boundary. As a non-limiting example, AI control system 22 adjusts haptic feedback parameters based on at least one of a: surgical phase; type of instrument used; real-time physiological data; proximity to critical structures; and personalized surgeon feedback preferences.

AI control system 22 can incorporate pre-operative imaging data into the tissue property estimation and adaptive feedback generation pipeline. AI processing system can detect abnormal tissue properties in real-time, such as signs of pathology, and modify haptic output accordingly to guiding the surgeon toward or away from suspicious areas.

AI processing system 42 can use reinforcement learning to optimize haptic response precision and surgeon satisfaction over time, based on feedback or surgical outcomes. An augmented reality (AR) interface can be integrated with the surgeon console 12 and configured to display overlays correlating with one or more of: haptic intensity; predicted tissue characteristics; and proximity warnings, and surgical navigation data. AI system 42 can integrate user behavior metrics including force application patterns and response time to tailor feedback strategies and anticipate errors. AI processing system 42 can include anomaly detection models to identify deviations from normative surgical flow and initiate safety overrides. In one embodiment, AI processing system 42 can create a personalized haptic profile for each surgeon by aggregating prior procedure data and dynamically adjusting feedback thresholds.

A feedback calibration module can be included to automatically tune haptic feedback intensity based on user-specific thresholds, sensor drift, or instrument variation. In one embodiment haptic feedback device provides at least one of: vibrotactile feedback; kinesthetic force feedback and electro-tactile stimulation. As a non-limiting example, adaptive haptic feedback is selectively disabled or modified in response to sudden anomalies such as patient movement, equipment fault, or abrupt changes in sensor readings to ensure surgeon safety.

Data transmission module can include latency compensation algorithms to ensure synchronized and temporally accurate haptic rendering in remote or tele-surgical operations. A cloud-based analytics module can be provided configured to: store and analyze intraoperative haptic and sensor data across multiple procedures; improve model accuracy through federated learning; and generate post-operative reports for surgical performance feedback.

Imaging system can include real-time spectral or hyper-spectral imaging to aid tissue classification and enhance machine learning analysis.

The plurality of sensors can include: pressure-sensitive optical fibers or piezoelectric materials embedded within the surgical instrument 18 for fine-grained force resolution.

In one embodiment, robotic surgical system network includes a plurality of robotic surgical systems, each system having robotic arms 54. A plurality of sensors and a surgeon console 12 can be provided, as well as a control system 22 with an integrated artificial intelligence (AI) module. AI module can be configured to generate post-operative summaries comprising annotated procedure timelines; alerts; and performance metrics. AI module can use an explainable AI (XAI) component configured to generate human-interpretable rationales for intraoperative decisions or recommendations. Explainable AI component can employ attention heatmaps and textual justifications aligned with medical ontologies. The summaries can be produced using AI-based natural language generation and video frame annotation. Each arm's 54 trajectory is dynamically refined by the AI engine using probabilistic models that account for patient-specific anatomical deviations.

A human-AI collaboration module can be provided and configured to dynamically allocate control between the human operator and AI system 42 during surgical procedures based on real-time performance metrics, surgeon preference, or contextual complexity.

A network interface can be associated with each robotic surgical system and be configured for secure data communication. A central or distributed data repository can be coupled to the network interfaces. Data repository can be included and configured to securely store surgical data aggregated from the robotic surgical systems. A decentralized ledger system can be integrated with data repository to provide immutable logging of surgical events and AI decisions. Decentralized ledger can be based on a permissioned blockchain, and access is controlled via role-based access permissions. Surgical data can include at least one of procedural data; sensor readings; imaging data; AI decision logs; surgical outcomes and user interaction data.

A training module can be coupled to the data repository. Training module utilized aggregated surgical data to train or update AI models for the robotic surgical systems using unsupervised learning, transfer learning, or federated learning techniques. A cybersecurity module implements security measures for data transmission and system access. Cybersecurity measures can include at least one of: encryption; multi-factor authentication; and real-time threat detection.

System can include a collaboration interface enabling two or more users, potentially at different locations, to interact with intraoperative data; AI recommendations; and system controls in real-time. Collaboration interface can be voice recognition with multilingual capability for verbal control and communication.

In one embodiment, robotic surgical system network integrates with external systems including electronic health records (EHR) to access or update patient records.

As a non-limiting example, training module employs federated learning to update global AI models while preserving data privacy by maintaining raw patient data locally. Aggregated data and AI model updates can support benchmarking and performance analytics across the robotic surgery network. Access to surgical data can be subject to audit and permissions for purposes including postoperative review, quality assurance, or surgical training.

An edge computing module can be provided to locally preprocess intraoperative data prior to transmission to the central repository. Preprocessing can be: filtering, compression; and metadata tagging. A predictive analytics engine can be used to identify potential surgical complications or anomalies in real-time by comparing intraoperative data against historical patterns stored in the data repository. Predictive analytics engine can use recurrent neural networks (RNNs) or temporal convolutional networks for temporal pattern recognition.

A simulation module can be used to generate synthetic surgical environments using anonymized surgical data for testing; validation; and training purposes. Synthetic environments can be produced using extended reality (XR) technologies for immersive interaction.

In one embodiment, each robotic surgical system further comprises a redundancy module configured to maintain surgical operation continuity in the event of a subsystem failure by rerouting tasks to backup hardware or cloud-based virtual machines.

System can include a data quality validation engine configured to identify anomalous, incomplete, or corrupted surgical data using statistical modeling and anomaly detection algorithms prior to inclusion in the central repository or training datasets.

As a non-limiting example, the network interface supports real-time telesurgery control by authenticated surgeons over high-bandwidth, low-latency communication links with redundant failover paths.

Control handoff decisions can be governed by a reinforcement learning model trained on surgeon-AI interaction logs. Virtual machine failover can include real-time containerized instances replicating the control system's 22 execution state. Anomaly detection can use unsupervised clustering and reconstruction error metrics from autoencoders.

In one embodiment, robotic surgical system includes: a mobile robotic base configured for autonomous movement; a plurality of robotic surgical arms 54 mounted on the mobile robotic base, each arm 54 configured to manipulate a surgical instrument; a sensor array with one or more sensor types selected from the group consisting of imaging devices, depth sensors, proximity sensors, 3D laser scanners, stereoscopic cameras, infrared cameras, ultrasonic sensors, electromagnetic tracking sensors, radar-based sensors, and physiological sensors, the sensor array configured to capture spatial and contextual data of a patient and an operating environment; a control system 22 coupled to sensor array, mobile base, and robotic arms 54. Control system 22 can include a federated learning module that updates AI models using anonymized external procedural data without transmitting protected health information. The sensor array can include bio-signal acquisition modules to capture ECG, EEG, EMG signals, and the like, for correlating physiological changes with surgical events. Each arm's 54 trajectory is dynamically refined by the AI engine using probabilistic models that account for patient-specific anatomical deviations.

An artificial intelligence (AI) system can include one or more processors configured to: process spatial and contextual data, optionally integrating pre-operative imaging data, to generate and update a dynamic 3D model of the patient and environment; analyze the 3D model using machine learning to determine optimal positioning of the base and arms 54 relative to the patient, including identifying surgical access points; generate and adjust a navigation path for the mobile base to approach a target location while avoiding obstacles; issue control signals to actuate positioning mechanisms for the base and configure the arms 54 according to the optimal plan; and validate positioning before surgical initiation and trigger recalibration if deviations are detected. Mobile base can be configured for deployment on a floor, ceiling, wall, gantry, or track system, and can include mechanical stabilization or emergency braking systems to prevent drift during positioning. The 3D model can be continuously refined during surgery using intraoperative imaging such as fluoroscopy, CT, MRI, or ultrasound.

AI system 42 can compare real-time sensor data with a pre-operative surgical plan and dynamically adjusts arm 54 positioning to maintain alignment or compensate for anatomical shifts or table movement. Robotic ports can engage with the robotic arms 54, the ports including embedded sensors and encoders for detecting alignment and contact forces. AI system 42 can refine end-effector positioning using these inputs. AI system 42 can provide reinforcement learning models trained in digital twin environments of robotic components and patient anatomy to enhance positioning accuracy.

In one embodiment, AI system 42 predicts optimal incision locations based on patient-specific 3D models, anatomical landmarks, and diagnostic data, and assigns confidence scores to surgical access configurations. Robotic arms 54 can include actuators with haptic feedback sensors, and the AI module limits motion or repositions arms 54 to prevent excessive force or tissue damage. AI system 42 can incorporate a predictive maintenance submodule that tracks robotic arm 54 usage and issues alerts for preventive servicing based on operational metrics. AI system 42 can use temporal modeling to anticipate anatomical deformation caused by respiration, heartbeat, or surgical manipulation and adjusts robotic movement accordingly.

An intraoperative alert module can be included that notifies the surgical team if deviations from the validated plan exceed predefined safety margins. A user interface can display the 3D model, and allow operator confirmation, override, or modification of AI-generated positioning or access points. User interface can have augmented reality (AR) functionality to overlay predicted incision sites and access paths onto the patient's body via AR glasses, head-mounted displays 24 and the like.

A remote collaboration module can be configured to allow remote surgeons to view, annotate, and adjust robotic positioning in real-time via a secure, low-latency communication interface. Remote collaboration module can include virtual pointer and annotation tools displayed in the local interface and synchronized with AR overlays.

In one embodiment of the present invention, robotic surgical system includes a robotic manipulator configured to perform surgical procedures under direct surgeon control. A surgical camera system captures real-time intraoperative video. An external imaging interface receives multimodal imaging data, including preoperative and intraoperative data from at least one of magnetic resonance imaging (MRI), computed tomography (CT), ultrasound, and fluoroscopy. An artificial intelligence (AI) module has a trained neural network and a deep learning model trained on multi-institutional annotated surgical datasets. The AI module is configured to: fuse acquired video and imaging data into temporally and spatially coherent anatomical visualizations; generate continuously updating overlays aligned with the surgical field, comprising segmented anatomical features, projected tissue boundaries, proximity indicators for instruments, and predictive deformation trends; provide dynamic predictive trend visualization indicating zones of future anatomical complexity or risk; register and align preoperative imaging data with intraoperative imaging data in real time; adapt overlay presentation in response to tissue deformation without actuating the robotic manipulate or; and passively augment visual feedback without initiating any autonomous actuation of surgical instruments. A display interface at a surgeon console renders the AI-generated overlays and guidance annotations. A user interaction module allows surgeon interaction with overlays via at least one of manual, tactile, voice, or gesture inputs. Surgeon interaction In one embodiment, a surgeon-specific adaptation engine includes: customizable surgeon profiles configured to store individualized preferences for overlay characteristics, alert sensitivity thresholds, feedback latency, and interaction modalities; a real-time analytics module to monitor and record surgeon performance metrics during procedures, including overlay usage frequency, adjustment latency, disengagement behavior, and override rates. A machine learning-based personalization module is trained on prior surgeon sessions. Stored performance and interaction data are used to iteratively refine overlay presentation and generate a dynamic configuration profile that are automatically loaded at the initiation of subsequent procedures for the same surgeon.

In one embodiment, the visualization module includes real-time 3D reconstruction capabilities for depth-aware overlays. The AI module can include a temporal coherence engine to maintain overlay accuracy during tissue deformation. The AI module can include a fusion arbitration engine to dynamically prioritize imaging modalities based on procedural context. A fusion integrity scoring system continuously monitors registration errors between preoperative and intraoperative imaging, and triggers recalibration prompts. Degradation in imaging quality automatically triggers a fallback to a previously validated anatomical model for visual overlay generation. Remote collaborators can be enabled to transmit non-control visual annotations back to the surgeon console during surgery.

In one embodiment, surgeon interactions with overlays are captured and used to continuously refine overlay presentation using machine learning-based adaptation. The predictive trend visualization module can project deformation vectors or swelling indicators within dynamic anatomical overlays. The surgeon console can include a haptic interface. Haptic feedback can be generated based on proximity to predicted anatomical risk zones identified by the AI module. The AI module can be configured to dynamically modulate visual overlay presentation to reduce surgeon cognitive load As a non-limiting example, the modulation can provide: automatic adjustment of overlay density and update frequency during critical surgical phases identified in real time by a context recognition module that analyzes procedural progress and intraoperative events; rendering of color-coded, non-intrusive peripheral alerts on the surgeon console, and indication of proximity to critical anatomical structures without occluding the operative field; display of dynamic warning overlays rendered peripherally and subtly around the main surgical view to highlight anatomical risk zones while maintaining unobstructed visibility of the operative area.

The system can provide integration of an uncertainty quantification module that computes and visually encodes confidence levels associated with segmented anatomical structures. The uncertainty can be represented using transparency gradients, color-coded borders, or shimmer effects to distinguish high-certainty regions from ambiguous or low-certainty data. The AI module can include an anomaly detection engine configured to compare live surgical data with a database of historical procedural data to highlight unexpected tissue characteristics in the overlay. Trends for tissue migration or swelling can be predicted using a trained temporal deformation model based on multimodal intraoperative datasets. Surgeon feedback regarding overlay utility can be captured intraoperatively and used to refine machine learning-based overlay optimization algorithms.

In one embodiment, feedback is received from at least one remote collaborator. The feedback can be overlay modifications or annotations. The modifications can be displayed on the surgeon console without altering robotic actuation.

The predictive deformation trends can be based on time-series analysis of intraoperative imaging and instrument 18 interaction history using a recurrent neural network. The overlay adaptation model can be retrained based on intraoperative surgeon disengagement events and post-procedural feedback.

In one embodiment, intraoperative surgeon interaction with visual overlays is enabled via a multimodal interface that include one or more of: voice commands configured to adjust overlay parameters including opacity, density, alert thresholds, or annotation prominence, where voice commands are processed using a context-aware natural language processing (NLP) engine trained to reduce false positives and ensure precise control; hand gestures detected via intraoperative optical sensors or depth cameras, with the gestures being mapped to predefined overlay control actions using a gesture recognition module trained on surgical context data; gaze tracking performed using infrared eye-tracking cameras integrated into the surgical display system, where overlay annotations are adaptively prioritized within regions of high surgeon attention; a predictive saccade modeling component to anticipate future surgeon fixation points based on historical gaze patterns using a trained machine learning model, and to pre-load corresponding overlay annotations prior to gaze fixation; and a dynamic input arbitration module that prioritizes among voice, gesture, and gaze inputs in real time based on situational context, such that voice commands override gesture inputs in high-movement environments, and gaze tracking is weighted more heavily in tasks requiring visual precision.

In one embodiment, the AI module receives and integrates patient-specific data from external systems including electronic medical records (EMR), picture archiving and communication systems (PACS), to contextualize overlay generation.

In one embodiment, the surgical robotic system has one or more robotic components to perform surgical procedures. A sensor array is coupled to the one or more robotic components. The sensor array detects operational anomalies including microvibration signatures, positional deviations, thermal fluctuations, acoustic emissions, and environmental conditions.

An artificial intelligence (AI) engine is coupled to the sensor array. The AI engine is configured to: receive operational signature data; analyze the data using a predictive failure model trained to identify mechanical degradation, material fatigue, or impending failure; generate a predictive maintenance alert prior to substantial impact on surgical performance.

In one embodiment, a dynamic calibration module automatically adjusts operational parameters of the one or more robotic components during the surgical procedure based on the predictive maintenance alert without interrupting surgical workflow.

A self-healing maintenance engine autonomously initiates preprogrammed corrective mechanical adjustments or activates redundant system components prior to surgeon notification. In one embodiment, the self-healing maintenance engine includes: a corrective action library mapping specific degradation patterns to corresponding adjustments; redundancy activation protocols including switching operational control to backup actuators, redundant sensors, or alternative motion pathways; a closed-loop feedback system to verify efficacy of corrective actions; and prioritization logic based on urgency scores generated by the AI engine's risk assessment module.

The AI engine can utilize a hybrid deep learning architecture with at least one of a recurrent neural network (RNN), convolutional neural network (CNN), or graph neural network (GNN) trained on historical, simulated, and real-time intraoperative data.

The predictive failure model can be updated using federated and online learning across multiple robotic systems, with differential privacy applied to protect sensitive surgical data by sharing only model updates and not raw data. The dynamic calibration module can include a surgeon override feature allowing manual intervention during recalibration operations. An augmented reality interface can be provided and configured to overlay degradation risk scores, component condition metrics, and suggested maintenance strategies on a 3D rendering of the robotic system. As a non-limiting example, the predictive maintenance alert includes a failure mode classification, confidence score, predicted impact on surgical task fidelity, urgency score, and recommended intervention strategy. In one embodiment, the dynamic calibration module modifies actuation force, motion trajectories, servo gains, torque profiles, damping coefficients, or thermal load distributions in real-time using a staged adjustment strategy to avoid mechanical perturbations.

The sensor array can have one or more of accelerometers, strain gauges, piezoelectric sensors, acoustic emission sensors, fiber optic sensors, thermal sensors, humidity sensors, or barometric pressure sensors. A data preprocessing module can be included to clean sensor data prior to analysis by the artificial intelligence (AI) engine. The data preprocessing module can have: a noise reduction submodule to apply one or more signal processing techniques selected from the group consisting of low-pass filtering, wavelet denoising, and Kalman filtering with an outlier detection submodule to identify and exclude anomalous data points using one or more statistical or machine learning methods selected from the group consisting of z-score analysis, isolation forests, and clustering-based anomaly detection.

A normalization submodule can be included to standardize sensor input features across temporal and spatial dimensions to ensure consistency of AI-based inference. A missing data handling submodule can also be included to apply interpolation or imputation methods based on one or more of historical sensor data, real-time contextual cues, or model-based estimation. A synchronization submodule can temporally align data streams from the sensor array using timestamp correlation or cross-sensor temporal fusion algorithms.

In one embodiment, a method is provided for predictive maintenance of a surgical robotic system. Operational anomalies can be detected that include microvibration signatures, thermal deviations, or acoustic signals during a surgical procedure using a sensor array. Detected data can be analyzed using AI engine to identify predictive indicators of degradation or failure. A predictive maintenance alert can be produced if indicators exceed a dynamic threshold. Robotic system parameters can be calibrated during the surgical procedure based on the alert, without interrupting the surgical task. A visualization can be displayed of affected components and predictive analytics to the surgeon via an interface.

The indicators can be classified into risk categories and calibration intensity adjusted based on assigned category. Calibration can include redistributing actuation loads across redundant system components.

In one embodiment, a non-transitory computer-readable medium stores instructions that, when executed by a processor of surgical robotic system, cause the system to: receive operational data from a multi-modal sensor array; analyze the data using a trained AI model to detect mechanical or material degradation; predict likelihood of component failure during a procedure; generate a predictive maintenance alert with mitigation strategies; and initiate staged dynamic recalibration of robotic components using a virtual twin simulation prior to physical execution.

As a non-limiting example, a method for real-time cleaning and preprocessing of sensor data in a surgical robotic system is provided and receives multi-modal sensor data from a sensor array operatively coupled to one or more robotic components during a surgical procedure. A hierarchical noise reduction can be performed on the received sensor data using one or more techniques selected from the group of low-pass filtering, Kalman filtering, and wavelet denoising. Anomalous data points are detected and excluded using outlier detection techniques selected from the group if of z-score analysis, Mahalanobis distance, isolation forest algorithms, and clustering-based methods. Asynchronous sensor data streams can be synchronized by applying temporal alignment techniques including timestamp normalization, predictive interpolation, and cross-sensor temporal fusion algorithms. Sensor data can be normalized using statistical feature scaling techniques selected from one or more of z-score normalization, and principal component-based scaling, to ensure compatibility with AI model input requirements. Missing or corrupted sensor values are input using predictive estimation models trained on historical patterns, contextual metadata, or real-time contextual cues. Data quality metrics and signal degradation can be assessed using a feedback submodule, and an alert can be provided to the AI engine when preprocessing confidence falls below a predefined threshold. The cleaned, validated, and normalized data can be streamed to AI engine for predictive maintenance assessment and dynamic calibration during the surgical procedure.

In one embodiment, surgical robotic system includes one or more robotic components operable during a surgical procedure. A plurality of sensors produce real-time operational, physiological, or spatial data. A sensor calibration engine is coupled to the sensors. The sensor calibration engine is configured to: detect sensor drift or degradation in accuracy over time by comparing sensor outputs to one or more of: historical baselines, time-stamped reference signals, intraoperative simulation models, or expected outputs derived from anatomical landmarks; initiate an automated recalibration process in response to exceeding predefined drift thresholds, scheduled recalibration intervals, or predictions generated by a machine learning model trained to detect calibration drift based on sensor input patterns and system performance indicators; perform calibration using one or me of: redundant sensors, anatomical fiducials extracted from real-time imaging, dynamic patient-specific models, or synthetic reference environments generated by simulation; validate post-calibration accuracy using anomaly detection algorithms, statistical quality assurance metrics, or artificial intelligence models trained to detect residual calibration error, misalignment, or systemic deviation; and log each calibration event as a versioned record comprising pre- and post-calibration accuracy reports, calibration parameters used, and validation outcomes, wherein the logs are accessible for audit, traceability, or model refinement.

The calibration engine can use a neural network trained on labeled historical sensor drift events and anatomical variance to identify likely sources and magnitudes of deviation and to anticipate future recalibration needs. The automated recalibration process can be triggered during system boot-up, upon detection of anomalies by a data validation module, or prior to initiating critical surgical maneuvers, and further includes a temporal consistency module configured to monitor calibration drift trends across surgical sessions and issue predictive maintenance alerts based on trend analysis.

In one embodiment, the calibration engine supports cross-sensor modality correction, including aligning data streams from imaging sensors, force sensors, positional encoders, and haptic feedback devices using multimodal registration techniques based on anatomical fiducials derived from MRI, CT, or intraoperative ultrasound imaging. The validation engine can flag a calibration failure when the post-calibration deviation exceeds a confidence interval threshold derived from real-time Bayesian inference or ensemble learning models and generates a system alert for surgeon review.

As a non-limiting example, a robotic surgical system network includes a plurality of robotic surgical systems. Each system includes robotic arms, sensors, a surgeon console, and a control system with an integrated AI module. A network interface is associated with each robotic surgical system and provides for secure data communication. A central or distributed data repository can be coupled to the network interfaces. The data repository securely stores surgical data aggregated from the robotic surgical systems. The surgical data can include at least one of procedural data, sensor readings, imaging data, AI decision logs, surgical outcomes, and user interaction data. A training module is coupled to the data repository. The training module is configured to: utilize the aggregated surgical data to train or update AI models for the robotic surgical systems using unsupervised learning, transfer learning, and use federated learning techniques. A cybersecurity implements security measures for data transmission and system access. The security measures can include: at least one of encryption, multi-factor authentication, and real-time threat detection.

A collaboration interface can be included to enable two or more users, potentially at different locations, to interact with: intraoperative data, AI recommendations, and system controls in real time. The collaboration interface can include voice recognition with multilingual capability for verbal control and communication. As a non-limiting example, the robotic surgical system network integrates with external systems includes electronic health records (EHR) to access or update patient records. The training module can use federated learning to update global AI models while preserving data privacy by maintaining raw patient data locally. Aggregated data and AI model updates can support benchmarking and performance analytics across the robotic surgery network. Access to the surgical data can be subject to audit and permissions for purposes of: postoperative review, quality assurance, and surgical training.

An edge computing module can be provided to locally preprocess intraoperative data prior to transmission to the central repository. The preprocessing can use: filtering, compression, and metadata tagging. As a non-limiting example, a predictive analytics engine identifies potential surgical complications or anomalies in real-time by comparing intraoperative data against historical patterns stored in the data repository. The predictive analytics engine can utilize: recurrent neural networks (RNNs), temporal convolutional networks (TCNs), and adaptive AI learning strategies that dynamically respond to confidence levels, annotation density, or frequencies of surgeon override.

A decentralized ledger system can be integrated with the data repository to provide immutable logging of one or more of: surgical events, AI decisions, control handovers, model version identifiers, and procedural events. The ledger can be based on a permissioned blockchain. Access can be controlled via role-based access permissions to ensure litigation resilience and regulatory compliance.

A simulation module can be provided to generate synthetic surgical environments using anonymized surgical data for one or more of: testing, validation, and training purposes. The environments can be rendered using extended reality (XR) technologies for immersive interaction.

In one embodiment, the AI module is configured to: generate post-operative summaries, logs, or reports comprising annotated procedure timelines, alerts, and performance metrics using natural language generation and video frame annotation. A modular AI model can perform one or more of: version framework logs AI model updates, associates model versions with surgical events, and support rollback to prior model states for traceability and forensic analysis. A human-AI collaboration module can dynamically allocate control between the human operator and AI system during surgical procedures based on one or more of: real-time performance metrics, surgeon preference, and contextual complexity. In one embodiment, each robotic surgical system can have a redundancy module to maintain surgical operation continuity in the event of a subsystem failure by rerouting tasks to backup hardware or cloud-based virtual machines. A data quality validation engine can be provided to act for one or more of: identify anomalous, incomplete, or corrupted surgical data using statistical modeling and anomaly detection algorithms prior to inclusion in the central repository or training datasets. In one embodiment, the network interface supports real-time telesurgery control by authenticated surgeons over high-bandwidth, low-latency communication links with redundant failover paths. The AI module can include an explainable AI (XAI) component configured to generate human-interpretable rationales for intraoperative decisions or recommendations. The explainable AI module can use attention heatmaps and textual justifications aligned with medical ontologies.

In one embodiment, control handoff decisions are governed by a reinforcement learning model trained on surgeon-AI interaction logs. A virtual machine failover can include real-time containerized instances replicating the control system's execution state. A sensor data preprocessing engine can be included to: filter, normalize, and validate sensor inputs prior to AI model inference. The preprocessing engine can utilize statistical anomaly detection, noise filtering, and data reconstruction techniques to enhance input fidelity.

In one embodiment, in the robotic surgical system operates in cloud-native virtual environments, enabling elastic compute scaling and geographic distribution of surgical intelligence. Each robotic surgical system can use containerized microservices responsible for one or more of: control commands, vision processing, and AI inference, orchestrated by a distributed container management platform. A multi-modal interaction interface can be provided to receive and integrate inputs from voice commands, gaze tracking, and haptic sensors located at the surgeon console. A collaborative data governance module enforces one or more of: region-specific privacy rules, data retention schedules, anonymization protocols, and role-based access control across the robotic surgery network.

A synthetic data generation module can be provided to: augment training datasets using generative adversarial networks (GANs) trained on validated surgical cases stored in the data repository. The synthetic data generation module can simulate: rare complications, anatomical variations, and hardware failure scenarios. A semantic abstraction engine can be used to map intraoperative signals and AI decision events to structured clinical ontologies for improved interpretability and auditability. A regulatory compliance engine can be provided to: monitor, log, and manage surgical data transactions and AI decision events; enforce region-specific regulatory requirements related to patient data privacy, retention, and auditability, including at least one of HIPAA, GDPR, FDA, or MDR; automatically trigger compliance workflows including consent verification, access audit generation, and redaction of protected health information (PHI); and generate real-time compliance alerts or reports based on deviations from regulatory rulesets or data handling policies.

The regulatory compliance engine can include one or more of: a rules engine configured to interpret and apply jurisdiction-specific policies based on geographic metadata associated with the surgical case; integration with the system's decentralized ledger to immutably record regulatory audit trails for AI-driven decisions and control transitions; dynamic redact or mask sensitive data fields in surgical logs or AI outputs based on the role and clearance level of the accessing user; have a consent management module configured to verify, store, and audit patient consent status prior to enabling data sharing or training module updates Real-time alerts can be transmitted to system administrators or compliance officers upon detecting violations such as unauthorized data access, excessive retention, or transfer of patient data outside approved jurisdictions. An automated generation of machine-readable compliance reports can be provided for submission to regulatory authorities or institutional review boards (IRBs). Periodic audits of data retention and deletion policies can be provided against institutional schedules with automated purging of expired data in accordance with those policies.

In one embodiment, a method is provided for adaptive force management in the robotic surgical system. Real-time data can be received, by one or more sensors, indicative of tissue mechanical properties during a surgical procedure. The real time data can include one or more of: pressure, shear stress, strain, ultrasonic elasticity, optical coherence tomography data, magnetic resonance elastography data, and capacitive force measurements. The real-time data can be processed using a trained deep learning model to predict one or more of: tissue-specific force thresholds, tissue deformation behavior, and mechanical response characteristics. In response to the predicted force thresholds, adjustments can be to one or more at least one of: a grip force, tension, or compression force applied by a robotic actuator in real-time; and continuously refine the deep learning model during the surgical procedure based on intraoperative feedback data using online learning algorithms. Patient-specific tissue interaction safety profiles can be autonomously generated that are derived from biomechanical response forecasting. The profiles can be used for safe force can be detected from modulation and are not based on prior surgical task trajectories or procedural templates. Deviations from expected tissue behavior in real-time can be determined. The applied forces can be autonomously modified to: maintain safe mechanical interaction; generate a visual, auditory, and haptic alerts produced if the predicted safe force thresholds are at risk of being exceeded. Control signals can be output to the robotic actuator and optimize interaction forces between the robotic system and the tissue to minimize tissue damage and improve surgical outcomes.

The deep learning model can include one or more of: a convolutional neural network, recurrent neural network, transformer model, graph neural network, and a hybrid architecture. Intraoperative model updates can be performed using a hybrid federated and online learning strategy restricted to one or more of: force response feedback, excluding visual, task-based, or historical procedural data, and employ privacy-preserving aggregation based solely on mechanical signal deviations. Tissue deformation predictions can incorporate viscoelastic modeling parameters derived from time-resolved strain measurements. Predictive force profiles can be adjusted in response to detected physiological signals such as tissue perfusion changes or blood flow alterations. A digital surgical force profile log can be maintained for post-operative analysis, surgeon training, and predictive analytics. In one embodiment, autonomous force modification can include simultaneously adjusting multiple actuators in coordinated patterns to minimize overall tissue stress.

AI processing module can create a personalized surgeon haptic profile based on one or more of: prior case history, behavioral metrics, and real-time performance to tailor feedback signals dynamically. A haptic feedback device can be integrated into a surgeon console. The haptic feedback device can render tactile sensations derived from mechanical compliance differentials in real-time tissue resistance, without relying on image-based object recognition or visual cue synchronization. As a non-limiting example, AI module can be configured for one or more of: generate adaptive haptic feedback signals by modifying raw sensor data through scaling, filtering, augmentation with virtual compliance or texture data, or simulation of anticipated force variations; create a personalized surgeon haptic profile based on prior case history, behavioral metrics, and real-time performance; and generate haptic boundary alerts when a surgical instrument 18 approaches predefined anatomical structures or safety zones. A feedback calibration module can be included to automatically adjust haptic signal parameters based on surgeon-specific thresholds, tool variations, and sensor drift. A biometric authentication module can be integrated into the surgeon console to ensure secure access and user-specific customization of haptic feedback settings. System can also include one or more of: a cloud-based analytics module configured to collect intraoperative sensor and haptic data, perform longitudinal performance analysis, and update machine learning models using federated learning across multiple procedures.

A surgeon training mode can be included that simulates tissue interactions in a virtual environment using synthesized haptic signals for skill acquisition and rehearsal. A latency compensation algorithm can specifically preserve temporal fidelity in haptic signal rendering based on actuator force feedback timing, excluding correction of video or motion command delays. A biometric authentication module can be integrated into the surgeon console to ensure secure access and user-specific customization of haptic feedback settings. System can include a surgeon training mode that simulates tissue interactions in a virtual environment using synthesized haptic signals to facilitate skill acquisition and rehearsal. As a non-limiting example, the haptic feedback device is enhanced with synchronized audiovisual cues to provide multi-sensory situational awareness. System can include a latency compensation algorithm for telesurgical operations to maintain temporally accurate and synchronized haptic rendering during remote procedures.

In one embodiment, the robotic surgical system includes one or more robotic actuators configured to interact with biological tissue during a surgical procedure. A plurality of sensors can include at least one of: fiber Bragg grating sensors, piezoelectric strain sensors, and magnetostrictive sensors to capture real-time mechanical, elasticity, or deformation data from biological tissues. A deep learning engine can be trained on a dataset that includes tissue mechanical responses across multiple tissue types, pathological states, and patient demographics. A control module can be configured for one or more of: dynamically modulate actuator output using a predictive tissue safety envelope generated from patient-specific mechanical profiles and real-time anomaly correction. Modulation can be limited to force domain control within estimated safe boundaries distinct from motion optimization processes. Pre-contact predictive adjustment profiles can be generated for anticipated tissue interactions using preoperative imaging data registered to intraoperative coordinates. Intraoperative deviations can be detected from predicted mechanical behavior and autonomously recalibrate actuator forces. Upcoming surgical maneuvers can be anticipated based on prior task sequences and adjust actuator stiffness or damping properties in preparation for anticipated contact. An emergency can be initiated to override actuator forces via an anomaly detection module when real-time sensor data deviates beyond a threshold from the predicted safe mechanical response range. A feedback loop can be provided to iteratively refine the deep learning engine during the procedure using one or more of: supervised learning updates, anomaly detection, and reinforcement learning strategies. The reinforcement learning model can be shared across procedures to optimize distributed actuator force patterns for minimizing localized and cumulative tissue stress.

An imaging system can include real-time spectral or hyperspectral imaging for enhanced tissue classification. A user interface can be used for one or more: presentation of real-time estimated tissue fragility metrics, recommend force adjustments, and actionable alerts. Adaptive haptic feedback parameters can be dynamically tailored based on user behavior metrics including force application patterns and response times.

In one embodiment, a non-transitory computer-readable medium stores instructions that: when executed by one or more processors, cause a robotic surgical system to: acquire real-time intraoperative sensor data indicative of tissue mechanical characteristics; process the acquired data using a trained deep learning model to predict optimal force application strategies; dynamically adjust actuator grip force, tension, or compression in response to the processed data; predict tissue type classification based on real-time mechanical signature analysis; detect deviations from expected tissue responses and adjust force parameters autonomously; update the deep learning model parameters intraoperatively based on observed mechanical responses and outcomes; and generate real-time alerts or graphical overlays indicating estimated tissue fragility and recommended force modifications.

As a non-limiting example, instructions 67 can further cause system 10 to adaptively switch between different force application regimes based on detected mechanical heterogeneity within the same tissue type. The real-time graphical overlays can include one or more of: (a) force-domain visualizations indicating compliance thresholds and mechanical stress zones based solely on intraoperative sensor feedback; and deformation-based visual risk indicators excluding anatomical segmentation or image-derived tissue classification. The latter can be generated based on force modeling to assist in intraoperative navigation and reduce the risk of tissue injury.

In one embodiment, a method for robotic surgery receives multimodal intraoperative data, including both real-time mechanical sensor data and intraoperative imaging data. The multimodal data is fused using a deep learning model trained to correlate tissue deformation patterns with image-derived tissue features. Predictive actuator force profiles are generated based on fused data. Applied force parameters are dynamically adjusted in real time during tissue manipulation. The model weights are updated intraoperatively using reinforcement learning based on deviations from predicted versus actual deformation outcomes.

In another embodiment, a method is provided for generating a tissue mechanical behavior map from preoperative imaging data. The map is registered to intraoperative coordinates. Robotic actuator force parameters are calibrated based on predicted local tissue mechanical profiles prior to tissue contact. The parameters are refined in real time during the procedure using sensor feedback.

In one embodiment, multiple robotic actuators collaboratively optimize force distribution using a shared deep reinforcement learning model to minimize cumulative tissue stress across a surgical site. Tissue mechanical risk zones can be assessed in real-time. Robotic tool trajectories are dynamically modified to avoid high-risk deformation regions; and continuously updating the risk model using live mechanical feedback.

In one embodiment, robotic surgical system 10 includes a robotic instrument 18 configured to interact with biological tissue. A sensor array is disposed on or within the instrument and configured to detect real-time tissue interaction parameters including at least one of: compliance, stiffness, texture, temperature, electrical impedance, or optical properties. A haptic feedback interface provides tactile signals to a surgeon at a surgeon console. A control module has at least one processor and memory storing instructions that, when executed, implement an artificial intelligence (AI) system. AI system is operable to execute one or more of: classify contacted tissue types using a machine learning model trained on a dataset of annotated surgical interactions and sensor data; determine a haptic feedback profile corresponding to the classified tissue type; dynamically adjust the haptic feedback interface based on at least one of instrument 18 tip velocity, applied force, user-specific preferences, or the surgical phase; and update the haptic profile in real-time based on intraoperative sensor inputs and classification confidence metrics. The robotic surgical system of claim 1, further comprising a safety module configured to detect hazardous or high-risk tissue interactions and override or modulate robotic motion or haptic feedback to prevent tissue injury.

The sensor array includes at least one of: capacitive, piezoelectric, ultrasonic, optical coherence tomography (OCT), photoacoustic, thermal, or bioimpedance sensors. The OCT sensor provides high-resolution optical measurements to improve classification of layered or vascularized tissue. The AI system can include the machine learning model, the decision engine, and the dynamic update mechanism. The machine learning model has at least one of: a convolutional neural network (CNN), recurrent neural network (RNN), transformer model, support vector machine (SVM), or an ensemble learning framework.

The robotic surgical system of claim 1, further comprising a personalization module operatively integrated with the artificial intelligence system, wherein the personalization module is configured to calibrate haptic output based on a surgeon's skill level, interaction history, or intraoperative decision latency. The personalization module employs reinforcement learning to refine haptic patterns based on surgical outcomes, error rates, or post-procedural feedback. A comparator module and database storing predefined haptic profiles for known tissue types. The comparator synthesizes a real-time feedback profile by matching sensor inputs with stored profiles. The haptic feedback interface supports multimodal outputs including at least two of: vibrotactile, kinesthetic force, auditory tones, or visual cues.

A recalibration module can be provided that detects end-effector tool changes and re-maps sensor signal interpretation and haptic actuation parameters accordingly. System 10 can generate a real-time confidence score for each tissue classification and modulates feedback strength proportionally. Feedback for neoplastic, inflamed, or necrotic tissue is distinguishable from healthy tissue to guide surgical decision-making. An augmented reality interface can be provided to overlay tissue classification or haptic events visually via a head-mounted display or microscope view. The control module can generate predictive haptic feedback based on preoperative imaging data and anticipated surgical maneuver. This allows the surgeon to perceive expected tissue resistance prior to contact.

AI system can fuse multimodal sensor data using an attention-based fusion model or cross-modal learning framework to improve classification fidelity. Feedback waveform parameters can be defined by variable modulation of amplitude, frequency, pulse duration, or oscillatory pattern to match tissue biomechanics. System 10 can support collaborative multi-user sessions and selectively personalizes haptic feedback for each surgeon based on real-time identity tracking. An intraoperative simulator can generate predicted haptic sensations based on planned surgical trajectories and preoperative imaging.

A method provided adaptive haptic feedback during robotic surgery. Tissue interaction parameters can be detected via a sensor array on a robotic instrument. Tissue type is classified using a trained machine learning model. A feedback profile can be determined based on classification and system confidence. Multimodal haptic output is dynamically delivered. The feedback is adaptively updated based on real-time force, trajectory, surgeon behavior, and surgical phase. The machine learning model is updated postoperatively using new intraoperative data to improve future classification and feedback relevance.

Figure 32:
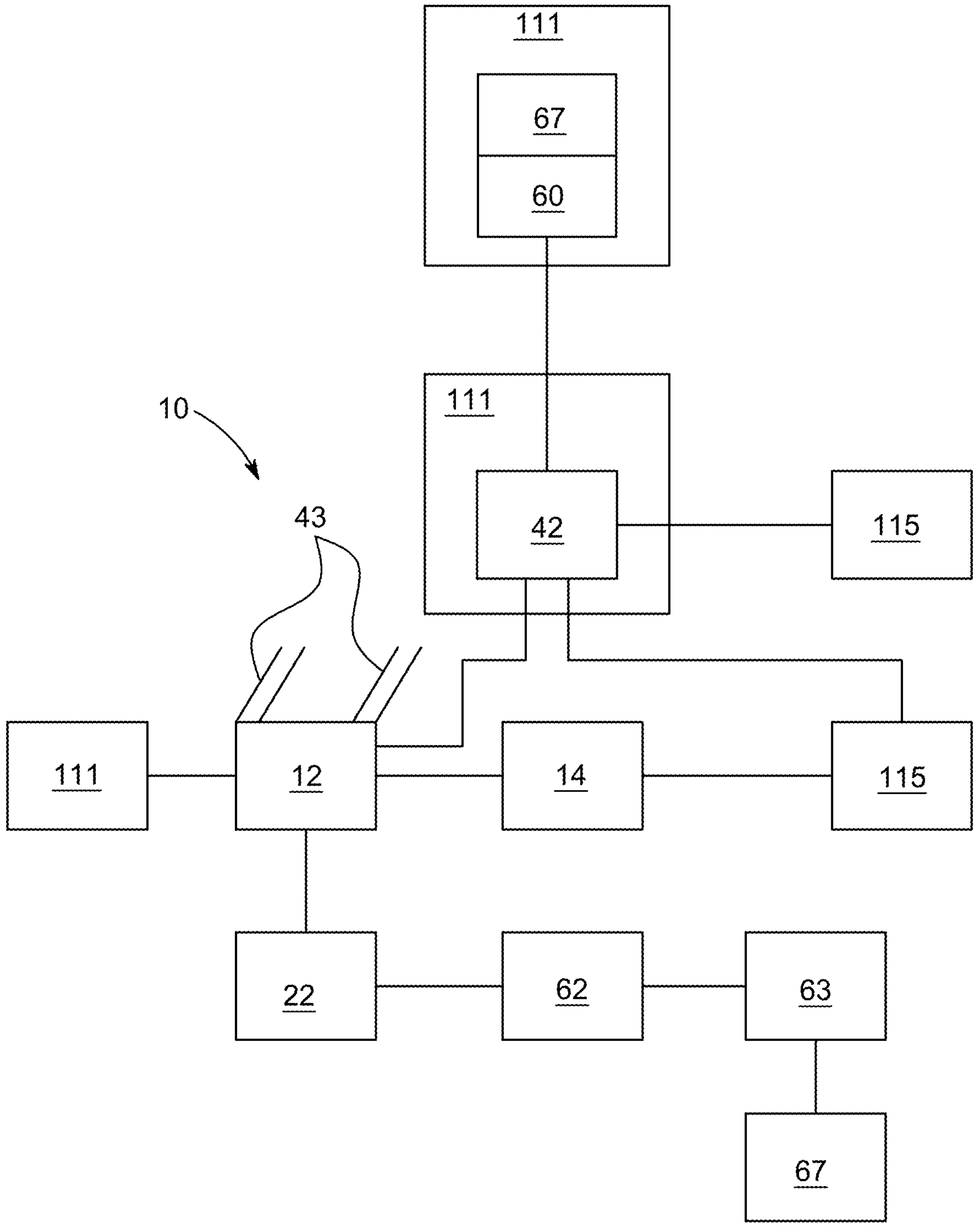
FIG. 32 illustrates one embodiment of a robotic surgical system with AI of the present invention.

FIG. 32 illustrates one embodiment of robotic surgical system 10 including: a surgeon console 12 operatively connected to one or more robotic arms 43; and a control system 22 with at least one processor 62 and memory 63 storing instructions 67 that, when executed, cause the control system 22 to perform one or more of: receive real-time intraoperative data with at least one of instrument 18 telemetry, anatomical imaging, sensor input, or surgeon interaction patterns; query a model registry storing a plurality of AI system 42 inference models, each associated with metadata comprising procedural domain, training provenance, performance benchmarks, and override statistics; compute a model-context alignment score using at least one of similarity metrics, reinforcement learning-based alignment, or a hybrid inference; select and deploy an AI system 42 model based on the alignment score to generate intraoperative guidance; operate a temporal forecasting module 111 to anticipate model performance degradation or contextual divergence; initiate a model arbitration event prior to predicted degradation, with at least one of dynamic model switching, ensemble inference, concurrent dual-model execution, or notification to the surgeon; monitor model confidence levels and execute a fallback response when the confidence metric falls below a surgeon-adjustable reliability threshold. AI-generated outputs are annotated with version identifiers, confidence scores, and inference metadata for traceability and retrospective audit.

A method for AI-assisted risk-aware surgical decision support receives real-time intraoperative signals during a robotic surgical procedure. A cohort of historical procedures is identified from a federated, privacy-preserving surgical database 61 based on case-matching criteria. Dynamic risk forecasts are computed for upcoming surgical steps using population trends, patient-specific features, and procedural context. Predictive alerts are deliver4ed to the console 12, including projected complication likelihoods and recommended procedural adjustments. Risk estimates are updated as new intraoperative signals. AI system 42 model selection and arbitration strategies are adaptively modified based on real-time risk updates, system confidence degradation, and surgeon interactions.

Robotic surgical system 10 can include a variety of engines such as those selected from: AI, safety transition, predictive duration, postoperative learning, safety transition, predictive learning, postoperative learning, deviation resolution, deviation modelling, feedback modulation, multimodal fusion, federated learning, collaboration, machine learning, model generation, activity, workflow optimization, learning based, data fusion, procedural urgency, image fusion, analysis, boundary mapping, and the like, collectively referred to as engine 115.

Robotic surgical system 10 can be configured for safety-based autonomy transitions, A control system 22 configured to execute autonomous or semi-autonomous surgical functions. A safety transition engine 115 is configured to: monitor operational metrics including confidence, sensor fidelity, task complexity, and patient-specific physiological parameters; compute a cumulative uncertainty index over a sliding time window; compares the uncertainty index to task-specific safety thresholds; initiates transition from autonomy to reduced-autonomy or manual mode when thresholds are exceeded; and logs contextual data including system state, procedural phase, surgeon response, and environment variables for postoperative review and model refinement.

The temporal forecasting module 111 includes a recurrent neural network, transformer-based time series model, or a Bayesian sequence model trained on annotated intraoperative datasets. The model registry is federated across surgical institutions and updated via differential privacy protocols to protect patient confidentiality. A visualization can be provided to: overlay AI system 42 predictions and divergence indicators on live surgical video feeds; display model certainty intervals and can have tissue prediction heatmaps.

The arbitration strategy can include real-time ensemble voting based on model confidence, prediction divergence, and contextual salience weighting. A surgeon interface is provided that: displays transparency indicators including interpretability scores and feature importance; allows manual override of AI system 42 guidance and logs such events with timestamp and justification metadata. An alert modulation module 111 can be included to adjust alert sensitivity where delivery modality, and frequency are based on intraoperative behavior patterns including override rate and attention metrics.

Model arbitration can be performed asynchronously to minimize latency during critical control intervals. A regulatory compliance module 111 is configured to: validate real-time model usage against jurisdiction-specific legal and ethical rules; as well as record an immutable audit trail of AI system 42 inferences, override events, model transitions, and feedback annotations.

System 10 can include a simulation and pre-selection module 111 configured to: receive preoperative imaging and case metadata; and simulate model performance in virtual scenarios; recommend primary and fallback AI system 42 models based on contextual fit and surgeon preferences, and the like. System 10 can include a predictive duration engine 115 to estimate remaining surgical time by analyzing instrument 18 motion, video patterns, and procedure-specific models. In one embodiment, inference execution is dynamically distributed between local edge computing and cloud-based environments based on latency constraints and model complexity. A surgeon personalization module 111 configured to adapt inference behavior to the preferences and past override history of the operating surgeon. In one embodiment, each AI system 42 model includes an embedded explainability module 111 that: generates human-readable or visual explanations for each inference; and enables retrospective justification for override events.

In one embodiment, the fallback threshold for arbitration or manual control transition is configurable via the console 12 in real time, enabling tailored automation aggressiveness. A postoperative learning engine 115 configured to: extract retraining data from override, arbitration, or adverse event instances; and curate feedback-enhanced datasets for continual model improvement. In one embodiment, the reduced-autonomy state retains passive AI system 42 recommendations but requires surgeon validation before execution of any robotic movement. The safety transition engine 115 can include a hierarchical fallback controller 92 that enables: partial module 111 disablement based on localized sensor 84, 88 or model degradation; and allow for full transition to manual operation upon system-wide failure or override conditions.

Robotic surgical system 10 can include: comprising: a simulation module 111 configured to generate and continuously update a dynamic, patient-specific digital twin of an anatomical region during a surgical procedure, with the digital twin having mechanical, thermal, and physiological representations; a data acquisition module 111 with a multi-modal sensor 84, 88 array to collect intraoperative data from surgical tools and patient tissues, the data including at least one of: force feedback, temperature, pH, electrical impedance, light reflectance, acoustic emissions, chemical markers, or volatile biomarkers; an AI system module 111 coupled to the data acquisition and the simulation module 111, the module 111 is used to execute one or more of: analyze sensed data to characterize tissue condition and identify regions of clinical interest; simulate tool-tissue interactions and forecast anatomical responses prior to execution of robotic tool movements; generate real-time visualizations of characterized tissue regions and predicted responses; and assign a confidence score to tissue classification results and adjust sensing parameters. Control system 22 modifies surgical tool trajectories or parameters based on outputs from the AI system module 42, including adaptive adjustments in response to classification confidence or margin proximity. A visualization interface presents a real-time representation of the digital twin and AI-generated insights to an operator, including augmented reality overlays indicating high-risk anatomical zones, tissue classifications, and tumor margins, with dynamic confidence heatmaps.

As a non-limiting example, the digital twin includes perfusion, hydration, and tissue compliance layers that can be estimated using multispectral imaging, impedance analysis, and Doppler-based sensing. The multi-modal sensor 84, 88 array in at least one of: Raman spectroscopy, fluorescence spectroscopy, hyperspectral imaging, diffuse reflectance spectroscopy, pH sensors, oxygenation sensors, or volatile organic compound detectors. The AI system module 42 can have a machine learning model selected from one or more of: neural networks, support vector machines, and random forest classifiers trained on clinically annotated datasets comprising multispectral, chemical, and molecular data. The AI system module 42 can dynamically adjust one or more sensor 84, 88 parameters including wavelength, intensity, pulse duration, or sampling rate based on classification confidence. The visualization interface can overlay heatmaps, tool trajectory confidence bands, and tumor margin boundaries in a 3D rendering of the anatomical region.

A feedback module 111 can provide auditory alerts or haptic signals to the surgeon when the tool approaches a high-risk or pathological region. The system of claim 1, further comprising an automatic calibration module 111 configured to recalibrate sensors 84, 88 in response to intraoperative environmental or tissue state changes. An intraoperative navigation and instrument 18 guidance subsystem that adapts in real time to AI-characterized tissue features and predicted tool-tissue outcomes. A data management module 111 can securely transmit anonymized intraoperative sensing data to a remote AI system 42 training infrastructure using federated or distributed learning algorithms.

In one embodiment a non-transitory computer 151-readable medium is provided that stores instructions 67 that, when executed by one or more processors, 62 cause a robotic surgical system to: receive intraoperative data from sensor-equipped surgical tools and patient anatomy; generate and continuously update a dynamic, patient-specific digital twin of an anatomical region; analyze the data using an AI system 42 module 111 to characterize tissue conditions, simulate potential tool interactions, and identify pathological tissue margins; compute and issue robotic control commands to reduce procedural risk based on predicted outcomes and tissue classifications; generate auditory or haptic feedback to the surgeon based on proximity to critical regions or margin boundaries; and display a live visualization of the digital twin with predictive overlays, confidence heatmaps, and real-time adjustments based on instrument 18 movement or tissue property changes.

Instructions 67 cause the system to present overlay indicators distinguishing normal, neoplastic, and malignant tissue in distinct visual patterns or colors. Instructions 67 further cause the system to compute and display classification confidence scores and reconfigure sensing strategies based on the scores. The predictive overlays dynamically update in response to surgical instrument 18 movement or changes in classified tissue geometry. The optical signatures used for classification include at least one of: tissue absorption spectra, scattering coefficients, autofluorescence, Raman spectra, or polarization shifts. Instructions 67 can also cause system 10 to stream live digital twin data and predictive feedback to a remote expert system for collaborative surgical support.

In another embodiment, a method of robotic surgical assistance is provided that: acquires real-time physiological, chemical, and optical data from a surgical site using intraoperative sensors 84, 88; constructs a patient-specific digital twin incorporating the data, wherein the digital twin includes multiple physiological and biomechanical layers; analyzes the acquired data using an AI system module 42 to characterize tissue conditions and simulate proposed surgical tool actions; generates tool trajectory modifications, feedback cues, or alerts based on simulation results and tissue characterization confidence; and renders the digital twin and associated predictions on a user interface during surgery, including augmented reality overlays indicating tissue classifications, resection boundaries, and risk assessments.

The rendered visualization can include color-coded overlays indicating tumor margins, risk zones, or instrument 18 trajectory risk gradients. Instructions 67 can be stored that, when executed by one or more processors 62, cause a robotic surgical system to: receive intraoperative data from sensor 84, 88-equipped surgical tools and patient anatomy; generate and continuously update a dynamic, patient-specific digital twin of an anatomical region; analyze the data using an AI system module 42 to characterize tissue conditions, simulate potential tool interactions, and identify pathological tissue margins; compute and issue robotic control commands to reduce procedural risk based on predicted outcomes and tissue classifications. Auditory or haptic feedback can be produced. The surgeon can then use it based on proximity to critical regions or margin boundaries. Display 32 can be used for a live visualization of the digital twin with predictive overlays, confidence heatmaps, and real-time adjustments based on instrument 18 movement or tissue property changes. The digital twin can be used postoperatively for retrospective analysis, simulation replay, or surgical training. The feedback cues can be real-time auditory tones or tactile pulses corresponding to confidence thresholds in tissue classification.

#No. 12

Robotic surgical system can include: a robotic surgical instrument 18 coupled to a controller; and an imaging module 111 to capture real-time visual data of a surgical field. A deviation detection module 111 includes: a procedural deviation detector, that can be error detector, to identify intraoperative discrepancies between a predefined surgical action sequence and actual robotic execution using a deviation threshold based on trajectory variance and feature inconsistency that can use image recognition database 43. Detector 122 have a trained machine learning model to enhance sensitivity to context-specific deviations without triggering autonomous inference chains. A temporal context buffer stores prior motion vectors and classification results for deviation analysis and correlation. A deviation resolution engine 115 performs one or more of: distinguishing between micro-level kinematic deviations and macro-level procedural path shifts; correct micro-level deviations using vector smoothing and damping algorithms; correct macro-level deviations by replanning motion limited to the current procedural subtask. The correction parameters are modulated by AI-driven risk classifiers operating within a predefined response policy. A logging module 111 stores deviation-triggered corrections as procedural exception events, annotated with one or more of: timestamp, tool parameters, and robotic state context. Robotic action revisions occur within a tolerance band defined by a surgical plan boundary map. This is achieved without activating inference model arbitration or fallback artificial intelligence logic.

System 10 can include a visualization interface to overlay deviation indicators on a real-time surgical display, where: the overlays are synchronized with motion revision timestamps and direction vectors; and color coding and symbols indicate deviation magnitude, frequency, and severity based on surgical plan metadata. The procedural deviation detector, such as detector 122, monitors for tool-tissue interaction anomalies comprising unexpected displacement, vibrational anomalies, or direction reversals exceeding a vector divergence threshold. The temporal context buffer stores motion data for a trailing window of 2-10 seconds and suppresses transient deviations caused by occlusion, instrument 18 jitter, or visual noise. A hybrid supervision layer monitors deviation frequency and overrides automated corrections when the rate exceeds a deviation saturation threshold, initiating a supervisory arbitration protocol. The supervisory arbitration protocol triggers a fail-safe visual, auditory, or haptic alert to the surgical team when deviation density exceeds a predefined safety limit. A deviation learning module 111 configured to update deviation detection thresholds based on postoperative analytics, while maintaining fixed thresholds during live procedures. A patient-specific deviation modeling engine 115 modifies deviation thresholds preoperatively using anatomical complexity scores, tissue compliance, and motion artifact risks. Controller includes a surgeon override interface that allows real-time toggling between autonomous correction mode and surgeon-guided correction mode.

Motion correction within the deviation resolution engine 115 is executed without triggering model arbitration, fallback AI system 42 logic, or cloud-inference decision support. System 10 is configured for minimally invasive surgery, and deviation thresholds are dynamically tightened based on trocar-based spatial constraints. A deviation lockout mode is triggered when deviation frequency exceeds an emergency threshold, halting all autonomous corrections and issuing an override notification to the surgical team. Deviation resolution decisions are governed by phase-specific priority logic, modulating response urgency based on criticality of the current procedural step. Controller can include encrypted memory 63 partitions for separate storage of deviation logs and quality control events to support regulatory compliance.

In one embodiment, a method is provided for deviation-triggered intraoperative motion correction in robotic surgical system 10, and includes: receiving, by one or more processors 62, real-time intraoperative video and sensor 84, 88 data; detecting a deviation from a planned trajectory using a rules-based deviation detection model, without engaging adaptive behavior models or surgeon-specific profiles; applying motion correction locally by modifying one or more of robotic instrument 18 speed, force, or endpoint trajectory within a defined tolerance zone; dynamically adjusting deviation thresholds based on anatomical region and procedural risk score; and logging the motion correction in an encrypted procedural audit record.

A confidence score is assigned to each deviation, based on deviation magnitude, spatial density, and similarity to prior procedural exceptions. Correction is suppressed when the confidence score falls below a defined threshold to reduce false positive deviation corrections. Deviation-triggered corrections are stored in a revision log isolated from any cloud-based update or real-time teleoperation inference loop. Deviation impact severity is classified by a machine learning model trained on historical adverse surgical events, and corrections are prioritized. Intraoperative risk scores are generated using preoperative anatomical heatmaps and deviation clustering metrics.

#No. 13

Robotic surgical system 10 can includes: a user behavior monitoring module 111 to track real-time and historical surgeon interaction patterns; a biometric data aggregator to receive signals from at least one of: heart rate variability sensors 84,88, electrodermal activity sensors, pupillometry, and eye tracking. A feedback modulation engine 115 is coupled to an artificial intelligence inference system. Feedback modulation engine 115 includes: a feedback timing controller to adjust the timing, frequency, and modality of intraoperative feedback based on a detected surgeon profile; a phase classifier to determine surgical phase criticality using instrument 18 telemetry, surgeon interaction dynamics, and contextual signals. A guidance controller executed one or more of: defer, escalate, or suppress feedback during high-criticality intervals and trigger contextual replays post-procedure with synchronized annotations and rationale. A surgeon profile manager has a database 61 storing individualized feedback configurations, interaction histories, and override behaviors. The manager applies these profiles across multiple procedures. A summary dashboard module 111 present post-procedure metrics including: alert suppressions, feedback acceptance rates, override behavior trends, and biometric-derived responsiveness indices.

A multimodal fusion engine 115 interprets concurrent verbal and gestural commands using a transformer-based encoder-decoder architecture. Ambiguities are resolved using surgeon profiles, criticality weighting, and confidence scoring logic.

In one embodiment, robotic surgical system included a federated learning engine 115 configured to train feedback modulation policies using anonymized behavior-response logs across distributed systems without exposing raw surgeon-identifiable data. A reinforcement learning AI system inference module 111 optimizes alert delivery timing and modality based on performance metrics, including override frequency, feedback compliance, and patient outcome data. A surgeon-AI system 42 collaboration engine 115 dynamically adjusts feedback delivery, task prioritization, and decision support based on the surgeon's real-time responsiveness index, contextual workload, and criticality of procedural phase. The biometric data aggregator generates a composite real-time surgeon responsiveness index incorporating gaze fixation duration, interface interaction latency, and physiological indicators of cognitive load. As a non-limiting example, the feedback modality included at least one of: augmented reality (AR) overlays; spatialized audio prompts; haptic signals via palm-rests or foot pedals; and dynamic lighting adjustments on the surgical console.

Feedback escalation can include a staged protocol for low-confidence AI system 42 predictions, progressing from subtle visual cues to audio or haptic reinforcement based on surgeon non-responsiveness or rising biometric stress signals. The guidance controller logs suppression events along with contextual metadata, including phase timing, alert content, rationale, and biometric readings, for correlation with postoperative outcomes. The contextual replay module 111 allows surgeon tagging of re-presented feedback as relevant, non-urgent, or suppressible, and uses annotations to retrain alert-generation models. The summary dashboard includes phase-wise segmentation of responsiveness trends, visual heat maps of attention, and AI-inferred fatigue indicators. A procedural context analyzer fused intraoperative telemetry, ambient operating room noise levels, anesthesia vitals, and surgical tool usage to fine-tune feedback delivery parameters. The profile manager includes a version-controlled configuration system enabling rollback or simulation-based testing of alternative feedback strategies. The fusion engine 115 assigns modality-specific confidence scores and uses arbitration logic to resolve input conflicts when ambiguity exceeds a defined threshold. The federated learning engine 115 can utilize differential privacy and homomorphic encryption to preserve data anonymity.

The collaboration engine 115 also logs feedback allocation decisions and updates multi-user behavioral models accordingly. A conflict resolution module 111 detects and resolves discrepancies between surgeon-issued commands and AI-generated guidance, using one or more of: surgeon behavioral profiles, real-time responsiveness indices, contextual phase criticality, or predefined prioritization rules. An external synchronization interface transmits annotated feedback replays to surgical training platforms, including audiovisual overlays and decision rationale logs. System 10 can adaptively modify interface layout, font size, icon arrangement, and highlight intensity based on the surgeon's historical gaze map and interaction preferences.

Alert suppression thresholds are dynamically adjusted during a procedure based on real-time operating room ambient conditions, such as noise or distractions. Wearable biometric sensors can be provided for remote surgeon monitoring and fatigue trend detection over time. System 10 generates a postoperative simulation replay for training or review, incorporating surgeon-specific annotations, biometric overlays, and AI system 42 feedback trajectories.

Robotic surgical system 10 can be configured for dynamic legal and ethical compliance. A control processor 62 executes surgical procedures based on AI-generated guidance. A compliance module 111 is associated with the control processor 62 and configured to: receive jurisdiction-specific surgical requirements and patient-specific consent data from external or internal sources; monitor surgical actions and AI-generated decisions in real time; analyze decision pathways using rule-based logic, predictive models, or both to detect potential legal or ethical conflicts; and initiate at least one of: issuing a conflict alert, inhibiting automated execution of the decision, or prompting a confirmation action by a human operator. A policy ingestion system interpret compliance directives expressed in natural or semi-structured language, including regulatory standards, institutional protocols, and cultural norms. A data integrity layer has a distributed ledger or immutable logging system, configured to chronologically record compliance-relevant events, including conflict detection, response actions, and system overrides.

The compliance module 111 can include a machine learning engine 115 trained on historical surgical records and prior compliance outcomes to enhance detection accuracy and context sensitivity over time. The policy ingestion component supports multilingual and cross-jurisdictional parsing of compliance documents. The logging system is based on a blockchain framework and further configured to synchronize with third-party compliance registries or accreditation bodies. A surgeon interface presents visual conflict indicators, suggested alternatives, and override options in real time during surgical procedures. The compliance module 111 receives real-time regulatory updates from a cloud-based repository or governmental database.

The system architecture supports decentralized or federated AI models for compliance decision-making, enabling local adaptation without loss of global oversight. The compliance module 111 integrates with electronic health records (EHR) to retrieve and update patient consent and compliance data. The control processor 62 adjusts surgical plans dynamically in response to detected compliance conflicts. A feedback mechanism allows surgical teams to input post-operative compliance evaluations into the system. The compliance module 111 includes a user-configurable threshold for conflict sensitivity.

In one embodiment, a method for managing legal and ethical compliance in robotic surgical system 10, receives regulatory directives and patient-specific consent inputs relevant to a surgical context; generates and executes surgical guidance using an AI-driven inference; monitors AI decisions and system actions during the procedure; evaluates such decisions against known compliance rules using a combination of rule-based logic and predictive modeling. Conflicts are detected that are indicative of a legal or ethical breach. In response to conflict detection, system 10 performs at least one of: halting system operation, issuing a surgeon prompt, logging the event, or adapting the surgical plan.

As a non-limiting example, the compliance model is updated based on feedback from surgeon decisions and post-operative assessments. Evaluation of decisions includes: weighting factors based on patient demographics, surgical complexity, and institutional risk thresholds. A compliance report is created that summarizes detected conflicts, resolutions, and system performance metrics post-procedure. In one embodiment, system 10 logs are accessible to authorized regulatory bodies for audit purposes.

In one embodiment, a non-transitory computer 151-readable medium stories instructions 67 that, when executed by processor 62 in robotic surgical system 10, cause system 10 to: acquire jurisdiction-specific compliance rules and patient consent directives; monitor and analyze AI-driven surgical actions during a procedure; detect legal or ethical conflicts using hybrid logic models; log conflict events immutably; and output interactive alerts or intervention options to a surgical team based on the conflict classification.

The computer 151-readable medium provides system 10 with real-time suggestions for alternative surgical actions when a compliance conflict is detected instructions 67 further cause the system to adapt compliance rules based on machine learning insights derived from aggregated surgical data. System 22 is configured to simulate potential compliance conflicts prior to procedure initiation, providing pre-operative risk assessments.

Robotic surgical system 10 can incorporate AI. Control system 22 is coupled to a console 12 and one or more robotic arms 43. An AI-driven model generalization engine 115 includes one or more processors 62 and memory 63 storing instructions 67 that, when executed, cause the system to execute one or more of: receive intraoperative data from a robotic-assisted surgical procedure of a first type, the data comprising at least one of: endoscopic video, robotic arm 43 kinematics, force feedback, tool trajectory, biometric sensor data, audio commands, haptic feedback, or tactile sensor input; identify transferable feature representations using a multi-task learning framework trained across a plurality of distinct surgical procedure types; determine procedural similarity based on anatomical context, tool usage metrics, or temporal patterns; select and activate an AI model previously trained on a different surgical procedure type but exhibiting latent similarity; generate AI-based surgical guidance or predictive insights for intraoperative decision support; monitor intraoperative data for deviations from predicted patterns using anomaly detection algorithms; adjust parameters of the activated AI model in response to detected deviations; and update guidance outputs accordingly in real-time.

The multi-task learning framework comprises a shared encoder and a set of task-specific decoders or expert sub-networks for different surgical procedures and includes a mixture-of-experts model with a dynamic gating mechanism to select among multiple procedural experts based on real-time context. The model generalization engine 115 includes a federated learning module 111 configured to: receive model updates from distributed robotic surgical systems performing different procedures; perform privacy-preserving aggregation of the updates using techniques such as differential privacy and secure aggregation; and update the shared encoder and procedural models without transferring identifiable patient data. A visualization interface displays selected model outputs, confidence estimates, and visual overlays on endoscopic images. System 10 can integrate pre-operative planning data with real-time intraoperative inputs to improve procedural outcome predictions. The model generalization engine 115 operates across a distributed computing environment comprising an edge processor 62 within the surgical suite and a remote cloud-based analytics server. The adaptive update module 111 utilizes reinforcement learning to optimize parameter tuning during surgery. The similarity scoring module 111 computes a relevance score between current intraoperative data and a plurality of prior case data using learned latent space embeddings. A master command observer estimates commanded positions and velocities based on inputs including commanded joint positions and master motor drive feedback values.

The master command observer outputs can include estimated values for command acceleration and external loads applied to the master manipulator 152. Control system 22 includes a filter in a forward control path from the master manipulator 152 to the robotic arm assembly to attenuate high-frequency signals, and an inverse filter in a feedback path from the robotic arm 43 assembly to the master manipulator 152 to compensate for delay introduced by the forward path filter. The filter attenuates frequency content of joint position commands beyond a cut-off frequency to reduce vibrations experienced at a tip of a surgical instrument 18 held by the robotic arm 43 assembly. The inverse filter provides a phase lead in the feedback path to at least partially compensate for a phase lag caused by the filter. The model generalization engine 115 includes a similarity scoring module 111 configured to compute a relevance score between current intraoperative data and a plurality of prior case data using learned latent space embeddings. The robotic surgical system of claim 1, further includes an adaptive update module 111 configured to: monitor intraoperative data for deviations from predicted patterns; adjust parameters of the activated model in response to detected deviations; and update guidance outputs accordingly in real-time.

In one embodiment, a method of enhancing cross-procedure model generalization in a robotic surgical system, includes: capturing intraoperative data during a surgical procedure using robotic system sensors 84, 88 and interfaces; identifying latent features shared across a plurality of surgical procedures using a multi-task deep learning architecture; selecting a procedural model trained on a different but similar surgery based on calculated similarity metrics; generating surgical assistance outputs including trajectory guidance, alerts, or predictive analytics using the selected model; monitoring intraoperative data for deviations from predicted patterns; adjusting parameters of the selected model in response to detected deviations; and updating guidance outputs accordingly in real-time.

The selected model is updated post-operatively using outcomes data and surgeon feedback to improve future case accuracy. The multi-task deep learning architecture has a shared encoder and a set of task-specific decoders or expert subnetworks for different surgical procedures. The selection of a procedural model includes computing a relevance score between current intraoperative data and a plurality of prior case data using learned latent space embeddings. The adjustment of parameters of the selected model in response to detected deviations utilizes reinforcement learning to optimize parameter tuning during surgery. #

Robotic surgical system 10 can include a control processor 62 linked to one or more robotic instruments and surgeon console. A procedure tracking module 111 monitors at least one of surgical instrument 18 activity, surgeon commands, imaging data, and system event logs in real-time. An AI driven workflow optimization engine 115 has at least one trained machine learning model and a data processing subsystem. The AI-driven workflow optimization engine 115 is configured to: receive and analyze intraoperative procedural data using the machine learning model; detect workflow inefficiencies or deviations from a dynamically learned or predefined optimized surgical sequence; generate and prioritize real-time recommendations for workflow modification based on at least one of procedural urgency, real-time risk assessment, or surgeon-specific behavioral profiles; and adapt the recommendations using AI-inferred contextual interpretation of surgical phase, tool trajectory, and historical procedural outcomes. A multimodal user interface is coupled to the workflow optimization engine, configured to present the AI-generated recommendations to the surgeon via visual, auditory, or haptic modalities, and to receive surgeon feedback via gesture, touch, or voice command inputs for continuous AI system 42 model refinement.

The workflow optimization engine 115 further can have a predictive analytics module 111 configured to: forecast workflow bottlenecks, errors, or potential complications based on a combination of real-time surgical data and historical case datasets; and compute a confidence score associated with each recommendation based on model reliability, data completeness, and outcome correlation.

In one embodiment, robotic surgical system 10 includes: a decentralized, with control system 22, architecture configured to enable multiple surgical systems to collaboratively share workflow optimization data and outcomes in real-time across different locations; a reinforcement learning-based feedback engine 115 configured to iteratively refine workflow models based on surgeon responses and postoperative results; and a simulation module 111 configured to utilize the workflow optimization engine 115 to allow pre-operative rehearsal of procedures tailored to surgeon-specific patterns and predicted challenges.

The workflow optimization engine 115 is trained on annotated surgical case datasets including procedure type, timing metrics, adverse events, and instrument 18 trajectory logs. Recommendations are grouped and presented according to procedural phase, surgeon operating history, or institutional protocol alignment. A computer vision module 111 tracks surgical instrument 18 positions and tool states using intraoperative video or sensor 84, 88 inputs. User interface includes adaptive layout controls that dynamically adjust visual recommendation prominence based on surgeon engagement history. The procedure tracking module 111 integrates patient monitoring systems, imaging subsystems, and robotic telemetry into a unified data stream. The predictive analytics module 111 incorporates domain-specific risk models to generate alerts prior to task execution deemed high-risk. Haptic modality of the user interface is configured to vary in intensity or pattern based on the urgency of a recommendation. A data fusion engine 115 preprocess and synchronizes multimodal inputs from sensors 84, 88, instruments, and surgical imaging prior to model inference. Decentralized control architecture includes edge-compute nodes with secure synchronization protocols for maintaining data integrity and latency tolerance.

The reinforcement learning-based feedback engine 115 employs reward weighting based on clinical outcomes, task completion time, or safety metrics. The workflow optimization engine 115 is configured to operate in a passive monitoring mode and switch to active recommendation mode upon detecting deviation thresholds. A surgeon customization profile can tune model selection and UI configurations according to individual preferences and cognitive workload. Feedback from the user interface is stored and used to generate longitudinal surgeon behavior models to support personalized AI-assisted guidance. The simulation module 111 includes a real-time visualization of alternate task paths ranked by risk-benefit analysis. The workflow optimization engine 115 is capable of switching between multiple concurrently running models based on shifting intraoperative context signals. Recommendation engine 115 includes fallback logic that reverts to predefined clinical protocols if model confidence drops below a minimum threshold. The confidence score is presented alongside each recommendation in the user interface, and recommendations with low scores are dimmed or delayed unless explicitly requested.

Robotic surgical system 10 can be orchestrated multi-instrument 18 collaboration System 10 includes: surgeon console configured to receive surgeon inputs and provide control signals; console 16 coupled to a plurality of robotic arms 43, each configured to manipulate a surgical instrument; sensor 84, 88 array configured to collect real-time intraoperative data, including at least one of visual imaging, instrument 18 position, force feedback, and tissue characteristics; and control system 22. Control system 22 includes: processor 62; memory 63 storing instructions 67 and an artificial intelligence engine, wherein instructions 67, when executed by processor 62, cause the system to: analyze the intraoperative data and surgeon inputs using a machine learning model to determine a procedural state; predict a forthcoming multi-instrument 18 surgical maneuver based on procedural phase classification and historical data using the artificial intelligence engine; generate a coordinated plan for the surgical instruments, including trajectories, velocities, and activation timings; simulate the plan to identify potential collisions or suboptimal interactions; and dynamically adjust the plan in real-time using reinforcement learning feedback to resolve identified issues. The adjusted plan is executed by transmitting control signals to the robotic arms 43.

Control system 22 can include an artificial intelligence engine 115 employing a reinforcement learning model trained on simulated and historical multi-instrument 18 surgical data. The sensor 84, 88 array includes sensor 84, *88s* for detecting tissue proximity and anatomical structures. Control system 22 proactively staged non-active surgical instruments in optimal positions for anticipated use. Control system 22 generates orchestration confidence scores based on alignment with predicted behavior patterns. Additionally, control system 22 prompts surgeon confirmation or override if the confidence score falls below a predefined threshold.

Control system 22 can dynamically determine and suggest optimal tool selection sequences for surgical sub-tasks. A visualization module 111 can be provided that is integrated with the surgeon console and displays predicted trajectories and potential collision zones. A contextual fluidity model adjusts coordination strategies in response to intraoperative variability. A surgeon behavior profiling module 111 models surgeon preferences and bias orchestration predictions. Orchestration involves temporal synchronization of surgical instruments to sub-second precision. A haptic and auditory cue module 111 delivers anticipatory feedback regarding upcoming instrument 18 coordination events. A procedural urgency engine 115 detects elevated risk events and reprioritize instrument 18 coordination. A cloud-connected orchestration refinement module 111 aggregates de-identified data and updates local models via federated learning. A post-procedural analytics module 111 logs coordination events and generate performance reports. A virtual training module 111 simulates multi-instrument 18 maneuvers for surgeon rehearsal. An intraoperative calibration module 111 automatically recalibrates instrument 18 alignment based on real-time sensor 84, 88 feedback.

A method for orchestrated multi-instrument 18 robotic surgery included: receiving real-time intraoperative data and surgeon inputs; determining a procedural state based on the received data; predicting a forthcoming multi-instrument 18 surgical maneuver; generating a coordinated plan for the surgical instruments; simulating the plan to identify potential issues; adjusting the plan in real-time to resolve identified issues; and executing the adjusted plan by controlling the robotic arms 43. An orchestration confidence score and prompting surgeon confirmation or override if the score falls below a predetermined threshold. Dynamic safety zones can be defined within the surgical field and adjusting the coordinated plan to ensure no instrument 18 violates an active safety zone.

An AI system 42 assisted robotic surgical system 10 for neoplasm resection includes a robotic manipulator 152 configured to perform tissue resection with sub-millimeter precision; one or more intraoperative imaging devices including a hyperspectral imaging module 111 configured to capture high-resolution spectral data of tissue in real time; and a data acquisition module 111 configured to receive preoperative imaging data, including at least one of computed tomography (CT), magnetic resonance imaging (MRI), ultrasound, positron emission tomography (PET), or X-ray. An image fusion engine 115 co-registers and aligns preoperative imaging data with intraoperative imaging data to generate a fused anatomical dataset. An AI system 42 analysis engine 115 is coupled to the imaging module 111 and trained to identify and classify cancerous versus healthy tissue based on spectral and anatomical features. A resection guidance module 111 computes and updates an optimal excision path based on outputs from the AI system 42 analysis engine 115 and fused dataset. Control system 22 autonomously or semi-autonomously adjusts the trajectory of the robotic manipulator 152 based on the excision path, in real time. A visualization interface renders overlays, including real-time tumor margins and resection guidance, onto a surgical display 32 or augmented reality system.

The hyperspectral imaging module 111 can have a snapshot hyperspectral camera with real-time spectral unmixing capabilities. The AI system 42 analysis engine 115 can have a hybrid neural network including a convolutional neural network and a transformer model trained on annotated tumor pathology datasets. The image fusion engine 115 can support multimodal alignment between any two or more imaging modalities selected from CT, MRI, PET, ultrasound, and hyperspectral imaging. The resection guidance module 111 includes surgical safety margins based on anatomical boundaries and oncologic risk profiles. Control system 22 supports switching between autonomous, semi-autonomous, and manual operation modes. A calibration module 111 detects and corrects misalignments in robotic instruments using anatomical fiducials and intraoperative imaging. Calibration is automatically triggered when spatial drift exceeds a predefined threshold. The visualization interface renders depth-coded overlays indicating tumor boundaries, confidence metrics, and critical structure proximity. A user interface allows real-time modification of AI-suggested resection paths by the surgeon. The AI system 42 analysis engine 115 computes a margin confidence score and generates uncertainty maps overlaid on the live surgical field. Control system 22 has a predictive motion compensation module 111 and a tissue deformation feedback loop. The module 111 is configured to: predict physiological movements including respiratory and cardiac motion; and dynamically adjust robotic manipulator 152 trajectories in response to intraoperative tissue deformation to maintain precise margin control. A reinforcement learning module 111 updates AI system 42 models based on postoperative pathology results.

A non-transitory computer 151-readable medium storing instructions 67 that, when executed by a processor 62, cause processor 62 to perform operations including: acquiring preoperative and intraoperative imaging data; generating a fused anatomical model; analyzing the model using an AI system 42 engine 115 to identify tumor margins and compute surgical paths; generating visual overlays for surgeon guidance; and adjusting robotic manipulator 152 trajectories based on AI system 42 guidance in real time.

The computer 151-readable medium includes retraining the AI system 42 engine 115 with postoperative histopathological data. The overlays can include tumor classification maps, margin confidence levels, and alerts for unsafe trajectories.

A method for AI-assisted robotic tumor resection includes: acquiring preoperative imaging data; capturing intraoperative imaging data including hyperspectral imaging; co-registering the imaging datasets to generate a fused anatomical model; analyzing the fused model using a trained AI system 42 engine 115 to identify tumor margins; generating a surgical resection plan including real-time updates; guiding a robotic manipulator 152 to execute the plan with sub-millimeter precision; and rendering augmented overlays of tumor margins and critical structures onto a surgical display 32 for intraoperative visualization.

The method can update the surgical plan in real time in response to tissue deformation or robotic drift. The AI system 42 engine 115 can incorporate historical surgical data and reinforcement learning for predictive modeling. Overlays can be rendered using an augmented reality headset or a heads-up surgical display.

Robotic surgical system 10 includes: a robotic instrument 18 coupled to a controller and configured to interact with biological tissue. A physiologic sensing subsystem has one or more sensors 84, 88 to detect real-time physiological parameters. Sensors 84, 88 include at least one of: tissue oxygenation sensors, perfusion sensors, bioimpedance sensors, or neural conductivity sensors. A boundary mapping engine 115 is coupled to the physiologic sensing subsystem and includes an artificial intelligence (AI) module 111. The AI system module 42 is trained to: generate dynamic boundary zones within a surgical field based on sensed physiological thresholds and contextual procedural data; classify zones as high-risk based on learned thresholds derived from patient-specific models, historical surgical outcomes, or intraoperative signal patterns; and generates an instrument 18 constraint map corresponding to the boundary zones and continuously refine it based on ongoing sensor 84, 88 inputs and AI-inferred trends. Control system 22 is configured to: receive the instrument 18 constraint map; restrict, dampen, or modify robotic instrument 18 movement to prevent intrusion into AI-classified high-risk boundary zones; and logs override attempts, constraint violations, and uses AI system 42 confidence scores for real-time or retrospective analysis. A visualization interface presents real-time physiological boundary overlays, constraint zones, and AI-generated risk indicators to the surgeon.

The physiologic sensing subsystem can include a multi-spectral optical sensor configured to estimate tissue perfusion and oxygen saturation in real time. The boundary mapping engine 115 can include a machine learning model trained to identify patient-specific critical zones based on anatomical location, tissue signal patterns, and procedural context. Constraint enforcement can include real-time damping of instrument 18 velocity and automatic retraction upon proximity to high-risk zones. The instrument 18 constraint map can be updated at a refresh rate of at least once every 100 milliseconds based on streaming sensor 84, 88 data. Override of boundary constraints requires dual authentication from the surgical console with timestamped justification entry. A fallback mode can be included in which constraint enforcement is temporarily relaxed during critical surgical emergencies, with automatic reactivation based on time or distance conditions. The visualization interface includes color-coded overlays representing safe, caution, and restricted physiological zones. Constraint zones are dynamically expanded or contracted based on tissue response trends over time, including recovery or degradation of physiologic signals. Control system 22 integrates boundary constraints with other autonomy layers including AI-guided path planning and deviation correction.

In another embodiment, a robotic surgical system has a plurality of robotic instruments configured for multi-arm 43 cooperative procedures. A physiologic boundary engine 115 receives streaming data from multimodal sensors 84, 88 including at least optical, electrical, and mechanical signal inputs. An adaptive control system 22 is configured to: integrate physiologic risk maps across instrument 18 trajectories; synchronize movement constraints across robotic arms 43 to enforce collective safety envelopes; and initiate fallback or retreat maneuvers based on boundary condition violations. An analytics module 111 tracks physiologic zone evolution over time and predict risk trends for surgical planning.

As a non-limiting example, physiologic zone predictions are used to preemptively adjust tool trajectories to avoid transient ischemic or neural boundaries. The fallback maneuvers can include staged instrument 18 withdrawal coordinated with haptic or visual alerts to the surgeon. The analytics module 111 generates a temporal heatmap of evolving physiologic risks for intraoperative review. At least one robotic arm 43 is designated for active constraint monitoring and adjustment enforcement on other arms 43. A data logging subsystem generates compliance reports detailing constraint interactions and override patterns by procedure and operator.

A method for real-time physiologic boundary enforcement in robotic surgery can include: sensing physiological parameters from tissue using at least one intraoperative sensor; identifying regions exceeding risk thresholds based on the physiological parameters; generating a constraint map comprising restricted, cautionary, and free-access zones; modifying robotic instrument 18 behavior based on the constraint map to prevent movement into restricted zones; and displaying boundary zones and instrument 18 restrictions to the surgeon in real time.

The constraint map is continuously updated based on changes in oxygenation, perfusion, or impedance as detected intraoperatively. Movement into restricted zones is prevented unless an authenticated override is received. A surgeon overrides can be logged and instrument movement data for postoperative review.

In one embodiment, a method for performing a surgical procedure using a robotic surgical tool and an artificial intelligence (AI) system, includes: accessing a surgical plan corresponding to the surgical procedure, the surgical plan comprising a workflow with a plurality of sequential procedural steps, each associated with an anatomical feature; for each of the plurality of procedural steps: acquiring one or more intra-operative images of the associated anatomical feature using one or more imaging devices; retrieving one or more pre-operative images of the anatomical feature; processing the intra-operative and pre-operative images using a trained AI model configured to estimate a location of the anatomical feature; and generating a confidence level indicating a likelihood that the estimated location is accurate, based on the output of the AI system. One or more virtual safety boundaries around the anatomical feature are set based on the confidence level; The one or more virtual boundaries are dynamically updated in real time in response to fluctuations in the confidence level. Using the AI system to control the robotic surgical tool to remain within the defined and updated boundaries during execution of the surgical plan.

The AI system 42 is a convolutional neural network trained on segmented surgical imaging datasets. Confidence scores are calculated from posterior probability outputs of the AI model's classification layer. The surgeon is alerted via visual, audio, or haptic signals when the robotic tool nears or breaches a boundary. Virtual boundaries are updated using data from a separate real-time force or contact sensor. The surgical tool automatically pauses operation if confidence drops below a safety threshold. Supplemental intra-operative data includes 3D point clouds, optical imaging, or thermal imaging.

In one embodiment, a method for adaptive modification of a surgical workflow using an AI system 42 during robotic-assisted surgery, includes: monitoring intra-operative imaging and sensor data in real time using a trained AI system 42 configured to detect anatomical changes and deviations. Current anatomical feature localization is compared with the expected locations defined in the surgical plan. A determination is made whether any confidence score associated with feature localization falls below a threshold, in response, generating one or more workflow adaptation proposals, including procedural step modification, reordering, addition, or removal. The adaptation proposal is presented via a surgeon interface for approval or override. An approved workflow modifications is implemented via a robotic surgical controller. All proposed and executed changes, confidence levels, and surgeon interactions for audit and retraining are logged.

Workflow adaptations are ranked using reinforcement learning based on historical surgical outcome data. System 10 cross-references prior adverse event data when generating adaptation proposals. Proposed adaptations are simulated and predicted outcomes are displayed prior to execution. The adaptation is confirmed through voice, touchscreen, or gesture-based surgeon input.

In one embodiment, a robotic surgical system with AI-driven haptic feedback includes: a robotic surgical tool and end effector. One or more imaging devices acquire intra-operative data. At least one sensor detects force, motion, or tactile interaction. A haptic feedback interface delivers one or more of force, vibration, shear, or thermal stimuli. A processor executes an AI system 42 trained to infer anatomical context and generate haptic control parameters based on sensor and image data. A controller applies haptic control signals in real time with latency below 50 milliseconds, and feedback is modulated according to an AI-inferred interaction classification.

The haptic interface includes a wearable multi-point actuator array. The AI system 42 adapts haptic strength based on surgeon-specific sensitivity calibration. A calibration module tunes baseline thresholds for feedback initiation. The AI system 42 fuses tactile sensor data and visual image data to enhance classification accuracy. A safety controller overrides AI decisions when confidence falls below a predefined limit. The processor logs real-time control parameters, haptic outputs, and sensor readings for post-operative review. The surgeon interface displays augmented reality overlays with dynamic boundary visualization and confidence heatmaps.

#Each of following references is expressly incorporated herein by reference in its entirety:

Abraham, Ittai, et al. "Low-distortion inference of latent similarities from a multiplex social network." SIAM Journal on Computing 44.3 (2015): 617-668.

Aldenderfer, M. S., and R. K. Blashfield. Cluster Analysis. Sage Publications, Los Angeles, 1985.

Anderberg, M. R. (1973). Cluster Analysis for Applications. Academic Press, New York.

Anderson, E. (1957). A semi-graphical method for analysis of complex problems. Proc. Nat. Acad. Sci. USA 43923-927.

Anderson, T. W. (1958). An Introduction to Multivariate Statistical Analysis. Wiley, New York.

Anderson, T. W., and Bahadur, R. R. (1962). classification into two multivariate normal distributions with different covariance matrices. Ann. Math. Statist. 33 420-431.

Andrews, D. F. (1972). Plots of high-dimensional data. Biometrics 28 125-136.

Ankerst, M., M. M. Breunig, H.-P. Kriegel, and J. Sander. OPTICS: Ordering Points To Identify Clustering Structure. In Proc. of 1999 ACM-SIGMOD Intl. Conf. on Management of Data, pages 49-60, Philadelphia, Pa., June 1999. ACM Press.

Arabic, P. (1977). clustering representations of group overlap. J. Math. Soc. 5 112-128.

Arabic, P. and Carroll, J. D. (1980). MAPCLUS: A mathematical programming approach to fitting to ADCLUS model. Psychometrika 45211-235.

Arabic, P., L. Hubert, and G. D. Soete. An overview of combinatorial data analysis. In P. Arabic, L. Hubert, and G. D. Soete, editors, Clustering and Classification, pages 188-217. World Scientific, Singapore, January 1996.

Art, D., Gnanadesikan, R., and Kettenring, J. R. (1982). Data-based metrics for cluster analysis. Utilitas Mamatica 31A 75-99.

Asimov, D. (1985). Grand tour. SLAM J. Sci. Statist. Corn-put. 6 128-143.

Auffarth, Benjamin, Yasumasa Muto, and Yasuharu Kunii. "An artificial system for visual perception in autonomous Robots." Proceedings of IEEE International Conference on Intelligent Engineering Systems. 2005.

Babu, B. Hari, N. Subash Chandra, and T. Venu Gopal. "Clustering Algorithms For High Dimensional Data—A Survey Of Issues And Existing Approaches."

Baker, F. B. (1974). Stability of two hierarchical grouping techniques, Case I: Sensitivity to data errors. J. Amer. Statist. Assoc. 69440-445.

Ball, G., and D. Hall. A Clustering Technique for Summarizing Multivariate Data. Behavior Science, 12:153-155, March 1967.

Banerjee, A., S. Merugu, I. S. Dhillon, and J. Ghosh. Clustering with Bregman Divergences. In Proc. of 2004 SIAM Intl. Conf. on Data Mining, pages 234-245, Lake Buena Vista, Fla., April 2004.

Baraglia, R., Dazzi, P., Mordacchini, M., & Ricci, L. (2013). A peer-to-peer recommender system for self-emerging user communities based on gossip overlays. Journal of Computer and System Sciences, 79 (2), 291-308.

Baragliaa, R., Dazzia, P., Mordacchinib, M., & Riccic, L. A Peer-to-Peer Recommender System for self-emerging user communities based on Gossip Overlays. (2012)

Beck, Carolyn, et al. "Dynamic Coverage and Clustering: A Maximum Entropy Approach." Distributed Decision Making and Control. Springer London, 2012. 215-243.

Becker, P. (1968). Recognitions of Patterns. Polyteknisk, Copenhagen.

Bell, P. A. and Korey, J. L. (1975). QUICLSTR: A FORTRAN program for hierarchical cluster analysis with a large number of subjects. Behavioral Research Methods and Instrumentation 7575.

Berg, Mikko. "Human abilities to perceive, understand, and manage multi-dimensional information with visualizations." (2012).

Birkin, P. Survey Of Clustering Data Mining Techniques. Technical report, Accrue Software, San Jose, Calif., 2002.

Bhat, Sajid Yousuf, and Muhammad Abolish. "A density-based approach for mining overlapping communities from social network interactions." Proceedings of 2nd International Conference on Web Intelligence, Mining and Semantics. ACM, 2012.

Binder, D. A. (1978). Comment on 'Estimating mixtures of normal distributions and switching regressions. j Amer. Statist. Assoc. 73746-747.

Blashfield, R. K., Aldenderfer, M. S. and Morey, L. C. (1982). cluster analysis literature on validation. In Classifying Social Data. (H. Hudson, ed.) 167-176. Jossey-Bass, San Francisco.

Bock, H. H. (1985). On significance tests in cluster analysis. J. Classification 277-108.

Boley, D. Principal Direction Divisive Partitioning. Data Mining and Knowledge Discovery, 2 (4): 325-344, 1998.

Bosley, Daniel, and Vivian Borst. "A General Unsupervised Clustering Tool for Unstructured Data." matrix 100:2.

Boratto, Ludovico. "Group artificial intelligence with automatic detection and classification of groups." (2012).

Bradley, P. S. and U. M. Fayyad. Refining Initial Points for K-Means Clustering. In Proc. of 15th Intl. Conf. on Machine Learning, pages 91-99, Madison, Wis., July 1998. Morgan Kaufmann Publishers Inc.

Breiman, L. Meisel, W. S., and Purcell, E. (1977). Variable kernel estimates of multivariate densities and ie calibration. Technimetrics 19 135-144.

Brineman, L., Friedman, J. H., Olshen, R. A., and Stone, C. J. (1984). Classification and Regression Trees. Wadsworth, Belmont, Calif.

Broadbent, S. R. and Hammersley, J. M. (1957). Percolation Processes, I: Crystals and Mazes. Proc. Cambridge Philos. Soc. 53629-641.

Bu, Yingyi, et al. "HaLoop approach to large-scale iterative data analysis." VLDB Journal—International Journal on Very Large Data Bases 21.2 (2012): 169-190.

Buja, A., Hurify, C. and Mcdonald, J. A. (1986). A data viewer for multivariate data. Computer Science and Statistics: Proceedings of 18th Symposium on Interface 171-174.

Cacoullos, T. (1966). Estimation of a multivariate density. Ann. Math. Statist. 18 179-189.

Cal, Rui, et al. "Scalable music artificial intelligence by search." Proceedings of 15th international conference on Multimedia. ACM, 2007.

Carrizosa, Emilio, and Dolores Romero Morales. "Supervised classification and mathematical optimization." Computers & Operations Research 40.1 (2013): 150-165.

Chang, Chin-Chun, and Hsin-Yi Chen. "Semi-supervised clustering with discriminative random fields." Pattern Recognition 45.12 (2012): 4402-4413.

Chen, H., Gnanadesikan, R., and Kettenring, J. R. (1974). Statistical methods for grouping corporations. Sankhya B 36 1-28.

Chen, Yen Hung. "k Partition-Distance Problem." Journal of Computational Biology 19.4 (2012): 404-417.

Cheng, Hong, et al. "Clustering large attributed information networks: an efficient incremental computing approach." Data Mining and Knowledge Discovery 25.3 (2012): 450-477.

Chernoff, H. (1972). selection of effective attributes for deciding between hypnoses using linear discriminant functions. In Frontiers of Pattern Recognition. (S. Watanabe, ed.) 55-60. Academic Press, New York.

Chernoff, H. (1973a). Some measures for discriminating between normal multivariate distributions with unequal covariance matrices. In Multivariate Analysis Ill. (P. R. Krishnaiah, ed.) 337-344. Academic Press, New York.

Chernoff, H. (1973b). use of faces to represent points in k-dimensional space graphically. J Amer. Statist. Assoc. 68 361-368.

Cherubini, Umberto, and Agnese Sironi. Bond Trading, Market Anomalies and Neural Networks: An Application with Kohonen Nets. No. _012. Society for Computational Economics.

Christou, Ioannis T., George Gekas, and Anna Kyrikou. "A classifier ensemble approach to TV-viewer profile adaptation problem." International Journal of Machine Learning and Cybernetics 3.4 (2012): 313-326.

Clunies-Ross, C. W. and Riffenburgh, R. H. (1960). Geometry and linear discrimination. Biometrika 47185-189.

Cormack, R. M. (1971). A review of classification (with discussion). J Roy. Statist. Soc. A 134321-367.

Cover, T. M. (1968). Estimation by nearest neighbor rule. IEEE Transactions Information ory IT-14 50-55.

Cover, T. M. and Hart, P. E. (1967). Nearest neighbor pattern classification. IEEE Transactions, Information IT-13 21-27.

Dallal, G. E. (1975) A user's guide to J. A. Hartigan's clustering algorithms. (unpublished manuscript) Yale University.

Day, N. E. (1969). Estimating components of a mixture of normal distributions. Biometrika 56463-474.

Day, N. E., and Kerridge, D. F., (1967). A general maximum likelihood discriminant. Biometrics 23313-323. 94 de Master, Trabajo Fin. "Novelty and Diversity Enhancement and Evaluation in Recommender Systems." (2012).

Defays, D. (1977). An efficient algorithm for a complete link method. Computer Journal 20364-366.

Derrac, Joaquín, Isaac Triguero, Salvador García, and Francisco Herrera. "Integrating instance selection, instance weighting, and feature weighting for nearest neighbor classifiers by coevolutionary algorithms."

It is to be understood that present disclosure is not to be limited to specific examples illustrated and that modifications and or examples are intended to be included within scope of appended claims. Moreover, although foregoing description and associated drawings describe examples of present disclosure in context of certain illustrative combinations of elements and/or functions, it should be appreciated that different combinations of elements and/or functions may be provided by alternative implementations without departing from scope of appended claims. Accordingly, parenetical reference numerals in appended claims are presented for illustrative purposes only and are not intended to limit scope of claimed subject matter to specific examples provided in present disclosure.

The invention claimed is:

1. A robotic surgical system comprising:

a surgeon console operatively connected to one or more robotic arms;

a control system comprising at least one processor and memory storing instructions that, when executed, cause the system to:

receive real-time intraoperative data comprising at least one of instrument telemetry, anatomical imaging, sensor input, or surgeon interaction patterns;

query a model registry storing a plurality of artificial intelligence (AI) inference models, each associated with metadata comprising procedural domain, training provenance, performance benchmarks, and override statistics;

compute a model-context alignment score using at least one of similarity metrics, reinforcement learning-based alignment, or heuristic-AI hybrid inference;

select and deploy an AI model based on the alignment score to generate intraoperative guidance;

operate a temporal forecasting module to anticipate model performance degradation or contextual divergence;

initiate a model arbitration event prior to predicted degradation, comprising at least one of dynamic model switching, ensemble inference, concurrent dual-model execution, or notification to the surgeon;

monitor model confidence levels and execute a fallback response when the confidence metric falls below a surgeon-adjustable reliability threshold;

wherein in the fallback response the autonomy of robot is transitioned from full autonomy to reduced-autonomy or manual mode; and annotate all AI-generated outputs with version identifiers, confidence scores, and inference metadata for traceability and retrospective audit.

2. The system of claim 1, wherein the temporal forecasting module comprises a recurrent neural network, transformer-based time series model, or a Bayesian sequence model trained on annotated intraoperative datasets.

3. The system of claim 1, wherein the model registry is federated across surgical institutions and updated via differential privacy protocols to protect patient confidentiality.

4. The system of claim 1, further comprising a visualization module configured to:

overlay AI predictions and divergence indicators on live surgical video feeds;

display model certainty intervals and tissue prediction heatmaps.

5. The system of claim 1, wherein the arbitration strategy includes real-time ensemble voting based on model confidence, prediction divergence, and contextual salience weighting.

6. The system of claim 1, further comprising a surgeon interface configured to:

display transparency indicators including interpretability scores and feature importance;

allow manual override of AI guidance and log such events with timestamp and justification metadata.

7. The system of claim 1, further comprising an alert modulation module configured to adjust alert sensitivity, delivery modality, and frequency based on intraoperative behavior patterns including override rate and attention metrics.

8. The system of claim 1, wherein model arbitration is performed asynchronously to minimize latency during critical control intervals.

9. The system of claim 1, further comprising a regulatory compliance module configured to:

validate real-time model usage against jurisdiction-specific legal and ethical rules;

record an immutable audit trail of AI inferences, override events, model transitions, and feedback annotations.

10. The system of claim 1, further comprising a simulation and pre-selection module configured to:

receive preoperative imaging and case metadata;

simulate model performance in virtual scenarios;

recommend preselected primary and fallback AI models based on contextual fit and surgeon preferences.

11. The system of claim 1, further comprising a predictive duration engine configured to estimate remaining surgical time by analyzing instrument motion, video patterns, and procedure-specific models.

12. The system of claim 1, wherein inference execution is dynamically distributed between local edge compute and cloud-based environments based on latency constraints and model complexity.

13. The system of claim 1, further comprising a surgeon personalization module configured to adapt inference behavior to the preferences and past override history of the operating surgeon.

14. The system of claim 1, wherein each AI model includes an embedded explainability module that:

generates human-readable or visual explanations for each inference;

enables retrospective justification for override events.

15. The system of claim 1, wherein the fallback threshold for arbitration or manual control transition is configurable via the surgeon console in real time, enabling tailored automation aggressiveness.

16. The system of claim 1, further comprising a postoperative learning engine configured to:

extract retraining data from override, arbitration, or adverse event instances;

curate feedback-enhanced datasets for continual model improvement.

17. A robotic surgical system configured for safety-based autonomy transitions, comprising:

a control system configured to execute autonomous or semi-autonomous surgical functions;

a safety transition engine configured to:

monitor operational metrics including AI confidence, sensor fidelity, task complexity, and patient-specific physiological parameters;

compute a cumulative uncertainty index over a sliding time window;

compare the uncertainty index to task-specific safety thresholds;

initiate transition from autonomy to reduced-autonomy or manual mode when thresholds are exceeded;

log contextual data including system state, procedural phase, surgeon response, and environment variables for postoperative review and model refinement.

18. The system of claim 17, wherein the reduced-autonomy state retains passive AI recommendations but requires surgeon validation before execution of any robotic movement.

19. The system of claim 17, wherein the safety transition engine comprises a hierarchical fallback controller that enables:

partial module disablement based on localized sensor or model degradation;

full transition to manual operation upon system-wide failure or override conditions.

20. A robotic surgical system comprising:

a surgeon console operatively connected to a local robotic arm assembly;

a context monitoring module configured to assess real-time operational parameters including network latency, intraoperative stress indicators, system health metrics, and procedural phase;

a multimodal arbitration engine configured to:

dynamically allocate control between AI-driven autonomy and surgeon-directed manual operation based on context monitoring outputs;

implement a phase-adaptive control policy that increases surgeon control during high-risk procedural phases and enhances AI autonomy during routine or repetitive tasks;

adjust levels of autonomy including passive AI guidance, constrained execution, or full autonomy based on predefined safety policies and real-time indicators;

a fallback controller that ensures seamless transition to surgeon-only manual control if any of the operational parameter exceeds predefined risk thresholds;

a contextual audit log storing arbitration decisions, associated context data, and surgeon override activity for postoperative analysis and system learning.

* * * * *